(12) United States Patent
Shen et al.

(10) Patent No.: US 7,371,820 B2
(45) Date of Patent: May 13, 2008

(54) NUTRACEUTICALS FOR THE TREATMENT, PROTECTION AND RESTORATION OF CONNECTIVE TISSUES

(75) Inventors: Bojang Shen, Berala (AU); Peter Ghosh, Fairlight (AU)

(73) Assignee: Institute of Nutraceutical Research PTY Ltd., New South Wales (AU)

( * ) Notice: Subject to any disclaimer, the term of this patent is extended or adjusted under 35 U.S.C. 154(b) by 0 days.

(21) Appl. No.: 10/896,546

(22) Filed: Jul. 22, 2004

(65) Prior Publication Data

US 2005/0020500 A1 Jan. 27, 2005

Related U.S. Application Data

(63) Continuation-in-part of application No. PCT/AU03/00061, filed on Jan. 23, 2003.

(30) Foreign Application Priority Data

Jan. 23, 2002 (AU) .................... PS0112
Mar. 12, 2002 (AU) .................... PS1054

(51) Int. Cl.
C07K 1/00 (2006.01)
(52) U.S. Cl. .................................... 530/350
(58) Field of Classification Search .............. 514/12, 514/54; 435/68.1; 530/350
See application file for complete search history.

(56) References Cited

U.S. PATENT DOCUMENTS

| 5,922,692 A * | 7/1999 | Marino .......................... 514/54 |
| 6,162,787 A | 12/2000 | Sorgente et al. |
| 6,271,213 B1 | 8/2001 | Henderson et al. |
| 6,953,784 B2 * | 10/2005 | Thompson et al. ............ 514/44 |
| 2002/0068718 A1 | 6/2002 | Pierce |

FOREIGN PATENT DOCUMENTS

| BE | 857389 | 1/1977 |
| WO | WO 94/28889 | 12/1994 |
| WO | WO 9725051 A1 * | 7/1997 |

OTHER PUBLICATIONS

Katona G., "A clinical trial of glycosaminoglycan-peptide complex ('Rumalon') in patients with osteoarthritis of the knee," Curr Med Res Opin. 1987, 10(9), p. 625-33. Abstract.*
Gramajo et al., "A single-blind, placebo-controlled study of glycosaminoglycan-peptide complex ('Rumalon') in patients with osteoarthritis of the hip or knee," Curr Med Res Opin. 1989, 11(6), p. 366-73. Abstract.*
Sven Bjornsson, Simultaneous Preparation And Quantitation Of Proteoglycans By Precipitation With Alcian Blue, Analytical Biochemistry (1993) 210, p. 282-291.
Kenneth D. Brandt, et al., Heterogeneity Of Protein-Polysaccharides Of Porcine Articular Cartilage, Biochem. J. (1971) 121, p. 261-270.
Robert A. Greenwald, et al., Human Cartilage Lysozyme, The Journal of Clinical Investigation (1972) vol. 51, p. 2264-2270.
Reinhild Klein, et al., Immunomodulatory Properties Of Rumalon®, A Glycosaminoglycan Peptide Complex, In Patients With Osteoarthritis: Activation Of T Helper Cell Type 2 Cytokines And Antigen-Specific IgG4 Antibodies, The Journal of Rheumatology (2000) 27:2 p. 448-454.
D. V. Kosyagin, Modification Of A Method For Isolation Of The Proteoglycan Fractions From Cartilage, Ukrainskii Biokhimicheskii Zhurnal (1981) 53(5) Abstract.
X. M. Luo, et al., Chicken Keel Cartilage As A Source Of Chondroitin Sulfate, Poultry Science Association (2002) 81, p. 1086-1089.
Mitsuo Majima, et al., Effect Of Proteoglycan On Expiremental Colitis, International Congress Series 1223 (2001) p. 221-224.
Takuo Nakano, et al., Extraction Of Glycosaminoglycan Peptide From Bovine Nasal Cartilage With 0.1 M Sodium Acetate, J. Agric. Food Chem. (1998) 46, p. 772-778.
T. Nakano, et al., An Economical Method To Extact Chondroitin Sulphate-Peptide From Bovine Nasal Cartilage, Canadian Agricultural Engineering (2000) vol. 42, No. 4, p. 205-208.
Lawrence C. Rosenberg, et al., Isolation Of Dermatan Sulfate Proteoglycans From Mature Bovine Articular Cartilages, Journal of Biological Chemistry (1985) vol. 260, No. 10, p. 6304-6313.
Katia Denise Souza Arcanjo, et al., Effect Of Magnesium Chloride And Guanidinium Chloride On The Extraction Of Components Of Extracellular Matrix From Chicken Cartilage, Mem Inst Oswaldo Cruz, Rio de Janeiro (1994) vol. 89(1), p. 93-97.
Kiichiro Tanaka, et al., X-Ray Analysis Of The Conformation Of Chondroitin-4-Sulfate Calcium Salt, J. Biochem. (1978) 83, p. 325-327.
Hiroaki Yamanishi, et al., The Removal Of Non-Collagen Components From Newborn Calf Dermis With Magnesium Chloride Solution, J. Biochem. (1976) 79, p. 131-144.
Mark E. Adams, et al., Extraction And Isolation Of mRNA From Adult Articular Cartilage, Analytical Biochemistry (1992) 202, p. 89-95.
Denko, C.W. "Restorative Chemotherapy in Degenerative Joint Disease (DJD) of the Hip" Presented at the Seventh Pan-American Congress of Rehumatology, Bogota, Colombia, Jun. 1978.
Silberberg, M. and Silberberg, R. "Submicroscopic Changes in Articular Cartilage of Mice Treated with a Cartilage-Bone-Marrow Extract" Experimental Medicine and Surgery 1967; 25(1):46-60.

* cited by examiner

Primary Examiner—Karen Cochrane Carlson
Assistant Examiner—Agnes B. Rooke
(74) Attorney, Agent, or Firm—Frommer Lawrence & Haug LLP; Thomas J. Kowalski; Angela M. Collison

(57) ABSTRACT

The invention relates to a method for isolating from connective tissue a variety of glycosaminoglycan (GAG)-polypeptide complexes and polypeptides which are substantially free of contaminating DNA and other molecules such as viruses which may be associated with the DNA in the cell. The invention also relates to uses of GAG-peptide complexes and polypeptides substantially free of DNA either directly, or after further processing, for the treatment, protection and restoration of connective tissues in inflammatory and degenerative disorders such as rheumatoid arthritis and osteoarthritis in any of their multiple forms or other degenerative conditions in mammals.

11 Claims, 35 Drawing Sheets

Bovine Trachael Cartilage
- before [A & C] and after treatment [B & D]

[A] TB stain = Sulfated GAGs

[B] TB stain = Sulfated GAGs

[C] MassonTC stain = Collagen

[D] MassonTC stain = Collagen

ChSA ($A_{260}$=0.39; $A_{280}$=0.21)

CaP ($A_{260}$=0.12; $A_{280}$=0.11)

NaP ($A_{260}$=0.13; $A_{280}$=0.12)

H2OP ($A_{260}$=0.20; $A_{280}$=0.19)

(A. extracellular matrix)

(B. media)

NUTRACEUTICALS FOR THE TREATMENT, PROTECTION AND RESTORATION OF CONNECTIVE TISSUES

CLAIM OF PRIORITY AND INCORPORATION BY REFERENCE

This application is a continuation-in-part of International Patent Application PCT/AU03/00061 filed January 23, 2003 and published as WO 03/062279 on Jul. 31, 2003, which claims priority from Australian Patent Applications PS 0112 filed Jan. 23, 2002 and PS 1054 filed March 12, 2002.

Each of the above patent applications and publications, and each document cited in this text ("application cited documents") and each document cited or referenced in each of the application cited documents, and any manufacturer's specifications or instructions for any products mentioned in this text and in any document incorporated into this text, are hereby incorporated herein by reference; and, technology in each of the documents incorporated herein by reference can be used in the practice of this invention.

It is noted that in this disclosure, terms such as "comprises", "comprised", "comprising", "contains", "containing" and the like can have the meaning attributed to them in U.S. patent law; e.g., they can mean "includes", "included", "including" and the like. Terms such as "consisting essentially of" and "consists essentially of" have the meaning attributed to them in U.S. patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, nonobvious, inventive, over the prior art, e.g., over documents cited herein or incorporated by reference herein. And, the terms "consists of" and "consisting of" have the meaning ascribed to them in U.S. patent law; namely, that these terms are closed ended.

TECHNICAL FIELD

The invention relates to a method for isolating from connective tissue a variety of glycosaminoglycan (GAG)-peptide complexes and polypeptides which are substantially free of contaminating DNA and other molecules such as viruses which may be associated with the DNA in the cell. The invention also relates to uses of GAG-peptide complexes and polypeptides substantially free of DNA either directly, or after further processing, for the treatment, protection and restoration of connective tissues in inflammatory and degenerative disorders such as rheumatoid arthritis and osteoarthritis in any of their multiple forms or other degenerative conditions in mammals without potential contamination with viruses and other pathogens which are known to be localised within cells and bound to some of their intracellular components.

The invention is also directed to the use of a mixture of the Calcium salt of a GAG-peptide complex(es) and polypeptides, preferably substantially free of DNA, which has been found to enhance connective tissue cell anabolism and macromolecular biosynthesis as well as exhibit immuno-suppressive and anti-inflammatory activities in an animal model. By improving connective tissue cell proliferation, matrix gene expression and inflammation by the above mentioned preparations, even in the presence proinflammatory mediators, such as Interleukin-1 which are known to suppress cellular biosynthesis of matrix components and promote their degradation, these naturally derived GAG-peptide complexes and polypeptides can slow or halt the progression of tissue destruction and inflammation which are characteristic pathological features of arthritis and related degenerative diseases.

BACKGROUND ART

Musculoskeletal disorders such as rheumatoid arthritis (RA), osteoarthritis (OA), disc degeneration (DD) and osteoporosis (OP) are the major cause of morbidity throughout the world. These diseases have a substantial influence on health and quality of life and inflict an enormous cost on health systems (Scott J C, Hochberg M C. Arthritic and other musculoskeletal diseases, In: Chronic Disease Epidemiology, Brownson R C, Remington P L and Davis J L, eds. Washington, D.C. American Public Health Association, 1993). It has been estimated that musculoskeletal diseases cost the Australian community $1.3 billion annually in direct costs and $4.2 billion in indirect cost. This represents 1.3% of GNP (Arthritis Foundation of Australia, Access Economics Pty Ltd report, 2001). Population based studies conducted in other developed countries show similar incidence and health burdens to those of Australia with for example more than 23 million Americans seeking medical treatment for arthritic disorders with costs associated with their management exceeding 70 billion dollars annually (Ruchlin H S, Elkin E B, Paget S A. Assessing cost-effectiveness analyses in rheumatoid arthritis and osteoarthritis. Arthritis C Res 1997;10:413-21). Moreover, the prevalence of OA, DD and OP is rising progressively as the life span of the peoples of developed nations increases. Indeed, it has been estimated that 20% of the population in developed countries will be actively seeking medical treatments or professional heath support for musculoskeletal disabilities by the year 2020 (Croft P. The occurrence of osteoarthritis outside Europe. Ann Rheum Dis 1996;55:661-4).

The aetiology of musculoskeletal conditions such as OA is multifactorial and although ageing is the most strongly associated risk factor, mechanical, hormonal and genetic factors all contribute to varying degrees. OA emerges as a clinical syndrome when these etiological determinants result in sufficient joint damage to cause impairment of function and the appearance of symptoms. This clinical syndrome is manifest radiologically by joint space narrowing due to loss of articular cartilage (AC) and extensive re-modelling of subchondral bone with proliferation at the joint margins (osteophytosis). In the late stages of OA, joints are characterised pathologically by extensive AC fibrillation, loss of staining for proteoglycans (PGs) and eburnation of bone at sites of high contact stress. The subchondral bone beneath those regions of OA where cartilage is fibrillated or eroded is generally sclerotic and consists of immature woven bone (Felson D T. Osteoarthritis. Rheum Dis Clin Nth Amer 1990;16:499-512).

The PGs of AC consist of a protein core to which several hundred GAG chains are covalently attached. The major GAG substituents of the PGs of AC are the Chondroitin sulfates (ChS) whose isomeric structures and their distribution are well known (Poole A R. Changes in collagen and proteoglycan of articular cartilage in arthritis. Rheumatology, 1986, 10; 316-371). Thus in adult cartilage Ch-6-S is more abundant than the corresponding 4-sulfated isomer (Ch-4-S) which predominates in AC of very young animals.

Within the extracellular matrix of AC the hydrated PG complexes are entrapped in the form of macromolecular aggregates by a three dimensional network of Type II collagen fibres. This unique structural organisation of PGs, water and a fibrous collagen network which is anchored in the subchondral bone plate confers to AC the biomechanical properties of resilience necessary for normal biomechanical function (Poole A R. Changes in collagen and proteoglycan of articular cartilage in arthritis. Rheumatology, 1986, 10; 316-371).

Products of cartilage breakdown in OA and RA joints have been shown to be antigenic [Giant T T, Fülöp C, Cs-Szabó G, Buzas E, Ragasa D, Mikecz K. Mapping of arthritogenic/autoimmune epitopes of cartilage aggrecans in proteoglycan-induced arthritis. Scand J Rheumatol 1995;24: 43-9, Rowley M, Tait B, Mackay I R, Cunningham T, Phillips B. Collagen antibodies in rheumatoid arthritis: Significant of antibodies to denatured collagen and their association with HLA-DR4. Arthritis Rheum 1986;29:174-84, Seibel M J, Jelsma R, Saed-Nejad F, Ratcliffe A. Variability in the immunochemical quantification of keratan sulfate in human and bovine cartilage proteoglycans. Biochem Soc Trans 1990;18(5):969-70] and when released into synovial fluid (SF) may provoke a synovial inflammation. This synovitis, once established, can alter the metabolism of resident synoviocytes, the major cellular source of synovial hyaluronan (HA) in joints. Inflammatory mediators released from local macrophage and infiltrating leukocytes can also promote increased vascular permeability and the dilution of SF by plasma fluid, thereby decreasing local HA concentration (Müller-Ladner U, Gay R E, Gay S. Structure and function of synoviocytes. In: Arthritis and Allied Conditions, Koopman W J, ed. Baltimore. Williams and Wilkins, 1997, 243). This dilution of HA coupled with a reduction in its molecular size due to abnormal synthesis by synoviocytes results in a substantial decrease in the rheological properties of SF and consequently its ability to lubricate and protect AC (Balazs E A. The physical properties of synovial fluid and the special role of hyaluronic acid. In: Disorders of the Knee, Helfet A J, ed. Philadelphia. J P Lippincott, 1982, 61-74). Macrophage of the synovium, together with the leukocytes which enter the synovial cavity due to the local inflammation, are also an abundant source of cytokines [eg interleukin-1 (IL-1)], procoagulant factors, proteinases and oxygen-derived free radicals including nitric oxide radical (NO) (Pelletier J-P, DiBattista J A, Roughley P, McCollum R, Martel-Pelletier J. Cytokines and inflammation in cartilage degradation. Rheum Dis Clin N Am 1993;19:545-68, Dean D D. Proteinase-mediated cartilage degradation in osteoarthritis. Sem Arthritis Rheum 1991;20:2-11). While much of the excess proteolytic activity released into synovial fluid is abrogated by the endogenous inhibitors present, cytokines and flee radicals can freely diffuse into cartilage and down-regulate PG and collagen synthesis by chondrocytes. These proinflammatory mediators can also initiate the production of catabolic proteinases, cytokines and free radicals such as NO—by the cartilage cells which via autocrine and paracrine pathways contribute to further AC matrix destruction (Evans C H, Watkins S C, Stefanovic-Racic M. Nitric oxide and cartilage metabolism. Methods Enzymol 1996;269:75-88).

It is clear from the above that in arthritic diseases such as OA all tissues of the joint are affected and their excessive breakdown and the concomitant elicitation of an inflammatory reaction can lead not only to the progression of the disease state but also the initiation of symptoms the most common being pain and impairment of joint function.

Pharmacological management of rheumatic disorders and back pain of discal origin, has up until quite recently, targeted the symptoms of these diseases rather than the underlying pathologies which are the cause of the symptoms. Analgesics, steroidal and non-steroidal anti-inflammatory drugs (NSAIDs) have over the last 50 years, represented the mainstay of pharmacological treatment for the rheumatic diseases. However, the deleterious side effects associated with the use of many of these synthetic drugs (Lichtenstein D R, Syngal S, Wolfe M M. Nonsteroidal antiinflammatory drugs and the gastrointestinal tract. The double-edged sword. Arthritis Rheum 1995;38:5-18, Davies M N, Wallace J L. Nonsteroidal anti-inflammatory drug-induced gastrointestinal toxicity. New insights into an old problem. J Gastroenterol 1997;32:127-33, Manoukian A V, Carson J L. Nonsteroidal anti-inflammatory drug-induced hepatic disorders. Incidence and prevention. Drug Safety 1996;15:64-71, Huskisson E C, Berry H, Gishen P, Jubb R W, Whitehead J. Effects of antiinflammatory drugs on the progression of osteoarthritis of the knee. J Rheumatol 1995;22:1941-6) has prompted the evaluation and development of alternative treatments, particularly remedies from edible plant and animal sources which, by their very nature, are expected to be free of adverse side-effects.

The most widely used products in this regard are glucosamine and chondroitin sulphate (ChS) which are both constituents of cartilage PGs. Although it should be noted that the glucosamine used commercially is generally isolated from the chitosan present in the exoskeleton of crustacea. Controlled clinical studies conducted with glucosamine and chondroitin sulfate, alone or in combination, have indicated that they can provide relief of symptoms in OA (McAlindon T E, LaValley M P, Gulin J P, Felson D T, Glucosamine and Chondroitin for the treatment of Osteoarthritis: a systematic quality assessment and meta-analysis. JAMA, 2000; 263: 1469-1475). These agents have been categorised as slow acting disease modifying anti-osteoarthritis nutraceuticals. We are also aware of a number of patent disclosures describing the use of these agents alone and in combination with various other medicants for the treatment of OA and other musculoskeletal disorders (U.S. Pat. No. 5,364,845, Nov. 15, 1994; U.S. Pat. No. 6,136,795, Oct. 24, 2000; U.S. Pat. No. 6,162,787, Dec. 19, 2000, U.S. Pat. No. 6,271,213, Aug. 7, 2001, U.S. Pat. No. 6,432,929, Aug. 13, 2002, and references cited therein).

Since the ChSs are obtained from natural sources they can be sold directly to the public as food additives or supplements and are not presently require to comply with the rigorous quality control criteria used for synthetically manufactured pharmaceuticals as required by government agencies such as the FDA. Commercially available chondroitin sulfates are normally manufactured from bovine tissues such as lung and trachea by hydrolysis of the GAG protein core linkage of the cartilage PGs using either chemical or enzymatic procedures (U.S. Pat. No. 1,950,100 March 1932, Australian Patents AU-A1-66307/80 January 1981, AU-A-70540/87 December 1987, U.S. Pat. No. 6,162,787, Dec. 19, 2000 and references cited therein). The negatively charged water soluble ChS may be separated and purified from the proteins and peptides also generated by the hydrolysis of cartilage by multiple precipitations with acetone, aliphatic alcohols or the formation of water insoluble complexes with quaternary ammonium salts such as cetyl pyridinium chloride (CPC) (U.S. Pat. No. 1,950,100 March 1932, Australian Patents AU-A1-66307/80 January 1981, AU-A-70540/87 December 1987). However, none of these methods readily remove the contaminating nucleic acids (DNA and RNA)

and other intracellular components also released during the chemical or enzymatic disruption of cartilage since these macromolecules are also anionic and would co-precipitate with the anionically charged ChS.

Contaminating nucleic acids could be selectively removed from the ChS by digestion with enzymes which degrade these contaminating molecules (eg, ribonucleases such as Benzonase (Mercke)), however this is an expensive procedure and the enzymes used would still have to be removed from the ChS preparation at some stage. Choatropic solvents such as guanidine hydrochloride and salt solutions of high ionic strength, such as potassium chloride have also been previously used to extract native proteoglycans from cartilaginous tissues but at low temperatures (below 4 degrees C.) and with the addition of protease inhibitors to prevent degradation of the required macromolecules by endogenous enzymes (Hascall V C and Sajdera S W, Protein-polysaccharide complex from bovine nasal cartilage. The function of glycoprotein in the formation of aggregates. J. Biological Chem. 1969,244;2384-2396; Oegema T, Hascall V, Dziewiatkowski D, Isolation and characterisation of proteoglycans from the rat chondrosarcoma. J. Biol. Chem. 1975, 250: 6151-6159; Inerot S and Heinegard D, Bovine tracheal cartilage proteoglycans. Variations in structure and composition with age. Collagen and Related Research, 1983, 3: 245-262). However, in order to release the GAG-peptides or ChS chains from these so isolated proteoglycan complexes it is necessary to subject them to proteolytic digestion by the addition of exogenous enzymes such as papain to degrade the their protein core (U.S. Pat. No. 6,162,787, Dec. 19, 2000, Inerot S and Heinegard D, Bovine tracheal cartilage proteoglycans. Variations in structure and composition with age. Collagen and Related Research, 1983, 3: 245-262, and references cited therein). Furthermore, use of these high ionic strength or chaotropic conditions to extract cartilage also disrupts cell membranes and thus release intra-cellular components, such as nucleic acids into the aqueous medium along with the PGs.

Uncharacterised GAG-peptides have also been prepared from bovine nasal cartilage but not bovine tracheal cartilage using sodium acetate or water at pH 4.5 (Nakano T. Nakano K, Sim J S, Extraction of glycosaminglycan peptide from bovine nasal cartilage with 0.1 M sodium acetate, J Agriculture and Food Chemistry, 1998, 46; 772-778, Nakano T, Ikawa N, Ozimek L, An economical method for the extraction of chondroitin sulfate-peptide from bovine nasal cartilage. Can Agric Engineering, 2000, 42; 205-208). However, neither the presence or absence of DNA in these GAG-peptide preparations nor their respective pharmacological activities nor direct use for the treatment of musculoskeletal conditions described could be inferred from the information recorded in these publications. Again, in the Nakano et al disclosures subsequent proteolytic or chemical hydrolysis of the products isolated by this method of extraction was necessary to obtain the ChS ultimately required by the authors.

In this regard it is important to note that most of the proteolytic enzymes used to exhaustively digest connective tissues to manufacture products of commercial interest, such as the ChSs are derived from bacterial or plant sources because of their broad range of substrate specificity and widespread availability. The amino acid sequences which are recognised and cleaved by these enzymes, as well as the amino acid sequences of the polypeptide fragments generated by their proteolytic actions, are therefore different to the sites of cleavage and polypeptide sequences produced by the endogenous proteinases of mammalian connective tissues.

For example, studies with the mammalian class of cysteine proteinases, the Cathepsins, have shown that their preferred substrate binding and catalytic cleavage sites are different from that of the plant derived cysteine proteinase, papain (Barrett A j, Buttle D J, Mason R w, Lysosomal cysteine proteinases, ISI Atlas of Science, 1988: 256-260). In addition, while digestion of purified preparations of PGs with papain released single ChS chains with about 10 amino acid stubs still glycosidically attached the corresponding digestions of cartilage PGs with the cathepsins, D or B or G produced clusters containing 2 or more ChS chains and longer amino acid stubs with amino acid sequences different to those generated by the papain digested PGs (Roughley P J and Barrett A J, The degradation of cartilage proteoglycans by tissue proteinases, Biochem J, 1977,167: 629-637).

Certain patent disclosures cite methods of preparation and use of hydrolysates of cartilage for the treatment of musculoskeletal disorders and joint cartilage defects but these inventions are limited to the use of the peptides produced from type I and type II collagens for such treatments and make no reference to pharmacological activities of any GAG-peptide complexes when used alone or in combination with these collagen derived polypeptides. Furthermore none of these previous disclosures recognises the absence or presence of intra-cellular contaminants such as nucleic acids in their preparations (U.S. Pat. No. 3,966,908, Jun. 29, 1976, U.S. Pat. No. 4,804,745 February 1989, U.S. Pat. No. 5,399,347 March 1995, U.S. Pat. No. 5,364,845 December 1996, U.S. Pat. No. 6,025,327 February 2000, U.S. Pat. No. 6,372,794 April 2002).

While the consequences of long term human consumption of bovine or other animal nucleic acids in commercial ChS preparations sold as nutraceuticals or food supplements is presently unknown, it should be noted that these intracellular anionic macromolecules are strongly bound to or form complexes with retroviruses and heat/protease resistant prion proteins which have been implicated in the spread of transmissible spongiform encephalopathies such as Creutzfeld-Jakob disease, kuru, (Gerstmann-Straussler-Scheiner syndrome in humans, scrapie in sheep and goats, and bovine spongioform encapalopathies in cattle. (Weissmann C et al, Transmission of prions, www.pnas.org/cgi/doi/1073/pnas. 172403799; Narang H, A critical review of the nature of the spongiform encephalopathy agent: protein theory versus virus theory, Exp Biol. Med, 2002,227: 4-19; C, et al, The prion protein has DNA strand transfer properties similar to retroviral nucleocapsid protein, J. Mol. Biol., 2001, 307: 1011-1021; Nandi P K and Sizaret P-Y, Murine recombinant prion protein induces ordered aggregation of nucleic acids to condenced globular structures, Arch Virol, 2001, 146: 327-45; Cominicini S, et al, Genomic organisation, comparative analysis and genetic polymorphisms of the bovine and ovine prion Doppel genes (PRND), Mamm Genome 2001, 9: 729-33,). These intracellular entities could therefore be consumed by the subject in appreciable amounts when they comply with the manufactures recommended dosage of one or more grams of ChS daily for the suppression of the symptoms arising from osteoarthritis and related conditions.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

DISCLOSURE OF INVENTION

In a first aspect the invention provides a method for the preparation of a connective tissue-derived GAG-peptide complex and polypeptide said method comprising the steps of:

subjecting particles of connective tissue to enzyme mediated autolysis by contact with an autolysis medium containing a monovalent or divalent salt at an effective pH and temperate such that at least one GAG-peptide complex and at least one polypeptide are released substantially free of DNA, by the proteolytic actions of an endogenous enzyme(s) from within the tissue particles into the autolysis medium, leaving residual tissue particles; and recovering the GAG-peptide complex(es) and polypeptide(s) from the autolysis medium.

Connective tissues are rich in collagens, non-collagenous proteins and proteoglycans. Connective tissue proteoglycans are macromolecular complexes consisting of chains made of sulfated polysaccharides (about 95%) covalently linked to a protein core (about 5%).

Glycosaminoglycan (GAG) refers to the polysaccharide chains of proteoglycans, which are composed of repeating disaccharide units containing a derivative of an amino sugar (either glucosamine or galactosamine) glycosidically linked to glucuronic or iduronic acid. The most common derivatives being o-sulfated esters substituted in the 4 or 6 positions of the N-acetylated glucosamine or galactosamine rings.

Examples of GAGs include hyaluronic acid (hyaluronan) (which is non-sulfated), chondroitin sulfate, keratan sulfate and heparan sulfate.

Cleavage of a proteoglycan structure produces complexes comprising one or more polysaccharide chains attached to a polypeptide fragment derived from the proteoglycan protein core. These complexes are referred to herein as "GAG-peptide complexes".

The term "polypeptide" includes peptides comprising two or more amino acids, but typically having 10 or more amino acids. Polypeptides can typically be derived by chemical or enzymatic cleavage of proteins, wherein proteins include glycoproteins and non-glycosylated proteins. The term polypeptides includes matrix derived polypeptides which may be obtained from cleavage of non-glycosylated or glycosylated proteins. The properties of a polypeptide are determined by the type and sequence of its constituent amino acids.

The preferred monovalent salt is selected from hydrogen, sodium, potassium, ammonium and mixtures thereof, while the divalent salt is preferably selected from calcium, magnesium, copper, zinc and mixtures thereof. The more preferred salts are calcium and magnesium.

The pH may be in the range of from 2.5 to 8.5, preferably 3.5 to 8.0, more preferably 4 to 7 and most preferably 4.5 to 7.

The temperature may be in the range of from 20 to 45° C., preferably 25 to 45° C., more preferably 32 to 45° C., most preferably 37° C.

The invention also provides GAG-peptide complexes and polypeptides substantially free of DNA prepared by the method described above.

The invention still further provides monovalent or divalent salts of GAG-peptide complexes substantially free of DNA and polypeptides substantially free of DNA.

The connective tissue suitable for the method of the present invention includes skin, bone, tendon, ligament and cartilage. The source of connective tissue may be from a wide variety of species including bovine, ovine, porcine, equine, avian, cervine and piscine species. Cartilage is preferred and may be hyaline, elastic or fibro type cartilage. Preferred animal species and anatomical locations of cartilage are bovine, ovine, porcine, cervine or equine, tracheal, articular, auricular or nasal cartilage, chicken sternal or rib cartilage, shark skeletal cartilage and growing deer antler cartilage. Tissues from young animals are preferable to those obtained from more mature, which in the case of the bovine species is greater than 3 years, for example.

The connective tissue may be treated and washed as required by methods known in the art to remove any adhering soft tissues and reduced to the required particle size by means including, but not limited to, mincing, dicing, grinding and the like. Appropriate particle size may be selected on the basis of commercial convenience. Preferred particle sizes are in the order of up to 5 mm, preferably 1-3 mm.

A person skilled in the art will appreciate that the rate of autolysis may vary with many factors including pH, temperature, concentration, tissue type, tissue particle size and time of incubation. In a preferred embodiment, cartilage particles of size 1-3 mm are subject to autolysis in an aqueous medium at a pH of 4-5 and temperature of 32-42° C. for up to 36 hours, preferably 16-24 hours.

The person skilled in the art will also appreciate that there are a number of methods for assaying for DNA content and that sample to sample variations, independent of method used, can be expected. The present inventors have used a DNA fluorescence dye binding assay and a direct spectroscopic method to estimate DNA levels in these preparations. The spectroscopic method is that normally utilized by investigators to quantitate the levels of DNA in water soluble preparations which have a low protein content, while the fluorescence dye binding assay is employed to determine the amounts of DNA-in samples which may contain proteins and other tissue derived molecules (Davis L G, Kuehl W M, Battey J F, Basic methods in Molecular Biology, 2nd Edition, Appleton and Lange, Norfolk, Conn., 1994).

The term "substantially free of DNA" is to be understood in the context of the present invention to indicate a substantial reduction of DNA relative to the known DNA content of raw material (tissue particles prior to autolysis) or to commercial chondroitin sulfate preparations manufactured by alternative methods to those described here. For example, the ratio of sulfated glycosaminoglycans (S-GAG) to DNA in three commercially available chondroitin sulfate preparations was found by the present inventors to average about 300:1 (Table 3). By contrast, GAG-peptides and polypeptides released into an autolysis medium in accordance with the present invention provide ratios of S-GAG to DNA in the autolysis medium of greater than 1000 to 1 and the DNA being undetectable by the DNA Hoechst 33258 fluorescence dye binding assay or spectroscopically. A person skilled in the art would appreciate that ratios of greater than 1000:1 would fall within the scope of the term "substantially free of DNA". By contrast, the ratio of S-GAG to DNA in commercially available ChSA for human consumption with ratios around 300:1 (Table 3) are considered by the inventors not to be substantially free of DNA.

In the context of the present invention, DNA content is used as a marker for intra-cellular macromolecular components. For example, the substantial absence of DNA indicates a substantial absence of intra-cellular components in general such as nucleic acids and any associated molecules.

Methods of recovering the GAG-peptide complexes and polypeptides from the autolysis media are well known in the art. For example, the residual tissue particles are removed by filtration from the autolysis media and the GAG-peptide complexes and polypeptides isolated from the media. Suitable isolation methods include neutralisation of the supernatant followed by:

freeze drying; or precipitation with acetone or aliphatic alcohols; or by the formation of water insoluble complexes with quaternary ammonium salts such as cetyl, pyridinium, chloride: or by separation using size exclusion or ion-exchange or other forms of column chromatography or membrane filtration technology.

GAG-peptide complexes and polypeptides may be further purified and/or separated using conventional procedures. ChSs as their univalent (eg H, Na, K, ammonium) or divalent (eg Ca, Mg, Zn, Cu) salts obtained by mild chemical or enzymatic hydrolysis of the GAG-peptide complexes prepared by the methods described herein are also substantially free of DNA, the ratios of S-GAG to DNA being greater than 1000:1. Collagen peptides may be isolated by methods known in the art (U.S. Pat. No. 4,804,745 February 1989, U.S. Pat. No. 5,399,347 March 1995, U.S. Pat. No. 5,364,845 December 1996, U.S. Pat. No. 6,025,327 February 2000).

In a second aspect the present invention provides a Chondroitin sulfate salt substantially free of DNA, derived from a GAG peptide complex, the GAG peptide complex being obtainable by the method described above.

The present invention also provides a monovalent or divalent salt of chondroitin sulfate substantially free of DNA wherein the monovalent salt is selected from the group consisting of hydrogen, sodium, potassium, ammonium and mixtures thereof, and the divalent salt is selected from the group consisting of calcium, magnesium, copper, zinc and mixtures thereof.

GAG-peptide complexes substantially free of DNA, chondroitin sulfate salts substantially free of DNA and mixtures of GAG-peptide complexes with polypeptides substantially free of DNA may be used for the treatment, protection and restoration of connective tissues in inflammatory and degenerative tissue disorders and as anti-angiogenic agents for the treatment of cancers or antilipideamic/profibrinolytic agents for improving blood flow in dysfunctional blood vessels.

In this regard the inventors were surprised to discover that the pharmacological activities exhibited by the GAG-peptide complexes substantially free of DNA and GAG-peptide complex/polypeptide mixtures substantially free of DNA were superior to the corresponding activities of the commercially available ChS when their pharmacological activities were compared on an equivalent weight basis.

Accordingly, in a third aspect, the present invention provides use of: at least one GAG-peptide complex substantially free of DNA; and/or chondroitin sulfate salt substantially free of DNA; at least one GAG-peptide complex substantially free of DNA and at least one polypeptide substantially free of DNA, for the manufacture of a medicament for the treatment of inflammatory and degenerative tissue disorders such as rheumatoid arthritis and osteoarthritis in any of their multiple forms, atherosclerosis and myocardial ischemia, degenerative and diabetic arteriopathies, thrombosis and embolisms, hyperlipideamis and for the treatment of cancers.

The present invention also provides a method for the treatment of inflammatory and degenerative tissue disorders such as rheumatoid arthritis and osteoarthritis in any of their multiple forms, atherosclerosis and myocardial ischemia, degenerative and diabetic arteriopathies, thrombosis and embolisms, hyperlipideamis and for the treatment of cancers comprising the administration to a subject in need of such treatment an effective amount of at least one GAG-peptide complex substantially free of DNA; and/or chondroitin sulfate salt substantially free of DNA; at least one GAG-peptide complex substantially free of DNA and at least one polypeptide substantially free of DNA.

The chondroitin sulfates may be present as univalent (preferably Na, K, ammonium) or divalent (preferably Ca, Mg, Zn, Cu, more preferably Ca, Mg) salts.

In a fourth aspect the present invention provides a pharmaceutical composition comprising at least one GAG-peptide complex substantially free of DNA; and/or chondroitin sulfate salt substantially free of DNA; at least one GAG-peptide complex substantially free of DNA and at least one polypeptide substantially free of DNA, together with a pharmaceutically acceptable carrier. The chondroitin sulfates may be present as univalent (preferably Na, K, ammonium) or divalent (preferably Ca, Mg, Zn, Cu, more preferably Ca, Mg salts). The pharmaceutical compositions may include excipients known to be used in combination with chondroitin sulfate such as glucosamine.

In a preferred aspect the present invention provides use of a calcium salt of at least one GAG-peptide complex substantially free of DNA and/or a calcium salt of chondroitin sulfate substantially free of DNA for the manufacture of a medicament for the treatment of inflammatory and degenerative tissue disorders such as rheumatoid arthritis and osteoarthritis in any of their multiple forms, atherosclerosis and myocardial ischemia, degenerative and diabetic arteriopathies, thrombosis and embolisms, hyperlipideamis and for the treatment of cancers.

The present invention also provides a method of treatment of inflammatory and degenerative tissue disorders such as rheumatoid arthritis and osteoarthritis in any of their multiple forms, atherosclerosis and myocardial ischemia, degenerative and diabetic arteriopathies, thrombosis and embolisms, hyperlipideamis and for the treatment of cancers comprising the administration to a subject in need of such treatment an effective amount of a calcium salt of at least one GAG-peptide complex substantially free of DNA and/or a calcium salt of chondroitin sulfate substantially free of DNA.

The inventors have found that the use of a mixture of a calcium salt of a GAG-peptide complex and a calcium salt of a polypeptide generated by the method described above enhances connective tissue cell anabolism and cell biosynthesis of macromolecular components such as PGs and HA, even when the cells are exposed to suppressive proinflammatory cytokines and also together exhibit immunosuppressive and anti-inflammatory activities when administered to an animal model of arthritis.

Accordingly, in a fifth aspect the present invention provides use of a calcium salt of at least one GAG-peptide complex and a calcium salt of at least one polypeptide substantially free of DNA for the manufacture of a medicament for the treatment of inflammatory and degenerative tissue disorders such as rheumatoid arthritis and osteoarthritis in any of their multiple forms, atherosclerosis and myocardial ischemia, degenerative and diabetic arteriopathies, thrombosis and embolisms, hyperlipideamis and for the treatment of cancers.

The present invention also provides a method of treatment of inflammatory and degenerative tissue disorders such as rheumatoid arthritis and osteoarthritis in any of their multiple forms, atherosclerosis and myocardial ischemia, degenerative and diabetic arteriopathies, thrombosis and embolisms, hyperlipideamis and for the treatment of cancers comprising the administration to a subject in need of such treatment a calcium salt of at least one GAG-peptide complex and a calcium salt of at least one polypeptide substantially free of DNA. Preferably the calcium salt of the GAG-peptide complex is substantially free of DNA. The calcium salts of the GAG-peptide complexes and polypeptides may be co-isolated from connective tissue, preferably tracheal cartilage, more preferably bovine tracheal cartilage by the method described above.

In a sixth aspect, the present invention provides a pharmaceutical composition comprising a calcium salt of at least one GAG-peptide complex and a calcium salt of at least one polypeptide substantially free of DNA together with a pharmaceutically acceptable carrier. Preferably the calcium salt of the GAG-peptide complex is substantially free of DNA.

In a seventh aspect, the present invention provides use of at least one polypeptide substantially free of DNA for the manufacture of a medicament for the treatment of inflammatory and degenerative tissue disorders such as rheumatoid arthritis and osteoarthritis in any of their multiple forms.

The present invention also provides a method of treatment of inflammatory and degenerate tissue disorders such as rheumatoid arthritis and osteoarthritis in any of their multiple forms comprising the administration to a subject in need of such treatment an effective amount of at least one polypeptide substantially free of DNA.

In an eighth aspect the present invention provides a pharmaceutical composition comprising at least one polypeptide substantially free of DNA together with a pharmaceutically acceptable carrier.

The method of the first aspect of the present invention is essentially nondisruptive to the connective tissue used. Thus the residual tissue particles removed from the autolysis medium after release of the GAG-peptide complexes and polypeptides into the medium can be used as a source of collagen derivatives. In this regard it should be noted that traditional methods for preparing ChS from connective tissues such as cartilage use exhaustive proteolytic or chemical digestion to destroy the proteinaceous components of the matrix to allow the ChS to be released into aqueous solution and isolated. The residual tissue particles obtained by the present method can be hydrolysed proteolytically or chemically and subsequently purified to obtain collagen peptides of variable molecular size to be used for the treatment, protection and restoration of connective tissues in inflammatory and degenerative disorders such as rheumatoid arthritis and osteoarthritis in any of their multiple forms or for the enhancement of wound healing or for the preparation of artificial biomatrixes for cell culture, cell transplantation, or delivery of bioactive compounds including drugs and growth factors into a host tissue.

In a ninth aspect, the present invention provides a method according to the first aspect of the invention further including the step of hydrolysing the residual tissue particles to obtain collagen peptides.

The invention also provides collagen peptides prepared by the method described above.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

In order that the present invention may be more clearly understood, preferred forms will be described with reference to the following examples and drawings.

Figure 1:
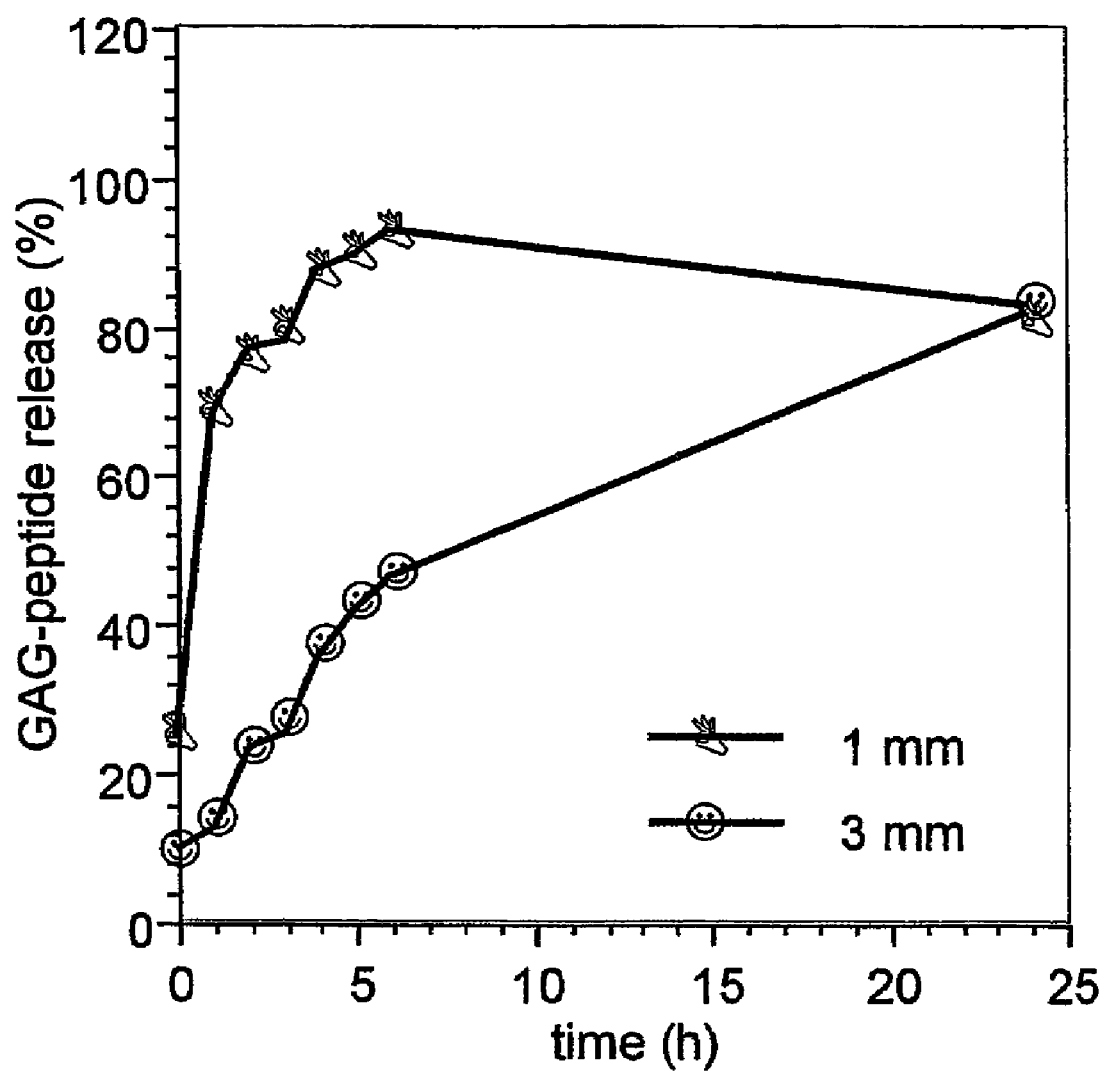
FIG. 1

Kinetics of Glycosaminoglycan-peptide (GAG-peptide) Released from 1 mm and 3 mm Bovine Trachea Cartilage Powders with 100 mM with autolysis buffer, 100 mM calcium acetate, pH 4.5 at 37 degrees C.

FIG. 2

Photomicrographs of histological sections of 3 mm bovine tracheal cartilage powders particles before and after subjecting them to the autolysis procedure using 100 mM calcium acetate buffer, pH 4.5 at 37 degrees C. Panels A and C are sections of cartilage before autolytic processing and B and D after. Panels A and B show the results of staining with Toluidine Blue (TB), a dye which binds to glycosaminoglycans (GAGs) while C and D show sections stained with Masson Trichrome (Masson TC), a dye known to stain native collagen fibres magenta colour. Note the loss of staining for GAGs in section B after autolysis but a slightly increased intensity of staining for collagen following the removal of the majority of GAGs as shown in D. Cell nuclei, identified in these sections by the green counter-stains are clearly unchanged by the autolytic process. All sections are shown at magnification ×400.

FIG. 3

Kinetics of release of glycosaminoglycans-peptides (GAGs) from bovine tracheal cartilage in the presence of 100 mM calcium acetate at 37 degrees C. at various pHs.

FIG. 4

Kinetics of release of glycosaminoglycans-peptides (GAGS) from bovine tracheal cartilage in the presence of 100 mM calcium acetate at pH 4.5 C at various temperatures.

FIG. 5

Release of glycosaminoglycans-peptides (GAGs) from bovine tracheal cartilage in 100 mM calcium acetate buffer at pH 4.5 C at 37 degrees C. in the absence and presence of proteolytic inhibitors. The cysteine protease inhibitor, N-Ethylmaleimide was the most effective inhibitor reducing release by approximately 50% that of the control incubations which contained no inhibitors.

FIG. 6

Superdex-200 Gel Filtration of Calcium Peptacan (CaP) showing sulfated GAG ($A_{535}$) and protein ($A_{562}$) profiles using assays described in the text.

FIG. 7

Superdex-200 Gel Filtration profiles of Calcium Peptacan (CaP) and Papain Digested CaP showing decrease in molecular size to that of chondroitin sulfate.

FIG. 8

Superdex-200 Gel Filtration chromatograms of Peptacans (CaP and H2OP) and ChSAs (Sigma and Bioiberica).

FIG. 9

Standard Curve of distribution coefficient (Kav) versus molecular mass of ChS standards determined on Sephadex-G 200 using the method of Melrose and Ghosh (1993) as described in the text.

FIG. 10

Composite Agarose Polyacrylamide Gel (CAPAGE) Analysis of chondroitin sulfate (ChS) and Calcium Peptacans (CaP). Lane 1: ChS (Sigma), lane 2: CaP, lane 3: purified CaP, lane 4: papain digested CaP.

FIG. 11

Analysis of proteins and peptides in Peptacans Using SDS-Polyacrylamide gel electrophoresis. Lane 1=protein markers with molecular weights shown, lane 2=CaP, lane 3=purified CaP, lane 4=chondroitinase-ABC digested and purified CaP.

FIG. 12

Determination of DNA contamination in ChSA and Peptacans from their UV Spectra. The presence of DNA is indicated by absorption at $A_{260}$ and protein at $A_{280}$.

FIG. 13

Binding and release of Chondroitin Sulfate A (ChSA) and Calcium Peptacan (CaP) from immobilized lysozyme, hyaluronadase, and human granulocyte elastase using the BIAcore2000 technique. The extent of binding affinity of drugs to immobilized enzymes was recorded as resonance units (RU).

FIG. 14

Short-Term (2 days) Concentration-Dependent Effects of Chondroitin Sulfate A (ChSA) and Calcium Peptacan (CaP) on the Incorporation of $^3$H-methyl Thymidine to DNA of Ovine Chondrocytes in Monolayer Cultures.

FIG. 15

Long-Term (7 days) Concentration-Dependent Effects of Chondroitin Sulfate (ChSA) and Calcium Peptacan (CaP) on the Incorporation of $^3$H-methyl Thymidine into DNA of Ovine Articular Chondrocytes in Monolayer Cultures.

FIGS. 16A and 16B

Concentration-Dependent Effects of Chondroitin Sulfate A (ChSA) and Calcium Peptacan (CaP) on Proteoglycan (PG) Synthesis by Ovine Chondrocytes in extracellular matrix (FIG. 16A) and media (FIG. 16B).

FIG. 17

Effects of Chondroitin Sulfate A (ChSA) and Calcium Peptacan (CaP) on Proteoglycan (PG) Synthesis by Ovine Chondrocytes in the Absence and Presence of Interleukin-1beta (IL-1beta).

FIG. 18

Concentration Effects of ChSA and Peptacans on $^{35}$S Incorporation into PGs of the Extracellular Matrix of Fibrochondrocytes isolated from the Inner Region of Ovine Menisci.

FIG. 19

Concentration Effects of ChSA and Peptacans on $^{35}$S-PGs released into condition medium from the Extracellular Matrix of Fibrochondrocytes isolated from the inner Region of Ovine Menisci.

FIG. 20

Relative Effects of ChSA and Peptacans (2.0 mg/ml) on $^{35}$S-incorporation into PGs of the Extracellular Matrix of Fibrochondrocytes of isolated from the inner Region of Ovine Menisci.

FIG. 21

Relative Effects of ChSA and Peptacans (2.0 mg/ml) on $^{35}$S-PGs released into conditioned medium from the Extracellular Matrix of Fibrochondrocytes isolated from the inner Region of Ovine Menisci.

FIG. 22

Concentration Effects of ChSA and Peptacans on $^{35}$S-incorporation into PGs of the extracellular matrix of Fibrochondrocytes isolated from the outer Region of Ovine Menisci.

FIG. 23

Concentration Effects of ChSA and Peptacans on $^{35}$S-PGs Released into Conditioned Media from Fibrochondrocytes isolated from the Outer Region of Ovine Menisci.

FIG. 24

Relative Effects of ChSA and Peptacans (2.0 mg/ml) on $^{35}$S-incorporation into PGs of the extracellular matrix of Fibrochondrocytes isolated from the outer Region of Ovine Menisci.

FIG. 25

Relative Effects of ChSA and Peptacans (2.0 mg/ml) on $^{35}$S-PGs Released into Conditioned Media from Fibrochondrocytes isolated from the outer Region of Ovine Menisci.

FIG. 26

Concentration Effects of Chondroitin Sulfate A (ChSA) and Calcium Peptacan (CaP) on DNA Synthesis by cultures of Human Synovial Fibroblasts (HSF) from Joints of Osteoarthritic Patients. Concentrations of CaP between 62 and 250 micrograms/mL produced significant stimulation of synthesis (p<0.05).

FIG. 27

Effects of ChSA, CaP and H2OP (2.0 mg/ml) on HA Synthesis by Human Synovial Fibroblasts (HSF) as shown by the radioactivity profiles obtained on Superose 6 Gel Filtration chromatography.

FIG. 28

Relative Effects of Chondroitin Sulfate A (ChSA) and Peptacans (2.0 mg/ml) on Hyaluronan (HA) Synthesis by Human Synovial Fibroblasts (HSF) Derived from Joints of Osteoarthritic Patients.

FIG. 29

Relative effects of Chondroitin Sulfate A (ChSA) and Peptacans and highly purified Peptacans (2.0 mg/ml) on Hyaluronan (HA) Synthesis by Human Synovial Fibroblasts (HSF) Derived from Joints of Osteoarthritic Patients. Note the diminished activity of pCaP relative to CaP.

FIG. 30

Superose-6 Gel Filtration chromatograms of media removed from cultures of synovial fibroblasts obtained from joints of arthritic rabbits of non-drug treated controls (broken lines) and 4 animals treated daily with 300 mg/ml of CaP for 14 days (solid lines) showing increased synthesis of radioactively labeled HA.

FIG. 31

Mean (±SEM) group effects of ChS and CaP treatments on the ex-vivo synthesis of radioactively labelled HA by synovial fibroblasts from rabbit joints. Only cells from the CaP treated groups at 300 mg/kg showed a significant increase in synthesis relative to the non-drug treated control group (p<0.05).

FIG. 32

Photomicrograph of histological sections of patella cartilage (AC) and adjacent synovium from joints of the rabbit PC arthritis model showing the extensive synovial inflammation and pannus formation accompanied by antibody staining for inducible nitric oxide synthase (iNOS) in chondrocytes. Panels A and B: sections from saline injected joints but processed and stained with the iNOS primary and secondary antibodies as described in the text. Note the strong non-specific brown staining of synovial tissue but not chondrocytes (which appear blue from the counter-stain) or the cartilage matrix in these control sections. A=100×, B=400× magnification. Panels C and D are sections from PC injected non-drug treated joints. C=100×, D=400× magnification. Intense staining for iNOS in chondrocytes is evident in these sections. Panel E is a section from PC injected joint of a ChS treated animal magnification ×400. Staining for expression of iNOS by chondrocytes is less than in the non-drug treated control but is still apparent. Panel F is a representative section from a PC injected joint of a CaP treated animal (300 mg/kg) where staining for iNOS in chondrocytes is reduced relative to control and ChS treated groups. Magnification ×400.

FIG. 33

Photomicrograph of histological sections of patella cartilage and adjacent synovium from joints of the rabbit PC arthritis model showing the extensive synovial inflammation and pannus formation accompanied by brown antibody staining in chondrocytes for the nitric oxide synthase oxydation product, nitrotyrosine. The section shown in Panel A is from PC injected non-drug treated rabbit joints process and stained with the primary and secondary bodies for nitrotyrosine as described in the text. Note as in FIG. 32 the strong brown non-specific staining of synovial tissue but specific staining for the antigen in chondrocytes, particularly in the cartilage superficial zone. Magnification ×400. Panel B shows a representative section from a PC injected joint of a ChS treated animal where staining is reduced in intensity but not absent. Magnification ×400. Panel C is a section from a PC injected joint of an animal given CaP (300 mg/kg). Magnification ×200. Staining for nitrotyrosine in chondrocytes and in the superficial cartilage zone was slight and less than in the non-drug treated control. Panel C is a negative control section from a PC injected joint which confirms the non specific binding of the nitrotyrosine antibody to synovial tissues but not cartilage or chondrocytes.

FIG. 34

Histograms showing the mean values (±SEM) for neutrophils in the blood of animals from the ChS and CaP treated rabbit groups. Note the suppression of neutrophil levels in blood from the high dose CaP treated group.

FIG. 35

Histograms showing the mean values (±SEM) for mononuclear cells in the blood of animals from the ChS and CaP treated rabbit groups. Note the reduction of mononuclear cells levels in the 300 and 200 mg/kg CaP treated groups.

MODES FOR CARRYING OUT THE INVENTION

Abbreviations and Definitions

In order to avoid repetition and improve the clarity of this description of the products isolated from cartilages by the methods of the invention they have been abbreviated and given the collective title of PEPTACANS (P). The different Peptacans isolated by the methods herein are identified by the addition of prefixes, Thus:

Calcium Peptacan (CaP)—is the aqueous soluble product obtained by subjecting bovine tracheal cartilage powder to autolysis at 37° C. with 0.1 M calcium acetate at pH 4.5.

Sodium Peptacan (NaP)—is the aqueous soluble product obtained by subjecting bovine tracheal cartilage powder to autolysis at 37° C. with 0.1 M sodium acetate at pH 4.5.

Water Peptacan (H2OP)—is the aqueous soluble product obtained by subjecting bovine tracheal cartilage powder to autolysis at 37° C. with dilute acetic acid pH at 4.5, dCaP—is CaP dialysed against $H_2O$
dNaP—is NaP dialysed against $H_2O$
dH2OP—is $H_2OP$ dialysed against $H_2O$
pCaP—is CaP purified by gel filtration or ion exchange chromatography
pNaP—is NaP purified by gel filtration or ion exchange chromatography
pH2OP—is H2OP purified by gel filtration or ion exchange chromatography

Experimental Protocols

Bovine, ovine, cervine or porcine tracheal cartilage or nasal cartilage, chicken sternal cartilage, or skeletal shark cartilage or deer antler cartilage were freed of adhering soft tissues mechanically or as described previously U.S. Pat. No. 5,399,347 March 1995, U.S. Pat. No. 5,364,845 December 1996, U.S. Pat. No. 6,025,327 February 2000). These cleaned hyaline cartilages were rinsed with water, minced into 1 mm or 3 mm sizes, freeze dried and stored at −20° C. Bovine tracheal chondroitin sulfate A (ChSA) was purchased from Sigma Chemical Co, USA or was obtained as a gift from Bioiberica, Barcelona, Spain (batch 1/0015, batch 05/2001, batch 18/11/99). All other chemicals were of analytical grade and were purchased from local suppliers.

Release of Glycosaminoglycan Peptide (GAG-peptide) Complexes and Polypeptides from the Cartilage Powders Studies on the kinetics of release of the GAG-peptides and polypeptides from the cartilage powders using the different buffers (eg sodium or calcium acetate or dilute acetic acid to give the various Peptacan products listed above in abbreviations was undertaken under a variety of conditions. The objective of these experiments was to determine the effects of (i) particle size—3 mm, 5 mm, (ii) different pHs eg. pH range 3.5-7.0, (iii) different temperatures, 4° C., 25° C. and 37° C., and (iv) animal species and tissue locations on the rate of autolysis and product release into the aqueous phase. All the experiments were performed, with stirring and release of sulphated GAGs and polypeptides monitored over 24 hours. Studies on the kinetics of release of the GAG-peptide complexes from the cartilages showed that more than 80% of the GAG content could be mobilised into the aqueous medium after 24 hours. Studies also showed that the rate of release was dependent on the cartilage particle size, the smaller preparations undergoing more rapid release. However, by 24 hours the yields obtained were the same. The pH and temperature were found to be important determinants of the rate of release which indicated that the release process was mediated by endogenous enzymes present within the solid tissues. This proposed mechanism was confirmed by undertaking autolysis experiments in the absence and presence of specific enzyme inhibitors. Since it was found that the addition of N-ethylmaleimide produced the most significant inhibition of GAG-peptide and polypeptides release into the aqueous medium we consider that the cysteine class of proteinases, such as the Cathepsins, were the major, but not exclusive, contributors to the autolytic process.

In all experiments the aqueous phase was separated from the cartilage powders by filtration and the filtrate centrifuged to remove fine particles and then neutralized to pH 7.0 by addition of an alkaline solution containing the desired cation. These Peptacan solutions after chemical analysis were either freeze dried and used directly for pharmacological studies or purified and/or converted to chondroitin sulfates. The freeze dried Peptacans were also used as stock material for the preparation of dialysed and fractionated preparations as described below. Alternatively the Peptacans could be isolated from the aqueous solutions obtained from the cartilage digests by precipitation with excess quantities of acetone, ethanol or methanol, usually by adding 3-5× the volume of the aqueous extracts. The precipitates so obtained would be washed with absolute ethanol and dried under vacuum then stored in a vacuum dessicator.

Histological Examination of Bovine Tracheal Cartilage Samples Before and After Calcium Acetate Autolysis Minced 3 mm cartilage samples before and after treatment with 0.1M calcium acetate, pH 4.5 at 37° C. for 24 hours were fixed in 10% (v/v) neutral buffered formalin for 48 hours. Specimens were then washed, dehydrated in increasing alcohol concentrations (70-100% v/v), and double-embedded in methyl benzoate/celloidin then paraffin wax. Sections (4 um) were cut on a rotary microtome and adhered to Superfrost Plus (Menzel Glaser, USA) glass slides. Histochemical staining with Toluidine blue (TB), a dye which binds to sulfated GAGs and Masson trichrom (TC), a dye that binds to native collagen, were performed in batches under controlled conditions as described previously (Hwa S-Y, Burkhardt D, Little C, Ghosh P, The effects of Diacerein on cartilage and subchondral bone in an ovine model of osteoarthritis, J Rheumatology, 2001, 28: 825-834). Briefly, sections were de-paraffinised, and equilibrated in 70% (v/v) alcohol for 15 minutes, then stained in 0.04% (w/v) Dye/ 0.1M sodium acetate buffer (pH 4.0) for 10 minutes. They were then counter-stained in 0.1% (w/v) fast green for 2 minutes, dehydrated in isopropanol followed by xylene and cover-slips applied.

Purification of Glycosaminoglycan Peptide Samples by Gel Filtration

The freeze-dried Peptacans were dissolved in $H_2O$ to afford concentrations of 4.0 mg/ml of clear solutions. 1.0 ml of above Peptacan solutions was injected into a pre-equilibrated HiLoad 16/60 Superdex 200 column and eluted with 0.5 M NaCl at the flow rate of 1.0 ml/min. Fractions (2.0 ml) were collected in 5-ml plastic tubes. GAG-peptide and protein content of each fraction was determined using sulphated glycosaminoglycan (S-GAG) (Farndale R W, Buttle D J and Barrett A J. Improved quantitation and discrimination of sulfated glycosaminoglycans by use of dimethylmethylene blue. Biochim. Biophys. Acta: 883, 173-177) and BCA assay (Smith P K, Krohn R I, Hermanson G T, Mallia A K, Gartner F H, Provenzano M D, Fujimoto E K, Goeke N M, Olson B J and Klenk D C. Anal. Biochem. 150, 76-85, 1985) respectively. The fractions which were S-GAG-positive were pooled and freeze dried. These were designated as pCaP or pH2OP.

Sulfated Glycosaminoglycan (S-GAG) DMMB Assay

The total S-GAG content of Peptacans was determined by reaction using the metachromatic dye 1,9-dimethylmethylene blue (DMMB) (Farndale R W, Buttle D J and Barrett A J. Improved quantitation and discrimination of sulfated glycosaminoglycans by use of dimethylmethylene blue. Biochim. Biophys. Acta: 883, 173-177). A standard curve was prepared using a commercially available chondroitin sulfate A (ChSA) derived from bovine tracheal cartilage (ICN, USA) in 96-well microtitre plates, ChSA standard and Peptacan samples were diluted in 0.2% sodium formate before DMMB reagent was added and the absorbence at 535 nm read immediately. Softmax software was used to construct a standard curve and calculate the concentration of SAG in Peptacans.

Analysis of CaP Using High Performance Liquid Chromatography (HPLC)

The ratio of chondroitin-4-sulfate (Ch4S) and chondroitin-6-sulfate (Ch6S) isomers in Peptacans were determined using high performance liquid chromatography (HPLC) basically as described by Lee and Tieckelman (Lee G J L and Tieckelman H. The application of high performance liquid chromatography in enzymatic assays of chondroitin sulphate isomers in normal urine. J Chromatography. 222: 23-31, 1981). Freeze dried CaP was dissolved in $H_2O$ and then digested by incubation with 0.125 units of chondroitinase ABC (SKK, Tokyo Japan) at 37° C. overnight. The unsaturated disaccharides were separated in a high performance amino column using 0.2 M ammonium acetate, pH 5.5 as mobile phase and photometrically detected at 232 nm. Peaks were identified by comparison with those of chondroitin sulphate A (Sigma Chemical Co, USA). The area of each peak was measured using NM Image 1.61.1 software.

Determination of Collagen or Collagen Peptide Content in Preparations by Assay for Hydroxyproline The collagen content of cartilage powder, freeze dried Peptacans or cartilage residue after extraction was estimated by measuring the concentration of the amino acid hydroxyproline which is unique to this protein. Each freeze dried Peptacan sample was directly dissolved in $H_2O$ (10 mg/ml) and then hydrolysed in 5 N HCl at 110° C. for 24 h. The unprocessed cartilage powders or residues were papain digested for 24 h first and then centrifuged and the supernatant collected, which was then subjected to 5N HCl hydrolysis as described above. The hydrolysed sample solution was neutralised to pH 7 before dilution and analysis. The hydroxyproline concentration in these solutions was determined using the method of Stegman and Stalder (Stegman H and Stalder K. Determination of Hydroxyproline. Clin. Chim. Acta 18: 267-273, 1967) by using a L-hydroxyproline standard and measuring the absorbance at 562 nm after the addition of chloramine T and p-dimethylaminobenzaldehyde to develop the chromophore. The hydroxyproline concentration was multiplied by 7.4 to give an estimate of the collagen content.

Determination of Protein Content of Preparations by the Bicinchoninic Acid (BCA) Assay The total protein content of cartilage powder, freeze dried Peptacans or cartilage residue after extraction was determined using BCA assay (Smith P K, Krohn R I, Hermanson G T, Mallia A K, Gartner F H, Provenzano M D, Fujimoto E K, Goeke N M, Olson B J and Klenk D C. Anal. Biochem. 150, 76-85, 1985). Cartilage powder and cartilage residue were papain-digested for 16 h and centrifuged to provide clear supernatants. Each freeze dried Peptacan was directly dissolved in $H_2O$ to provide a 2.0 mg/ml solution. 20 µl of each sample solution was added to a well of 96-well plates. Just prior to assay, 50 parts of reagent 1 (0.4% NaOH; 1.7% $Na_2CO_3$; 0.95% $NaHCO_3$; 1.0% bicinchoninic acid; 0.16% $Na_2$-tartrate) was mixed with reagent 2 (4% $CuSO_4.5H_2O$). 200 µl of this working reagent was added to the sample solution. After incubation at 37° C. for 60 min the absorbance $A_{562}$ was read using a Thermomax microplate reader. Bovine serum albumin (BSA) or highly purified gelatine (Sigma Chemical Co) at 0-10 µg/well were used to construct a standard curve.

Composite Agarose Polyacrylamide Gel Electrophoresis (CAPAGE)

Each of ChSA and Peptacan samples (CaP, pCaP or papain digested CaP) were dissolved in $H_2O$ at the concentrations of 1.0-3.0 mg/ml and then mixed 1:1 with CAPAGE sample loading buffer (20 mM Tris-acetate, pH 6.3, 1 mM $Na_2SO_4$, 60% sucrose and 0.01% bromophenol blue). 20 µl of each sample equivalent to 10 µg of GAG was loaded into wells of 2 mm thick CAPAGE gel (0.6% agarose, 1.2% acrylamide, 10 mM Tris-acetate pH 6.3 and 0.25 mM sodium sulfate) and electrophoresed in the CAPAGE running buffer (10 mM Tris-acetate pH 6.3, 0.25 mM $Na_2SO_4$) at 150 V for 2 h. The gel was stained in a solution of 0.02% toluidine blue in 0.1 M acetic acid for 1 h, destained in 0.5 M acetic acid for 2 h and dried on an agarose gel-bound film. The dried gel was rinsed with $H_2O$ and dried again.

Determination of Average Molecular Size of Peptacans Using Gel Filtration Chromatography A HiLoad Superdex-200 prep grade prepacked column (16 mm×60 mm) and previously characterised ChS standards were used to determine the molecular size of the various Peptacans and their digested products. The column was equilibrated with 0.25 M NaCl for at least 3 h prior to loading samples. Sephadex-G200 chromatographed bovine tracheal chondroitin sulfate fractions (CS1-CS7) prepared previously were used as molecular size standards (Melrose J and Ghosh P, Determination of the average molecular size of glycosaminoglycans by fast protein liquid chromatography. J Chromatography, 1993, 637; 91-95). 1.0 ml of standard (0.5 mg/ml) or Peptacans (CaP, $H_2OP$ and pCaP) (1.0 mg/ml) were loaded into columns and chromatographed at a flow rate of 1 ml/min using 0.25 M NaCl solution. Fractions (1.0 ml) were collected in 5-ml plastic tubes. GAG content of each fraction was determined with S-GAG assay. A standard curve was constructed using molecular mass versus distribution coefficient (Kav) of CS1-CS7.

Analysis of Proteins in Peptacans by SDS-PAGE Electrophoresis

ChSA (Sigma) and CaP were dissolved in $H_2O$ and then mixed 1:1 with 2× sample loading buffer (0.07 M Tris HCl, 1.5% SDS, 20% glycerol, 0.2M DTT and 0.1% BPB) to achieve the final concentrations of 4.0-20 mg/ml. The samples were boiled in a water bath for 5 min 20 µl of above samples were loaded into the wells of 8-16% pre-cast Tris-glycine gel (Norvex). See Blue pre-stained low molecular weight range protein markers (Norvex) were loaded into wells on the left-hand side of the gel and electrophoresis was performed at 125 V for 2 h. The gel was stained in Coomassie blue R250 solution (40% ethanol, 10% acetic acid and 0.2% Coomassie R250) for 30 min and destained in a solution containing 10% ethanol and 7.5% acetic acid for 16 h. The gel was dried in a Bio-Rad Gelair drier.

Determination of DNA in Peptacans and Commercial Chondroitin Sulfates Using UV Spectroscopy Chondroitin sulfates (Bioiberica or Sigma) and Peptacans (CaP, NaP and H2OP) were prepared at 1.0 mg/ml in $H_2O$. 100 µl of each sample solution were loaded into a microcuvette and scanned spectrophotometrically over the wavelength range of 220-320 nm. The absorbence curves, $A_{260}$ and $A_{280}$ were recorded for each sample in triplicate. The absorption of light by concentrated aqueous solutions of these preparations at the wavelength of 260 nM in their UV spectra provides a measure of the levels of DNA present; whereas absorption by these solutions at 280 nM is taken as a measure of protein content. The ratio of the $A_{260}$ and $A_{280}$ values is commonly used as an index of DNA purity, with ratios of more than 1.5 being considered to indicate preparations high in DNA.

Determination of DNA in Peptacans and Commercial Chondroitin Sulfates Using the Hoechst 33258 Dye Binding Assay Chondroitin sulfates (Bioiberica or Sigma) and Peptacans (CaP, NaP and H2OP) were prepared at 1.0 mg/ml in $H_2O$ and the DNA content was determined in duplicate by using a fluorometric assay in which the Hoechst 33258 dye on binding to DNA shows a change in fluorescence (Kim Y J, Sah R L Y, Doong J-Y H, Grodzinsky A J. Fluorometric assay of DNA in cartilage explants using Hoechst 33258. Anal Biochem. 1988;174:168-176). For the cartilage preparations prior digestion with papain was employed as described by Kim et al (1988) in the in the above publication. Briefly, DNA was determine by adding 100 µl/well of Hoechst 33258 dye solution to each well of a 96-well plate followed by adding 100 µl of ChS or Peptacan or papain digested samples. The plate was gently agitated for 5 min before measuring the fluorescence using excitation and emission wavelengths of 350 nm and 450 nm respectively and slit widths of 10 nm and 15 nm. Calf thymus DNA (Sigma Chemical Co)(0-25 µg/ml) with a uv spectral ratio of $A_{260}$ to $A_{280}$ of 1.85 was used to construct a standard curve and the DNA content of the preparations determined relative to this standard. DNA results were expressed as a % of the dry weight of the samples.

Determination of Binding Affinity of CaP and ChSA to Lysozyme, Elastase and Hyaluronidase Using BIAcore 2000

The molecular interactions between CaP or ChSA and lysozyme, elastase or hyaluronidase were investigated using a surface plasmon resonance (SPR) biosensor device—BIAcore 2000 system (Pharmacia Biosensor AB). Lysozyme (chicken egg-white, CalBiochem), elastase (human neutrophil, ICN) or hyaluronidase (bovine testes type IV, Sigma) was dissolved in 100 µg/ml in 10 mM sodium acetate, pH 6.0 and immobilized on a CM5 sensor chip by using amine coupling procedure. CaP or ChSA was firstly dissolved in $H_2O$ and then diluted in standard HBS running buffer (10 mM Hepes, pH 7.4, 150 mM NaCl, 3.4 mM EDTA, 0.005% surfactant P20) to 2.5 µg/ml. The binding of CaP or ChSA to immobilized enzymes was determined in four flow cells separately including one of the flow cells (minus ligand) used to record background sensorgrams. 200 µl of CaP or ChSA solution were injected individually on to the immobilized chip surface and the molecular interactions were monitored at the flow rate of 50 µg/ml at 25° C. The sensorgrams were recorded and evaluated using the BIAevcaluation 3.1 software provided with the system.

Inhibition of Human Neutrophil Elastase (HNE) by Peptacans and Chondroitin Sulfate A Stock solutions of chondroitin sulfate A (ChSA) and Peptacans were prepared at 2.5 mg/ml in HNE assay buffer (50 mM sodium phosphate, pH 7.4, 0.1% BSA, 0.025% Triton X100) and serially diluted to give solutions with concentrations within the range 4.9-1250 µg/ml. Triplicate diluted samples (100 µl) were transferred to wells of a microtitre plate to which was added 50 µl of 2.0 µg/ml human neutrophil elastase (HNE) in the HNE assay buffer and the plate incubated at 37° C. for 10 min. Substrate solution (100 µl of 0.5 mM SAAVNA in 12.5% DMSO and 87.5% assay buffer) were added to each well and the absorbence was read at 405 nm 4 times at 30 minute intervals. The elastase inhibition rates were expressed as a percentage of the control rate and a plot of % residual HNE activity versus inhibitor concentrations in the inhibition assay was prepared.

Ovine Chondrocyte Cultures

Freshly prepared or cryopreserved primary ovine articular chondrocytes were removed from liquid nitrogen storage and were immediately thawed at 37° C. in a water bath and rinsed twice in culture medium containing 50 µg/ml gentamicin. The cells were seeded at the density of $2\times10^5$ cells/well in 6-well plates and grown in an atmosphere of 5% $CO_2$ in air at 37° C. for 4 days. Medium was changed every 2 days.

Effects of Peptacans and Chondroitin Sulfate A on DNA Synthesis by Ovine Chondrocytes Using $^3$H-methyl Thymidine Incorporation Assay DNA synthesis in ovine chondrocytes stimulated with chondroitin sulfate A (ChSA) or Peptacans (CaP, NaP or H2OP) was determined in duplicate by the incorporation of $^3$H-methyl thymidine into this nucleic acid. The cell cultures were maintained in monolayer culture in 2.0 ml of DMEM/F12 medium containing 10% FCS and 50 µg/ml gentamicin for 3 days before adding the samples. ChSA or Peptacans were added at the concentrations of 1.95, 3.91, 7.81, 15.6, 31.3, 62.5, 125, 250, 500 and 1000 µg/ml in the above medium and incubated in an atmosphere of 5% $CO_2$ in air at 37° C. for 24 h (short-term) or 6 days (long-term) followed by incubation with 0.25 µCi/well $^3$H-methyl thymidine for a further 24 h. Cells were then harvested and radioactivity in DNA was determined using a □beta-counter. Data were expressed as mean values ±SEM.

Effects of Peptacans and Chondroitin Sulfate A on DNA Synthesis Using a Fluorometric Assay DNA synthesis in human synovial fibroblasts (HSF) was determined in duplicate by using fluorometric assay with Hoechst 33258 dye. The HSF, from joints of osteoarthritic patients, was cultured in monolayer in 6-well plates for 24 h. Then the serial concentrations of ChSA or Peptacans were added at 62.5, 125, 250, 500, 1000 and 2000 µg/ml in DMEM medium containing 10% FCS and 50 µg/ml gentamicin. The cultures were maintained in an atmosphere of 5% $CO_2$ in air at 37° C. for a further 24 h. The cells were detached by trypain/EDTA (0.2%/0.1%) treatment and then papain digested. 100 µl/well of Hoechst 33258 dye solution was added to a 96-well plate followed by adding 100 µl of papain digested samples. The plate was gently agitated for 5 min before measuring the fluorescence using excitation and emission wavelengths of 350 nm and 450 nm respectively and slit widths of 10 nm and 15 nm. Calf thymus DNA (0-25 µg/ml) was used as a standard.

Effects of Peptacans and Chondroitin Sulfate A (ChSA) on Proteoglycan (PG) Synthesis by Ovine Chondrocytes using a $^{35}SO_4$—Incorporation Assay The primary ovine articular chondrocytes prepared as described above were seeded at a density of $2\times10^5$ cells/well in 6-well plates and grown for 4 days before addition of 2.0 ml of different concentrations ChSA or Peptacans (CaP, NaP or H2OP) in DMEM/F12 culture medium containing 10% FCS and 50 µg/ml gentamicin. Compounds were added in the presence or absence of 10 ng/ml recombinant human IL-1. The cultures were grown for further 3 days. Then 40 µCi/well $^{35}SO_4$ were added 24 h prior to the termination of cultures. After a further 24 h incubation at 37° C., conditioned media were collected in microfuge tubes. The cells were rinsed with cold PBS twice and then trypsinized with 0.2% trypsin/0.1% EDTA solution. The cell suspension was collected and centrifuged at 1310×g for 5 min.

Papain digestion to release $^{35}SO_4$-labelled GAGs was performed by adding 0.5 ml of papain digestion buffer (2 µl/ml papain suspension, 5 mM cysteine in PBS pH 6.2) into 0.5 ml of conditioned media, while the cell pellets and their extracellular matrix were directly resuspended in 0.5 ml of papain digestion buffer and incubated at 60° C. overnight. Newly synthesised $^{35}$Sulfated PGs (as $^{35}$S-GAGs) were separated from free $^{35}SO_4$ by the following procedure: To 0.4 ml of each papain digested sample, 0.2 ml of 0.2 M $Na_2SO_4$ plus 50 mg/ml CSA (1:1) was added and vortexed. Then 0.1 ml of 0.4 M $BaCl_2$ was added to each tube and vortexed. The mixture was centrifuged at 1310×g for 10 min. 0.4 ml of the supernatant was transferred into another tube. 0.1 ml of 50 mg/ml CSA plus 0.4 M $BaCl_2$ (2:5) mix was added. Then 0.1 ml of 0.2 M $Na_2SO_4$ was added and centrifuged at 1310×g for 10 min. The last step was repeated once. 0.1 ml of the supernatant was transferred into a pony vial followed by adding 3 ml/vial Eco-lite scintillation fluid and thoroughly mixed. Samples were then counted in an automated β-counter (Canberra Packard 1500 Liquid Scintillation Analyzer).

Ovine Fibrochondrocyte Cultures

The skin and overlying musculature of ovine stifle joints were removed and the external joint capsule sprayed with 70% ethanol. The joints were then opened in a lamina flow hood. The menisci were removed, rinsed with sterile PBS and cut into two parts—the inner and outer regions. The inner and outer meniscus tissues were individually dissected into small pieces and digested separately with 0.2% pronase in culture medium (DMEM containing 10% FCS and 50 µg/ml gentamicin) for 2 h followed by 0.04% callagenase digestion overnight.

The digests were filtered 3 times through 70 µm mesh and rinsed with DMEM culture medium containing 50 µg/ml of gentamicin. The cells were seeded into 75 cm flasks and incubated in an atmosphere of 5% $CO_2$ in air at 37° C. for 7 days to reach confluency. The cells were rinsed twice with sterilised PBS, trypsinized with 0.2% trypsin/0.1% EDTA solution and rinsed twice with culture medium. The cells were subcultured at the density of $2\times10^5$ cells/well in 6-well plates and grown for 2 days in an atmosphere of 5% $CO_2$ in air at 37° C.

The Effects of Peptacans and Chondroitin Sulfate A on Proteoglycan (PG) Synthesis by Fibrochondrocytes using the $^{35}SO_4$—Incorporation Assay The first passage fibrochondrocytes from either inner or outer region of ovine meniscus were seeded at the density of $2\times10^5$ cells/well in 6-well plates and grown for 2 days before 2.0 ml of different concentrations of chondroitin sulfate A (ChSA) or Peptacans (CaP, NaP or H2OP) in DMEM/F12 was added. The cultures were grown for a further 3 days then 40 μCi/well $^{35}SO_4$ was added 24 h prior to the termination of cultures. After 24 h incubation at 37° C., conditioned media were collected in microfuge tubes. The cells were rinsed with cold PBS twice and then trypsinized with 0.2% trypsin/0.1% EDTA solution. The cell suspension was collected and centrifuged at 1310×g for 5 min.

Papain digestion was performed by adding 0.5 ml of papain digestion buffer (2 μl/ml papain, 5 mM cysteine in PBS pH 6.2) into 0.5 ml of conditioned media, while the cell pellets were directly resuspended in 0.5 ml of papain digestion buffer and incubated at 60° C. overnight. Newly synthesised $^{35}$Sulfated PGs (as $^{35}$S-GAGs) were separated from free $^{35}SO_4$ by the following procedure: To 0.4 ml of each papain digested sample, 0.2 ml of 0.2 M $Na_2SO_4$ plus 50 mg/ml CSA (1:1) was added and vortexed. Then 0.1 ml of 0.4 M $BaCl_2$ was added to each tube and vortexed. The mixture was centrifuged at 1310×g for 10 min. 0.4 ml of the supernatant was transferred into another tube. 0.1 ml of 50 mg/ml CSA plus 0.4 M $BaCl_2$ (2:5) mix was added. Then 0.1 ml of 0.2 M $Na_2SO_4$ was added and centrifuged at 1310×g for 10 min. The last step was repeated once. 0.1 ml of the supernatant was transferred into a pony vial followed by adding 3 ml/vial Eco-lite scintillation fluid and thoroughly mixed. Samples were then counted in an automated β-counter (Canberra Packard 1500 Liquid Scintillation Analyzer).

Human Synovial Fibroblast Cultures

Cryopreserved human synovial fibroblast (HSF) derived from joints of patients with osteoarthritis were thawed quickly at 37° C. in a water bath. The entire cell suspension in cryo-vials was transferred to a 15 ml sterile centrifuge tube using a transfer pipette in a lamina flow hood. The tubes were centrifuged at room temperature, at 800 g for 10 min. The supernatant was discarded and the cell pellet completely resuspended in 10 ml DMEM medium containing 10% FCS and 50 μg/ml gentamicin by aspirating with a sterile transfer pipette. The tubes were re-centrifuged at 800 g for 10 min at room temperature. The supernatant was again discarded and the cell pellet completely resuspended in 10 ml DMEM complete medium. The cell suspension was seeded in appropriate numbers of labelled flasks followed by the addition of 15 ml of DMEM complete medium. The cells were incubated in an atmosphere of 5% $CO_2$ in air at 37° C. until confluency. Culture medium was changed every 2 days. To subculture the cells, the flasks were removed from the 37° C. incubator and the cells were rinsed twice at room temperature with PBS. Trypsin/EDTA (0.2/0.1%) solution was added and swirled over the cell layer. The flasks were recapped and maintained at 37° C. for 3-5 min. The cells were checked under a microscope for detachment. DMEM complete medium (2-3 ml per flask) was added and washed over the surface of flasks to collect the released cells. The cells were transferred to centrifuge tubes and centrifuged at 800 g for 10 min at room temperature. The cells were washed twice and then resuspended in 10 ml DMEM complete medium. The cells were then counted using a haemocytometer. The cells were seeded at the density of $1.5\times10^5$ cells/2 ml/well in 6-well plates and grown for 24 h in an atmosphere of 5% $CO_2$ in air at 37° C.

Effects of Peptacans and Chondroitin Sulfate A on Hyaluronan(HA) Synthesis by Human Synovial Fibroblasts (HSF) Using a $^3$H-glucosamine Incorporation Assay The HSF cells were seeded at $1.5\times10^5$ cells/well in the 6-well plates and allowed to attach for 24 h before addition of compounds. Chondroitin sulfate A (ChSA) and Peptacans (CaP and H2OP) solutions were prepared in DMEM culture medium containing 10% FCS and 50 μg/ml gentamicin at double the concentration required in the cultures. The highest concentration prepared was 4.0 mg/ml which was sterilised through a 0.22 μm filter and then serially diluted to give final concentrations of 2000, 1000, 500, 250, 125 μg/ml, 62.5 μg/ml of compounds. One ml of each drug solution was added to each well of 6-well plate. Stock $^3$H-glucosamine was diluted in culture medium to give a 1 μCi/ml solution which was immediately added to each well (1 μCi/well). The plates were incubated for a further 24 h. At culture termination, media was collected into 5 ml capped tubes and stored at −20° C. for $^3$H-HA analysis.

Isolation and Quantitation of $^3$H-Hyaluronan ($^3$H-HA) in Cultures Using Superose 6 Gel Filtration Chromatography Two aliquots of 0.5 ml from each media sample were labelled A and B. 20 μl of 1 M acetic acid, pH 6.0 was added to all aliquots. 50 μl of reaction buffer (20 mM Na-acetate and 0.15 M NaCl, pH 6.0) was added to aliquot A and 50 μl of 5 TRU *Streptomyces* hyaluronidase in reaction buffer was added to aliquote B. All samples were incubated at 60° C. for 3 h followed by boiling for 5 min to inactivate the added hyaluronidase. The samples were store at −20° C. prior to gel filtration.

A gel filtration column prepacked with Superose 6 was used to isolate and identify $^3$H-HA in culture media. Media samples were routinely centrifuged at high speed on a bench Microfuge for 10 min immediately before loading to the column. Samples (200 μl of each) were injected into the column through sample loop and the column was eluted with PBS buffer (0.15 M NaCl, 0.05 M $Na_2PO_4$, pH 7.2) at the flow rate of 0.2 ml/l min. The column eluent was collected at 0.5 ml/fraction for total of 46 fractions and radioactivity was determined using a β-scintillation counter.

Studies on the Effect of Oral Administration of Chondroitin Sulfate or Calcium Peptacan on Joint Inflammatory Mediators, White Blood Cell Numbers and Ex-vivo Synovial Fibroblast Biosynthesis of Hyaluronan in a Rabbit Model of Arthritis The rationale, methodology and pathological outcomes obtained for the rabbit model of arthritis used in the present experiments has been described in detail elsewhere (Page-Thomas D P: Aspects of synovial degradation. Bayer-Symposium, Experimental models of chronic inflammatory disease, 353-365 (1977), Springer-Verlag Berlin; Cambray et al., The effects of dexamethasone in vitro on the production of collagenase and inhibitor by synovial and cartilage explants from joints of rabbits with a proliferative arthritis, Rheumatol Int, 1981, 1: 69-72; Smith et al., The effects of orally administered calcium pentosan polysulfate on inflammation and cartilage degradation produced in rabbit joints by intraarticular injection of a hyaluronate-polylysine complex. Arthritis and Rheumatism, 1994, 37: 125-136). In the present studies, male New Zealand White rabbits of approximately 4 months of age were used and acclimatised to holding cages for 7 days. Animals were then divided into 5 experimental groups according to the criteria provide in the following protocol.

Experimental Protocol

Group A (n=4) Non-drug-treated, Polycation(polylysine)-Hyaluronan complex (PC)-injected intra-articularly into one rabbit knee joint and an equal volume of isotonic saline injected in the contralateral knee joint on day 7.

Group B (n=4) PC-injected intra-articularly into one knee joint and isotonic saline injected into the contralateral knee joint but animals administered 300 mg/kg (body weight) chondroitin sulfate (Bioiberica batch # 18/11/99) orally daily for 14 days beginning 7 days before the PC injection.

Group C (n=4) PC-injected intra-articularly in one knee joint and isotonic saline injected in the contralateral knee joint, administered 300 mg/kg (body weight) CaP orally daily for 14 days beginning 7 days before PC injection.

Group D (n=4) PC-injected intra-articularly in one knee joint and isotonic saline injected in the contralateral knee joint but animals administered 200 mg/kg (body weight) CaP orally daily for 14 days beginning 7 days before PC injection.

Group E (n=4) PC-injected intra-articularly in one knee joint and isotonic saline injected in the contralateral knee joint but animals administered with 100 mg/kg (body weight) CaP orally daily for 14 days beginning 7 days before PC injection.

After animals in groups B to E had received drug treatment for 7 days they were anaesthetised with halothane/nitrous oxide/oxygen (2:1:2; flow rates for $O_2$ and $N_2O$=1 and 2 liters/minute respectively). Each animal was under anaesthetic for at least 5 minutes before intra-articular injection and for a total of 10 minutes thereafter. Animals were given a single intra-articular injection of a preformed insoluble complex (PC) of poly-D-lysine (7.5 mg) and hyaluronan (HA) (7.5 mg) in 1 mL sterile, pyrogen-free isotonic saline in one knee. This preparation was prepared immediately prior to injection by quickly mixing 0.5 mL sterile 15 mg HA/mL with 0.5 mL sterile poly-D-lysine/mL in a 2 mL sterile syringe. The contralateral knee joint of each animal was injected with 1 mL sterile isotonic saline only to serve as an internal control. Animals in groups B to E continued to receive daily oral drug preparations for further 7 days post PC injection.

Seven days post arthritis induction, rabbits were anaesthetised with halothane/nitrous oxide/oxygen as before and blood (20-40 mL) was obtained directly from the heart using a sterile 14 gauge catheter and a 50 mL syringe. 10 mL of this blood was deposited into sterile glass EDTA ($K_3$) vacutainer tubes with a final dilution of 0.7% EDTA. A further 9 mL was added to 1 mL 5% (w/v) trisodium citrate and the remainder was added to serum tubes. Within 2 hours of blood collection the separation of mononuclear cells and neutrophils was performed using the centrifugation procedure as described below. All blood samples were kept at room temperature at all times.

Separation and Determination of Blood White Cells Numbers

The EDTA-containing blood collected as described above was used to prepare white cell fractions. 20 mL of Percoll (AMRAD Pharmacia, Boronia, Melbourne Australia) at a density range between 1.070-1.072 g/mL, was prepared in sterile 40 mL Sorvall centrifuge tubes. This optimum density was achieved by first adding 9 parts of neat Percoll to 1 part of sterile 1.5M NaCl. This stock solution was then diluted using 0.15M NaCl until the desired density was obtained.

Centrifugation of Percoll and Blood

The Percoll at an optimum density range of 1.070-1.072 g/mL, was centrifuged at 10,000×g for 20 minutes at room temperature, using a fixed angle rotor head in a Sorvall RC-5 centrifuge to form a gel which provides better separation of the white cells. 4 mL of the collected blood was then layered on top of the preformed density gradient and centrifuged at 1000×g for 20 minutes at room temperature using a swinging bucket rotor in a Beckman TJ-6 centrifuge. From each of the density vials 1-7 (AMRAD, Pharmacia) 40 μL was added to 3720 μL of sterile 0.15M NaCl to give a total volume of 4 mL. Each AMRAD vial contained coloured density marker beads of a given density. The density range of the 7 vials was 1.017-1.102 g/mL. The 4 mL density bead solution was then layered on top of a 20 mL preformed Percoll density gradient (1.07-1.072 g/ml), and centrifuged at 1000×g for 20 minutes at room temperature with the sample tubes prepared above, using a swinging bucket rotor in a Beckman TJ-6 centrifuge. This density marker tube served to calibrate the gradients formed in the sample tubes. The following density ranges were used for the rabbit's blood (these differ from the manufacturer's instruction for human blood):

1. Mononuclear cells: 1.04-1.06 g/mL
2. Neutrophils: 1.06-1.08 g/mL
3. Erythrocytes: 1.08-1.09 g/mL After centrifugation of each sample tube, mononuclear cells and neutrophils were separated by aspiration at their designated density range and placed into separate centrifuge tubes. These cells were washed twice with 3 volumes of 0.15M NaCl at 1000×g for 10 minutes at room temperature using a swinging bucket rotor in a Beckman TJ-6 centrifuge. The cell pellets of the mononuclear cells and neutrophils were resuspended with 500 μL PBS. From each cell suspension 50 μL was added to 50 μL of trypan blue solution and the cell numbers quantitated using a haemocytometer. From the mononuclear cells another 50 μL aliquot was used to form differential slides. This procedure allowed the percentage of neutrophils, lymphocytes and monocytes to be determined. Smears were formed using a Cytospin centrifuge.

Dissection and Collection of Synovial Membrane from Joints for Cell Culture

Joints were sprayed liberally with 70% (v/v) ethanol and placed in a clean plastic bag at 4° C. for transport to the sterile environment of a laminar flow cabinet. Using rat-toothed forceps and a no. 22 scalpel blade, the tendons and excess muscle tissue were removed from the joints without opening the capsule.

Using small rat-toothed forceps and no.11 scalpel blade the joint capsule was opened aseptically using a posterior approach, severing the posterior insertions of the cruciate ligaments to allow dis-articulation. The patella and the attached suprapatella mound of synovium was removed whole using a no. 11 blade. This tissue was then placed in a labelled specimen container filled with 10% (v/v) neutral buffered formaldehyde for histological processing. The remaining synovia was then harvested by excising pieces of the joint lining with the small rat-toothed forceps and discection with a no.11 blade, avoiding inclusion of excessive subsynovial tissue. Collected pieces were then floated into a labelled petridish containing 10 mL sterile PBS.

Synovial Fibroblast Isolation

The synovia in the petridish was diced finely then transferred to a 15 mL sterile centrifuge tube, using a sterile plastic transfer pipette with the fine end cut off (using a sterile no. 22 blade). The tubes were centrifuged at 1500-2000 rpm at 20° C. for 10 minutes and the cell pellet resuspended in 5 mL sterile T&E [0.2% (w/v) trypsin/0.1% (w/v) EDTA in PBS]. The tubes were placed at 4° C. overnight (cold trypsinisation) then were incubated at 37° C. for one hour. After incubation 5 mL DMEM/10% FCS was added (to inactivate the trypsin) and then the tubes were recentrifuged at 20° C., 2000 rpm for 10 minutes and trypsin/FCS solution between the pellet and floating fat layer was removed. Sterile DMEM/10% FCS was added to a total volume of 10 mL and pellet was resuspended. The tubes were recentrifuged at 20° C., 2000 rpm for 10 minutes. The DMEM/10% FCS solution was removed and the pellet was resuspended in 2 mg/mL collagenase in DMEM/10% FCS. The tubes were placed in the incubator at 37° C. for 3 hours then the collagenase solution, including fat layer, was removed to waste. Sediment pellet was resuspended in 10 mL DMEM/10% FCS using a sterile plastic transfer pipette. Two×5 mL aliquots of the cell suspension were placed into 2×25 $cm^2$ tissue culture flasks and incubated at 37° C. Media routinely was changed every two or three days. When one of the flasks was ~90% confluent it was used to determine HA synthesis. When the other flask was confluent, the cells were subcultured.

In Vitro HA Biosynthesis by Synovial Fibroblast

Synovial fibroblasts as prepared above were plated into 6 well plates at 200,000 cells per well and allowed to attach for 24 hours. To each well was added 2 mL DMEM+10% (v/v) FBS followed by 3H-glucosamine (stock is 1 µCi per microliter) and plates incubated for 24 hours. After which, flasks were removed from the incubator and chilled at 4° C. and media was removed to labelled 15 mL centrifuge tubes. As media was removed, each flask was twice gently washed with 0.5 mL nonsterile PBS twice, which was added to the same labelled 15 mL centrifuge tube. After the PBS rinse, 1 mL T+E was added directly to the cell layer in each well. The plate was incubated at 37° C. for 10 minutes. The released cell suspensions were transferred to labelled 5 mL tubes, rinsing the flasks twice with 0.5 mL papain buffer and adding the rinses to the same tubes.

Determination of Radiolabelled HA Synthesised by Cells

Two×0.5 mL aliquots of each media sample were labelled A and B. To all aliquots were added 20 µL 1M acetic acid (to adjust pH to approx. 4.0). To each sample labelled A was added 50 µL 20 mM sodium acetate/0.15M NaCl pH 6.0. To each sample labelled B was added 50 µL 20 mM sodium acetate/0.15M NaCl pH 6.0 containing 5 TRU *Streptomyces* hyaluronidase. (Sigma Chemical Co). All samples were incubated at 60° C. for 3 hours then boiled for 5 minutes to inactivate the *Streptomyces* hyaluronidase. Samples were then be stored at −20° C. prior to Superose 6 gel chromatography and determination of incorporated radioactivity into HA as already described above for the synthesis of HA by human synovial fibroblasts.

Immunohistology of Synovial Tissue

The patellae and suprapatella mound of synovium was removed whole from joints using the dissection procedure described above and the patellae and adhering synovium (and any pannus) sliced in half and each half placed in a specimen container with neutral buffered formalin. Processing and preparation of stained and unstained tissue sections were performed as already described above Immunolocaisation of Inducible Nitric Oxide Synthase (iNOS)

Four-micron patellae/synovium sections were deparaffinised to water. Endogenous peroxidase was blocked with 3% $H_2O_2$ for 5 minutes. A high temperature heat retrieval was used to unmask antigenic sites using 10 mM citrate buffer; pH 6.0. Non-specific binding was blocked with a serum-free protein block for 10 minutes. Sections were then incubated with the primary antibody polyclonal antiserum for iNOS (Cayman Chemicals Inc) 1:1000 overnight at 4° C. The negative control reagent used was a protein concentration matched non-immune rabbit serum. The detection system utilised a commercial avidin-biotin with horseradish peroxidase as an enzyme label (Dako Biologics Pty Ltd). The secondary antibody cocktail of biotinylated goat anti-rabbit and biotinylated goat anti-mouse (Dako Biologics Pty Ltd) was applied for 15 minutes at room temperature. Slides were then incubated for 15 minutes in a streptavidin conjugated to peroxidase (Dako Biologics Pty Ltd). Peroxidase activity was detected using 3,3'-diaminobenzidine (DAB). Sections were counterstained with Mayer's haematoxylin for 1 minute, dehydrated, cleared in xylene and mounted in Euckitt.

Immunolocaisation of Nitro-Tyrosine

The method used was identical to that described by Kobayashi et al (2001) for rabbit cartilages in another arthritis model (Kobayashi K, et al., Chondrocyte apoptosis and regional differential expression of nitric oxide in the medial meniscus following partial meniscectomy. J Orthopaedic Res, 2001,19; 802-808).

Statistical Methods

Differences between PC and saline injected joint data were assessed using paired t-tests. Non-treated, drug treated and non-drug treated PC or saline joint data were compared on each day using unpaired t-tests. Histological scoring (nonparametric data) was analysed using Wilcoxon signed rank tests. Analyses were performed using Microsoft Excel 98 or Statview 5.0 on an Apple Macintosh PowerPC. P values less than 0.05 were considered to be significant.

Results and Discussion

The present inventors have made the unexpected and surprising discovery that subjecting cartilage particles to autolysis in aqueous buffers maintained within the pH range of 4.0-7.0, particularly 4.5, at 37° C. for periods up to 36 hours, particularly 16 or 24 hours specifically released GAG-peptide complexes and matrix derived polypeptides into solution while leaving the tissue cells and their intracellular macromolecular components essentially in tact. In this context we used DNA as a marker for intracellular macromolecular components and demonstrated that the autolysis medium obtained by the present invention was substantially free of DNA. Moreover, these released GAG-peptide complexes, defined arbitrarily as Peptacans when used alone or in combination with other co-released polypeptides are pharmacologically more active than commercially available ChS.

The release of these cartilage products was found to be more rapid with smaller particles than larger ones (FIG. 1). However, when either cartilage was incubated at 37° C. over a 24 hour period 75-83% of the total tissue sulfated GAGs was released into solution as shown by analysis for this component irrespective of the particle size (FIG. 1).

Figure 2:
Figure 2:
Figure 2:
Figure 2:

The efficiency and selectivity of this method was also confirmed by histochemical analysis of the cartilage particles before and after subjecting them to the inventive method. FIG. 2 shows photomicrographs of histological sections of 3 mm bovine tracheal cartilage powders particles before and after subjecting them to the autolysis procedure using 100 mM calcium acetate buffer, pH 4.5 at 37 degrees C. Panels A and C are sections of cartilage before autolytic processing and B and D after. Panels A and B show the results of staining with Toluidine Blue (TB), a dye which binds to glycosaminoglycans (GAGs) while C and D show sections stained with Masson Trichrome (Masson TC), a dye known to stain native collagen fibres magenta colour. Note the loss of staining for GAGs in section B after autolysis but a slightly increased intensity of staining for collagen following the removal of the majority of GAGs as shown in D. Cell nuclei, identified in these sections by the green counterstains are clearly unchanged by the autolytic process. All sections are shown at magnification ×400.

As is evident from FIG. 2 the level of staining for the presence of sulfated GAGs in cartilage particles using the cationic stain for these molecules, Toluidine Blue, before processing was extensive but after incubation was diminished. On the other hand, Masson Trichrome staining of native collagen fibres was essentially unchanged by the autolytic process (FIG. 2). Significantly, the cells and importantly their nuclei which were clearly visible using both staining procedures of the residual cartilage, remaining after removing the supernatant and washing with the incubation buffer, were observed to be largely undisturbed (FIG. 2).

Figure 3:
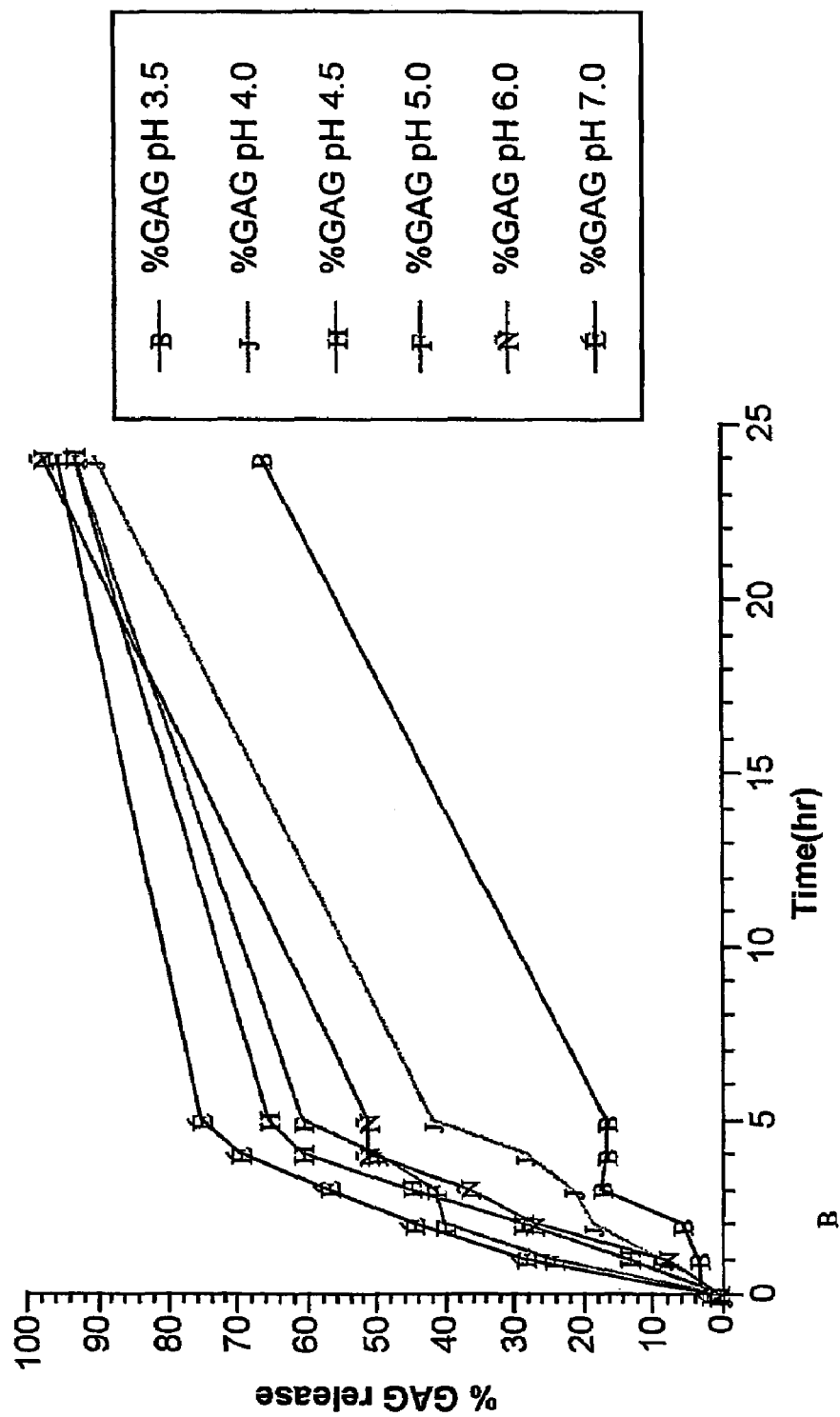
Figure 4:
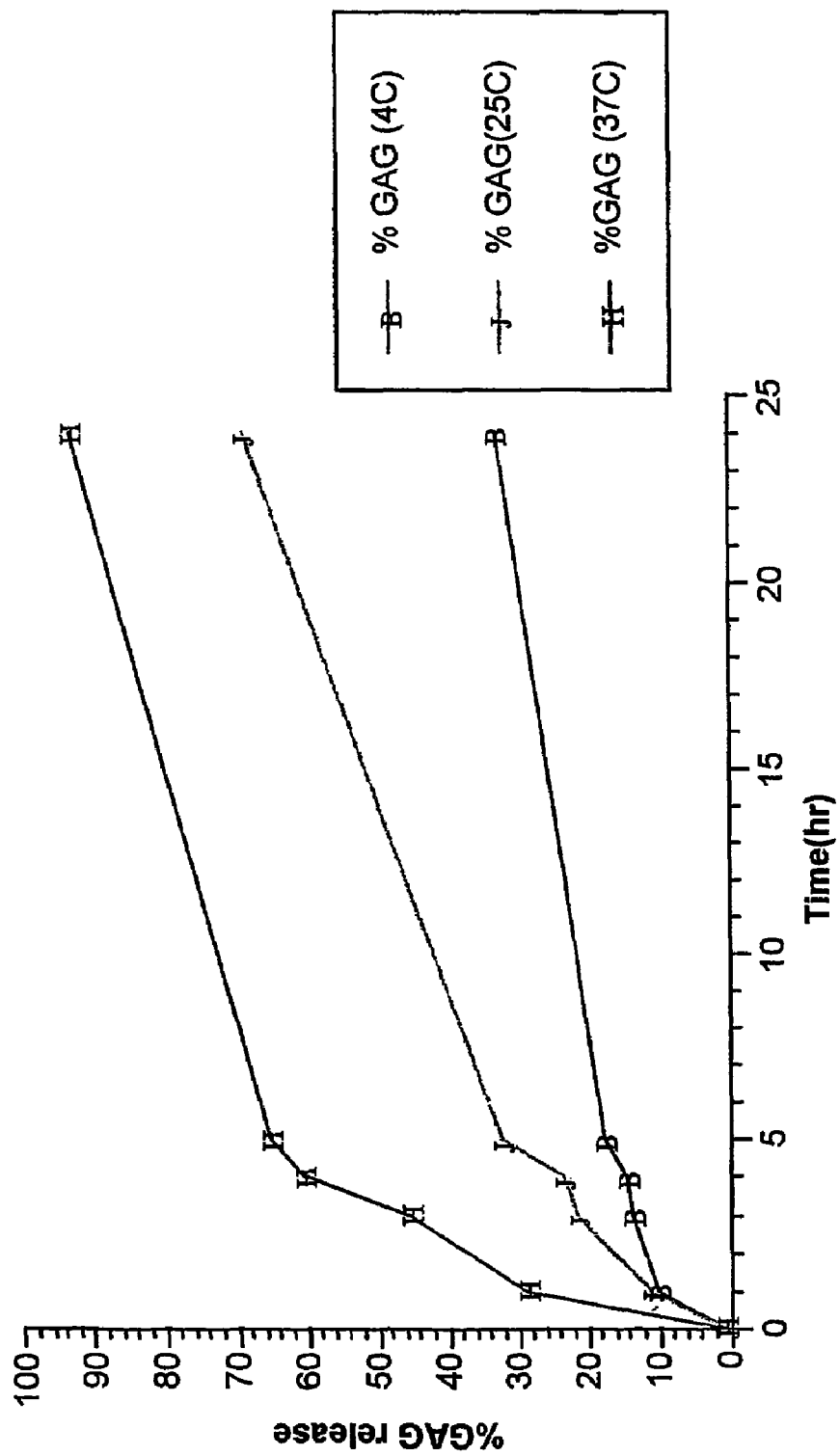
Figure 5:
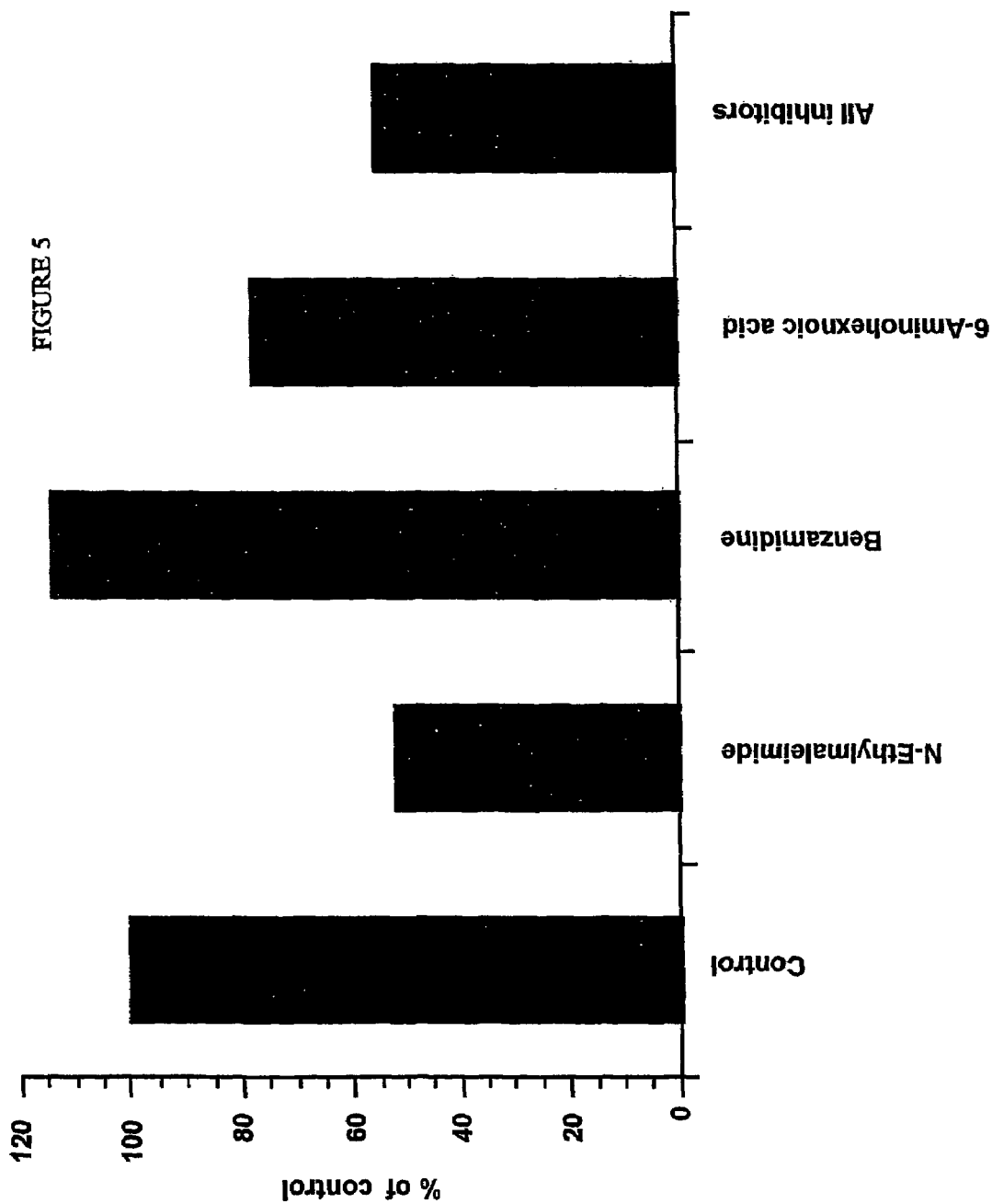

The autolytic process was affected by both pH and temperature. As is evident from FIG. 3 the most rapid release of peptacans from bovine tracheal cartilage occurred within the pH range 4.0-7.0. The normal mammalian blood temperature of 37 degrees C. was found to be more effective than lower temperatures, most notably 4° C. in facilitating peptacan release while intermediate levels of release occurred at 25 degrees C. (FIG. 4). The influence on this release process of both temperature and pH was consistent with the notion that autolysis was proceeding via the cleavage of matrix proteoglycans and other structural proteins by endogenous enzymes whose catalytic activities were optimum within the pH range 4.0-7.0 at 37 degrees C. This explanation was confirmed by the observation that the release process was substantially slowed by maintaining the cartilages particles in the autolysis buffers at 4° C. as well as the observation that the rate of release was markedly reduced by including specific inhibitors of proteinases in the incubations in buffers at 37 degrees C. (FIG. 5). As is evident from FIG. 5, approximately 50% inhibition of the autolytic process was achieved by the addition of the cysteine proteinase inhibitor, N-ethylmaleimide to the buffer solution. Since the major cysteine proteinases of cartilage are the Cathepsins (Dingle J T, The secretion of enzymes into the pericellular environment. Phil Trans Royal Soc (London), 1975, 271: 315-324; Barrett A J and McDonald J K, Mammalian Proteases, Academic Press, London, New York 1980, pp338-350; Barrett A J et al., Lysosomal cysteine proteinases, ISC Atlas Sci Biochemistry, 1988,1: 256-260, Muller-Ladner U, Gay R E, Gay S, Cysteine proteinases in arthritis and inflammation, Perspectives in Drug Discovery and Design, 1996, 6:87-98) which have pH optima between 3.5-6.0, it is most likely that these enzymes are largely responsible for the autolytic degradation of matrix components in this invention. However, as matrix component degradation was not completely abrogated by N-ethylmaleimide other classes of proteinases are clearly involved. Since the serine proteinase inhibitor, Benzamidine had no observable effect on release, this class of proteinases would seem to excluded. However, the matrix metalloproteinases (Birkedal Hansen H, et al., Matrix metalloproteinases: a review. Critical Rev Oral Bio Med. 1993, 197: 197-250) and aggrecanases (Ilic M Z C, Handley C J, Robinson H C, Mok M T, Mechanism of catabolism of aggrecan by articular cartilage, Arch Biochem Biophys, 1992, 294:115-122) which have previously been shown to degrade cartilage components at neutral pH are potential candidates.

As already discussed herein the matrix degradation products generated by these endogenous enzymes are structurally different from those produced by digesting connective tissue with papain or proteinases of other origins. Since the pharmacological activity of drugs and biopharmaceuticals is critically dependent on their composition and structure, we consider that the peptacans and the other autolytic products generated by the present inventive method cannot be reproduced by simply digesting cartilages with exogenous enzymes such as papain, chymopapain, bromolein, pepsin, trypsin, chymotrypsin, elastase or other enzymes which are not specifically derived from the tissues themselves.

The efficiency of the autolytic process in the present invention was also influenced by the animal species and anatomical location from where the cartilage was derived. As is evident from TABLE 1 below, bovine tracheal and nasal cartilages afforded the highest yields of peptacans when incubated at 37° C. over 24 hours. However, deer antler cartilages and avian (chicken) sterna provided more than 60% yield of peptacans under the same conditions. Surprisingly, commercially available samples of shark cartilage, of unknown location or method of preparation afforded very low yields of peptacans. Nevertheless, it is clear from these examples that the method of the invention is applicable to a wide range of connective tissues but the efficiency of release of peptacans into the aqueous medium is related to their ultrastructural assembly and means of preparation prior to autolytic treatment.

TABLE 1

Kinetics of sulfated glycosaminoglycan (GAG) release from cartilages of various origins over 24 hours using 100 mM Calcium Acetate buffer pH 4.5.

| Time | % GAG released | | | | | | | |
|---|---|---|---|---|---|---|---|---|
| (hr) | (B-Tracheal) | (A-Sternea) | (B-Nasal) | (Shark) | (O-Articular) | (O-Meniscus) | (C-Antler-tip) | (C-Antler-mid) |
| 0 | 0.54 | 2.91 | 0.08 | 6.67 | 1.13 | 0.00 | 0.05 | 0.00 |
| 1 | 13.26 | 41.55 | 10.64 | 30.50 | 3.38 | 0.00 | 13.10 | 5.18 |
| 2 | 28.96 | 41.97 | 28.86 | 30.73 | 7.22 | 0.00 | 27.90 | 19.42 |
| 3 | 45.36 | 46.26 | 42.09 | 27.28 | 13.96 | 0.06 | 58.09 | 42.40 |
| 4 | 60.75 | 48.75 | 50.51 | 24.95 | 17.97 | 0.10 | 66.06 | 56.63 |
| 5 | 65.61 | 45.71 | 52.14 | 24.95 | 18.57 | 0.38 | 62.64 | 56.45 |
| 24 | 93.16 | 60.90 | 81.36 | 23.65 | 51.03 | 0.52 | 83.14 | 56.31 |

B = Bovine, A = Avian, O = Ovine, C = Cervine, Antler-mid = cartilage between tip and bone, Shark = unknown site.

Figure 6:
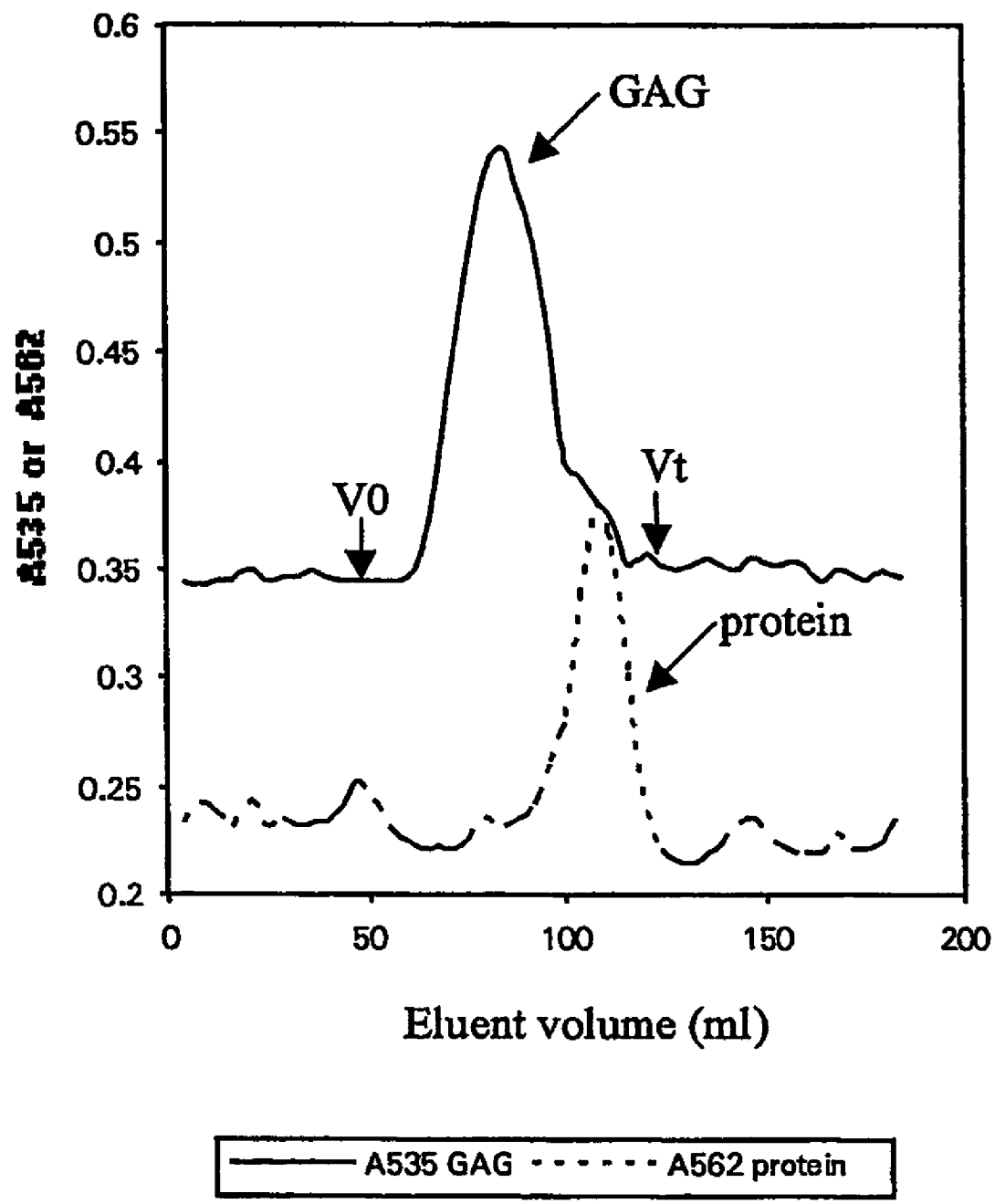
Figure 7:
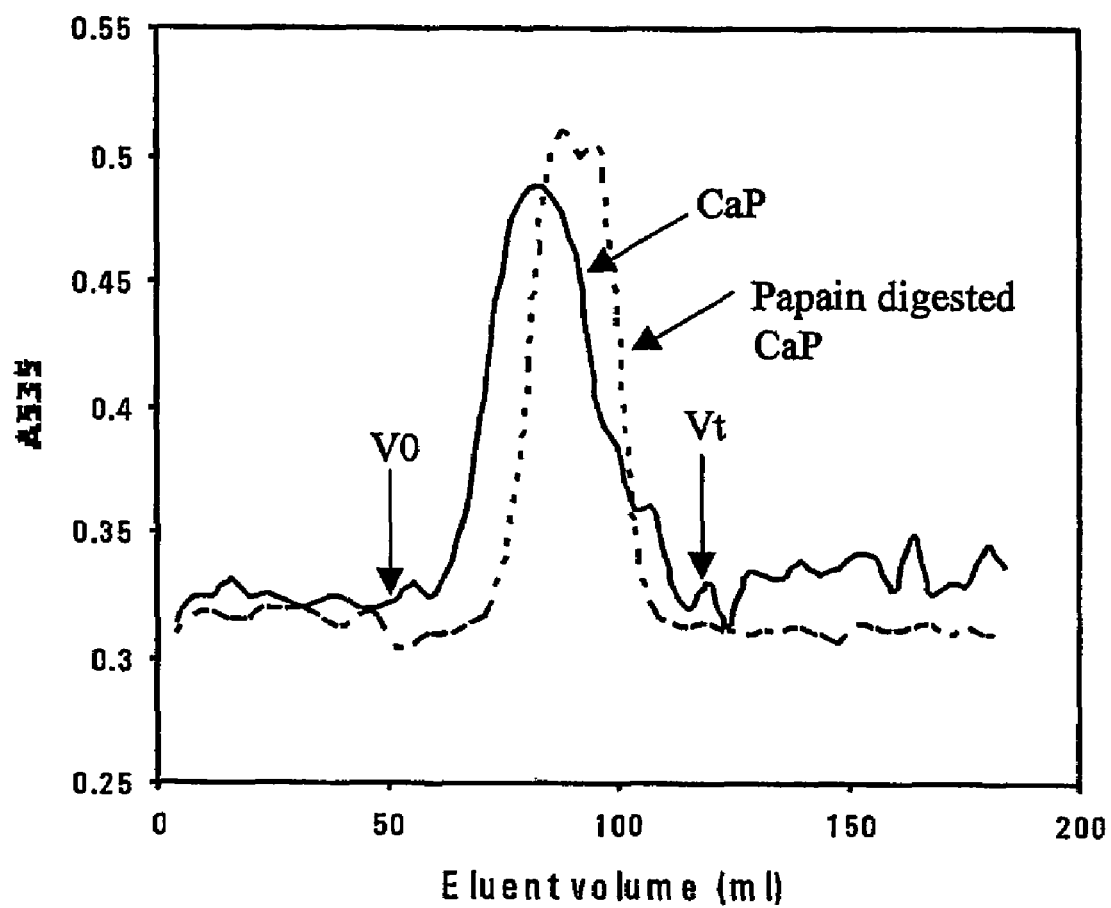
Figure 8:
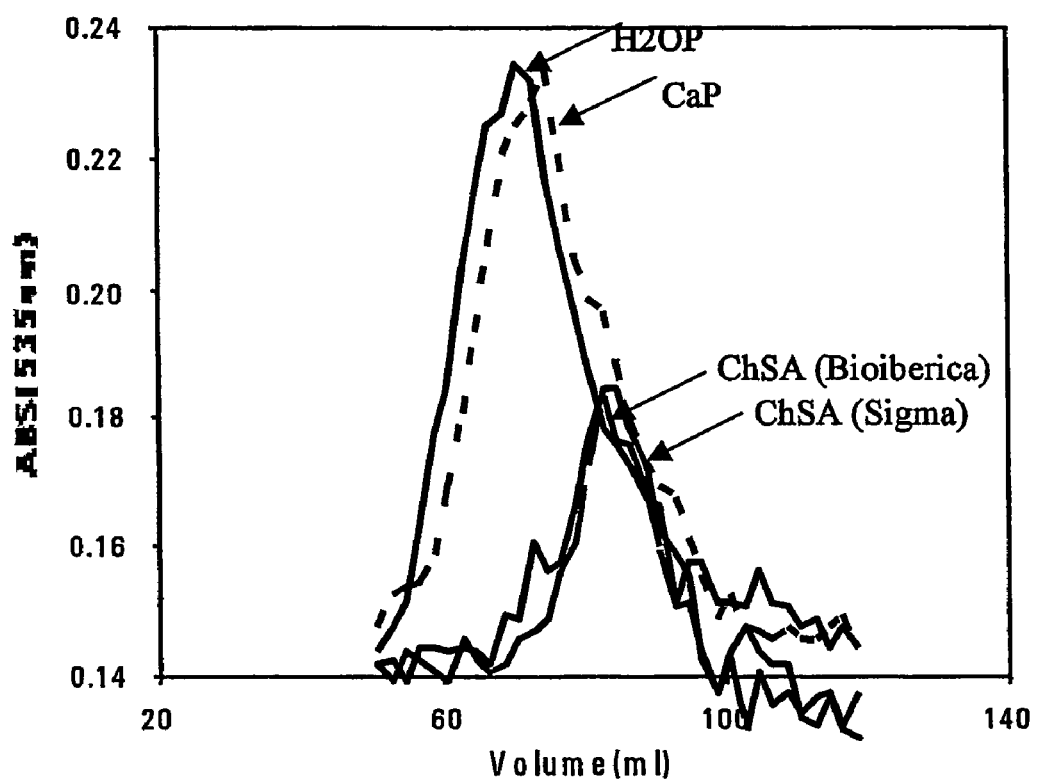
Figure 9:
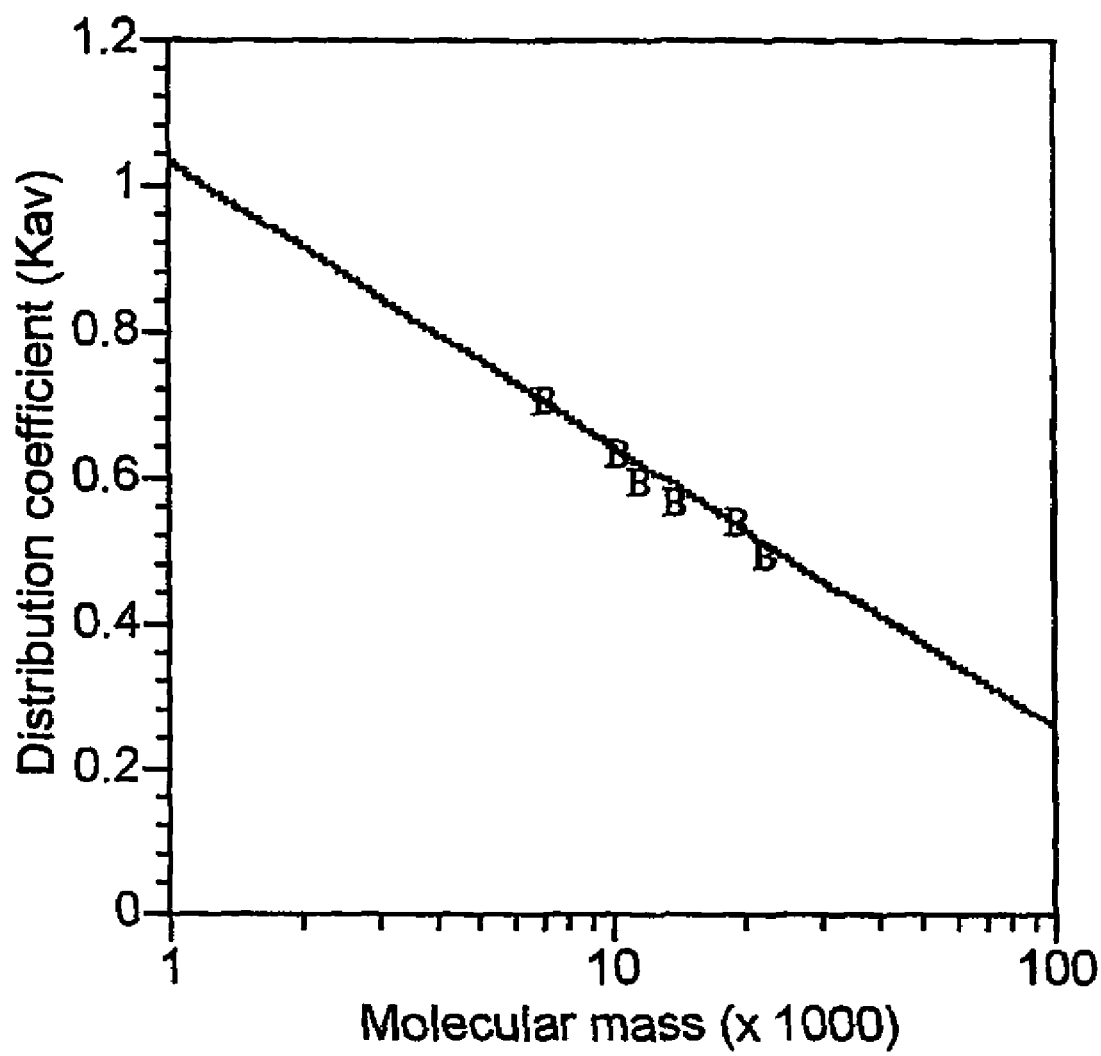

When the supernatants derived from the tracheal cartilage incubated with 0.1M Calcium Acetate were applied to a Superdex gel filtration column and fractions monitored for sulfated-GAGs and protein two resolved peaks corresponding to the GAG-peptide and polypeptides were obtained (FIG. 6). Evidence that the GAG-peptide was not simply ChS but contained more than one sulfated GAG chain was provided by its digestion with the proteolytic enzyme papain which shifted the DMMB positive peak to the same column factions obtained when pure ChS was chromatographed under the same conditions (FIG. 7). When the supernatants obtained from incubation of 0.1M Calcium acetate pH 4.5 (CaP) and dilute acetic acid pH 4.5 (H2OP) were chromatographed under the same conditions on the Superdex-200 column it was observed that the GAG-peptide obtained with the Calcium Acetate buffer was of smaller molecular size than that released by the acetic acid digestions. Both were, however larger than two commercially available ChSs (FIG. 8). The weight average molecular masses of the CaP, H2OP, purified CaP pCaP) and the two commercially available ChSs were then assessed using a Sephadex-G 200 high resolution gel exclusion column and seven ChS standards prepared and characterised previously (Melrose J and Ghosh P, Determination of the average molecular size of glycosaminoglycans by fast protein liquid chromatography. J Chromatography, 1993, 637; 91-95). The correlation between MW and Kav obtained using these ChS standards and the Sephadex column is shown in FIG. 9 and the results obtained for the unknown preparations is shown in TABLE 2 below. These experiments confirmed that the GAG-peptide in CaP contained 2 ChS chains while that in H2OP consisted of 3 ChS chains.

TABLE 2

Average Molecular Size [KDa] of commercial chondroitin sulfates and Peptacans as determined by Gel Chromatography and standards

| | |
|---|---|
| ChSA (Sigma) | 17.3 |
| ChSA (Bioiberica) | 20.0 |
| CaP | 33.7 |
| pCaP | 31.1 |
| H2OP | 46.1 |
| MgP | 32.3 |
| ZnP | 50.4 |

Figure 10:
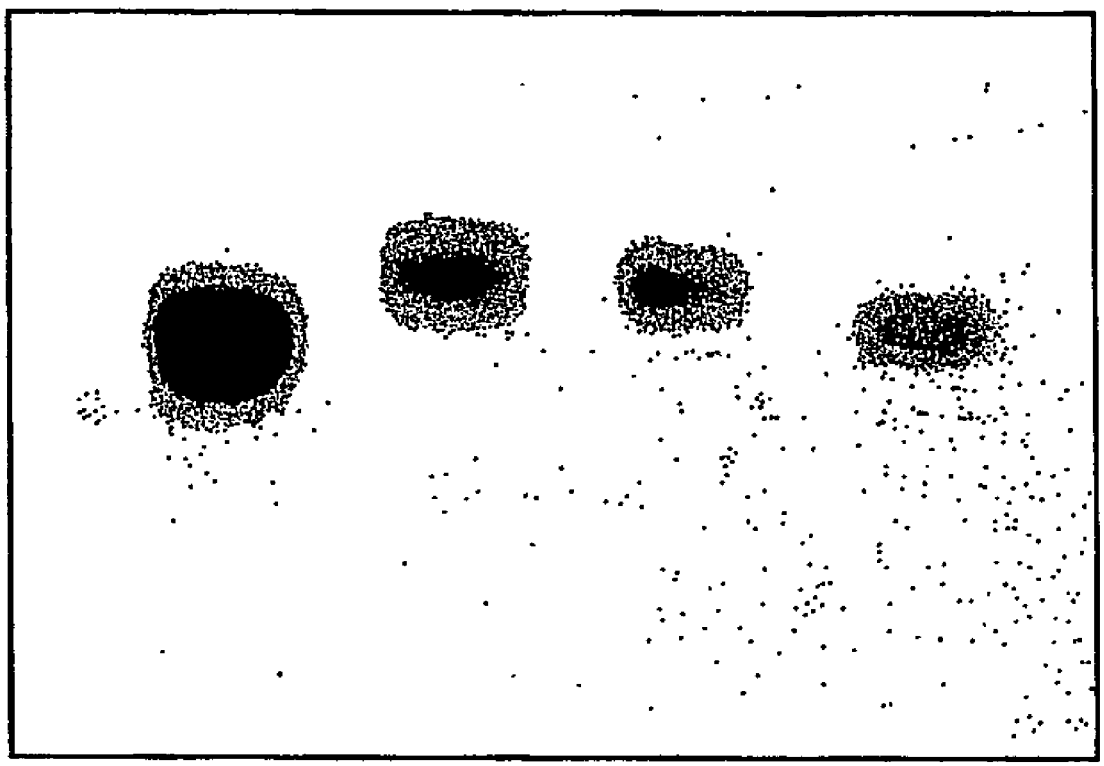
Figure 11:
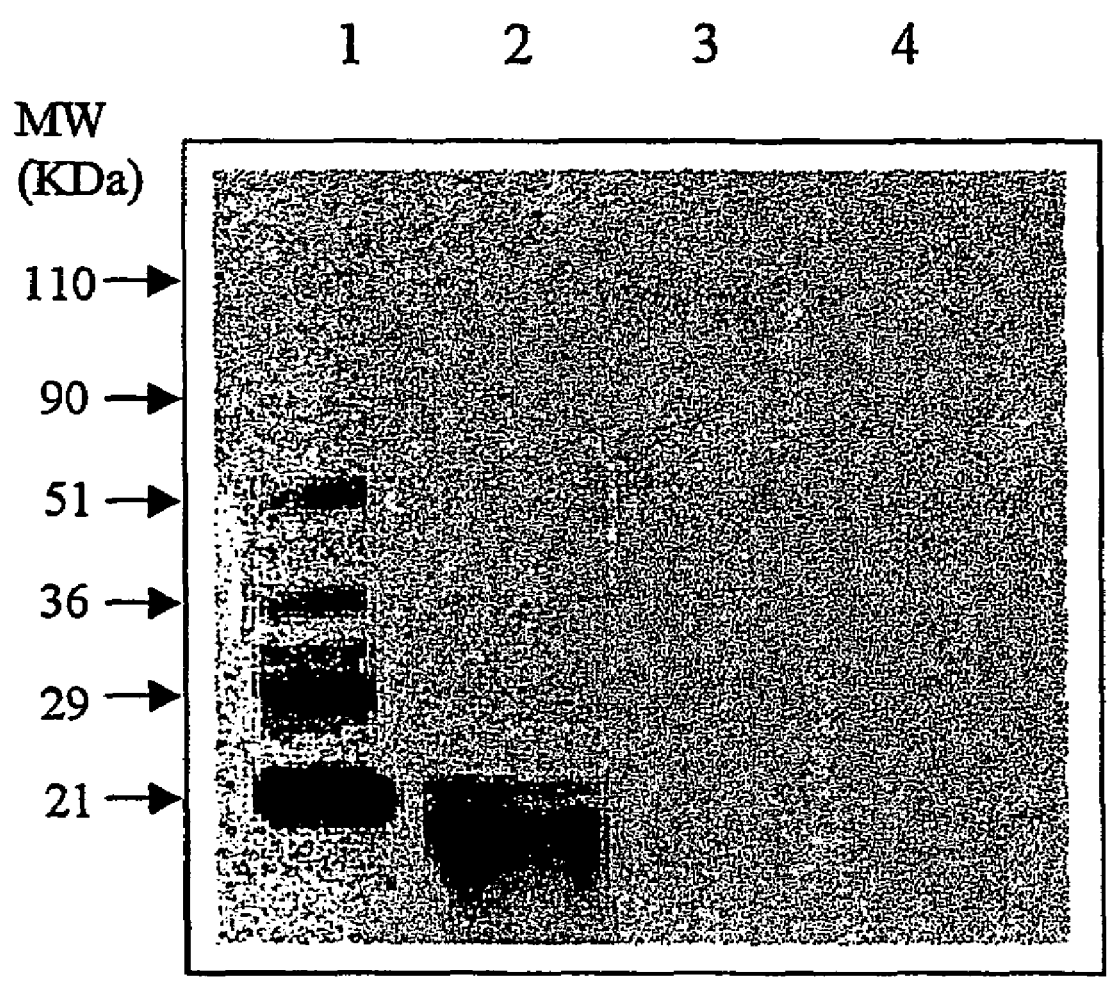

CAPAGE of CaP, pCaP and papain digested CaP indicated that the only sulfated GAG present was ChS (FIG. 10). However, SDS-PAGE showed that CaP also contained a number of peptides with MWs of 21 KDa or less which were not present in the purified CaP (FIG. 11). FIG. 11 shows analysis of proteins and peptides in Peptacans Using SDS-Polyacrylamide gel electrophorsis. Lane 1=protein markers with molecular weights shown, lane 2=CaP, lane 3=purified CaP, lane 4=chondroitinase-ABC digested and purified CaP.

Analysis for total protein and hydroxy proline content as a marker of collagen of these samples suggested that the dominant polypeptides released were largely derived from cleavage of collagen chains.

TABLE 3

Analysis of Peptacans and Commercial Chondroitin Sulfates For Sulfated Glycosaminoglycans, Protein and DNA content

| Samples | S-GAG(DMMB) % | Protein (BCA) % | DNA(Hoechst) % |
|---|---|---|---|
| ChSA (Sigma) | 98.5 | 0.16[a] | 0.36 |
| ChSA (Bb 1/0015, 05/2001) | 97.4 | 1.25[a] | 0.32 |
| ChSA (Bb 18/11/99) | 98.1 | 0.63[a] | 0.35 |
| ChSA (NaP) | 97.8 | 0.74[a] | UN |
| ChSA (CaP) | 96.5 | 1.40[a] | UN |
| CaP | 39.8 | 35.12[b] | UN |
| pCaP (EtOH ppt) | 49.0 | 40.51[b] | UN |
| H2OP | 65.6 | 44.48[b] | UN |
| NaP | 53.3 | 32.93[b] | UN |
| pH2OP (column) | 85.0 | 9.60[b] | UN |
| pCaP (column) | 44.8 | 6.52[b] | UN |
| MgP | 32.5 | 36.59[b] | UN |
| ZnP | 18.6 | 38.17[b] | UN |

Figure 12:
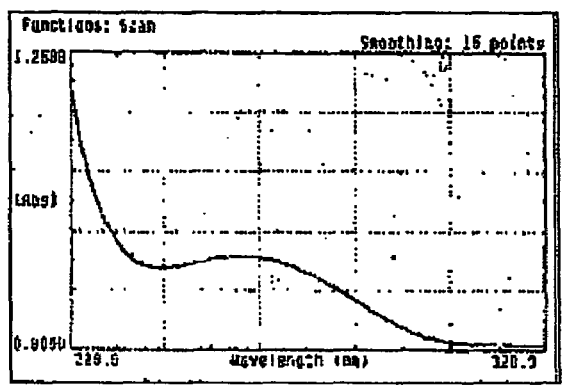
Figure 12:
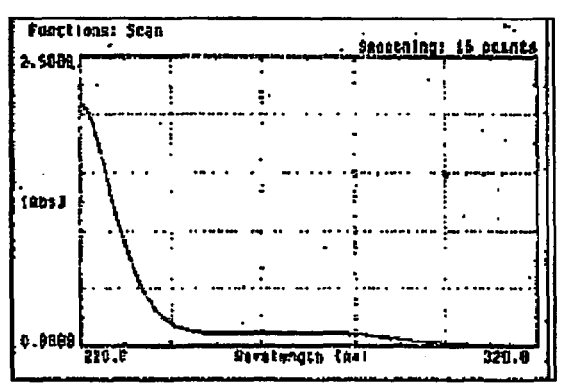
Figure 12:
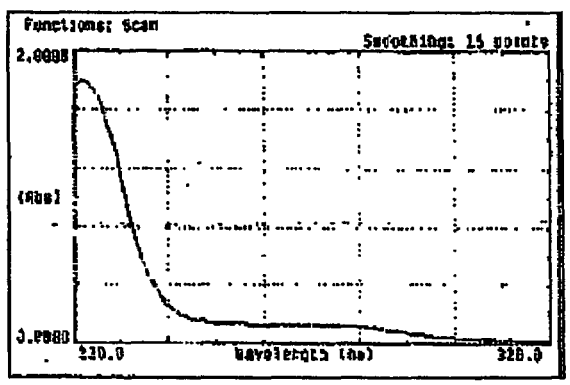
Figure 12:
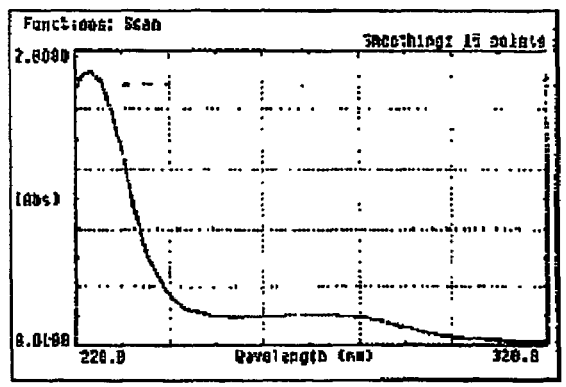
Figure 13:
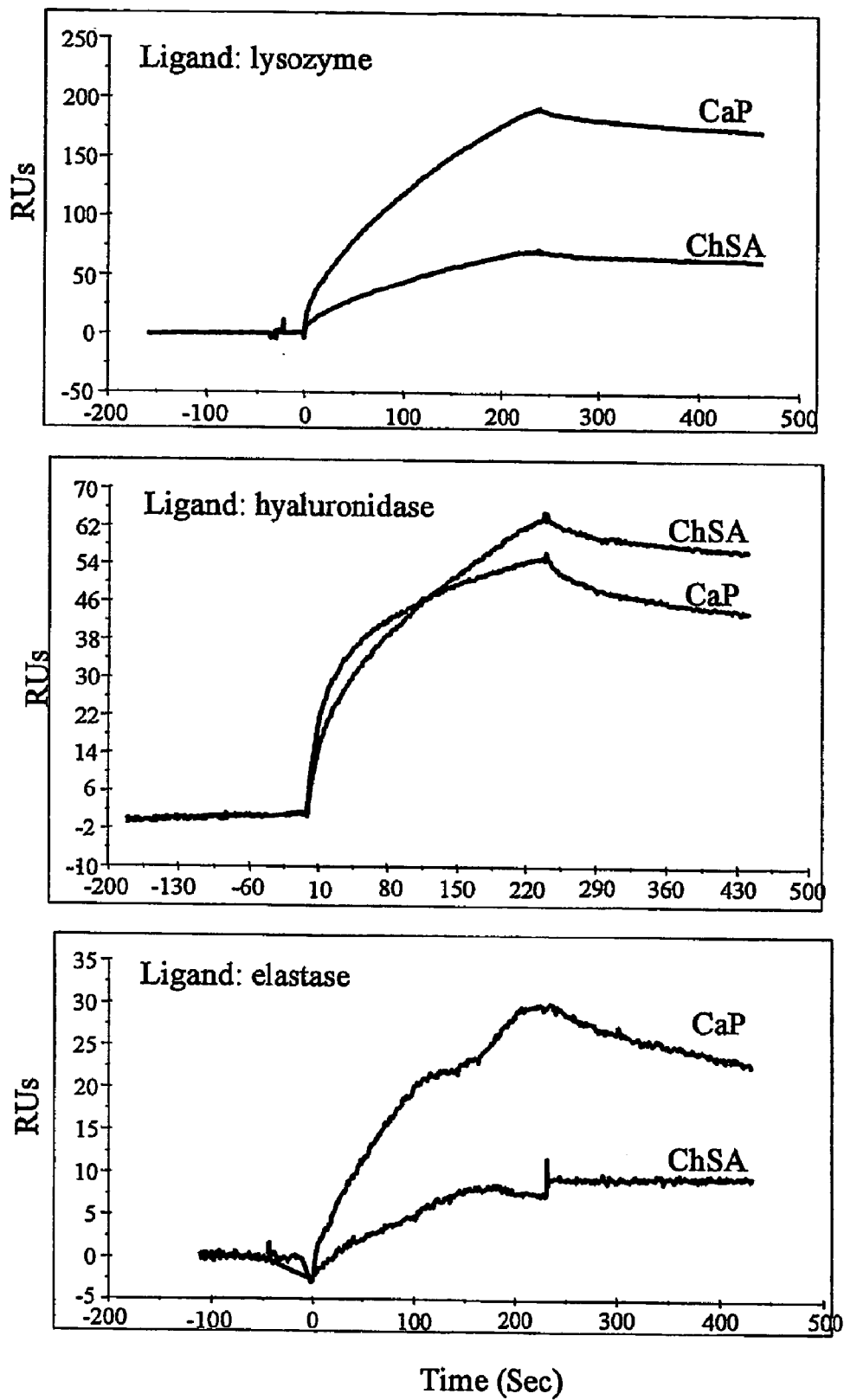

S-GAGs = sulfated glycosaminoglycans (method of assay used, see text)
UN = undetectable,
[a] using BSA as standard,
[b] using Gelatin as standard Spectroscopic analysis of concentrated aqueous solutions (1.0 mg/ml) of the Peptacans (CaP, NaP, H2OP) and commercial ChSs (FIG. 12) and ChSs derived from Peptacans revealed low absorption for protein at 280 nM and DNA at 260 nM for the Peptacans and the ChSs derived from them. In contrast high values for DNA were evident in the commercial ChS preparations as indicated by the ratios of A260/A280 in their uv spectra which were in the order of 1.85 or more (FIG. 12). Using a published fluorescent dye binding assay for DNA in the same samples and calf thymus DNA as a standard confirmed that the Peptacan preparations and the ChSs derived from them were substantially free of DNA, whereas the pharmaceutical quality commercial ChS examined contained approximately 0.3% DNA (TABLE 3). Analysis of the relative binding of CaP and ChS to the enzymes, lysozyme, hyaluronidase and human neutrophil elastase which are mediators of matrix destruction in arthritis using the BIAcore 2000 system showed that CaP interacted more strongly with lysozyme and elastase than ChS but with hyaluronidase there was little difference between the two preparations (FIG. 13). The higher binding affinity of CaP for the proteolytic enzyme, elastase derived from human neutrophils was confirmed using a conventional functional assay and the synthetic elastase substrate, succinyl-alanine-alanine-valine-nitroanilide (SAAVN). Using this assay system the concentration range of ChS which produced 50% inhibition of elastase (IC50) was found to be 4-5 micrograms/ml while the IC50 for the CaP preparation was between 1-3 micrograms/ml.

Figure 14:
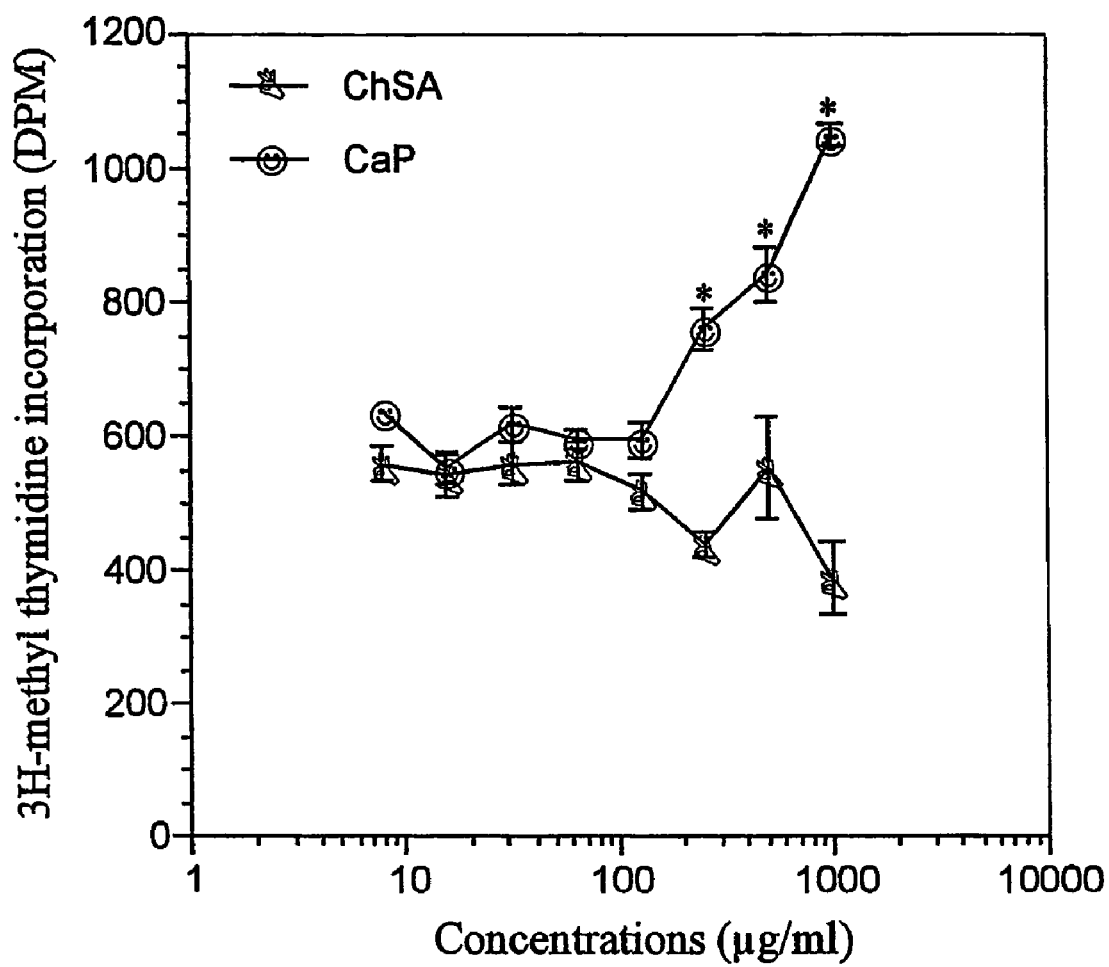
Figure 15:
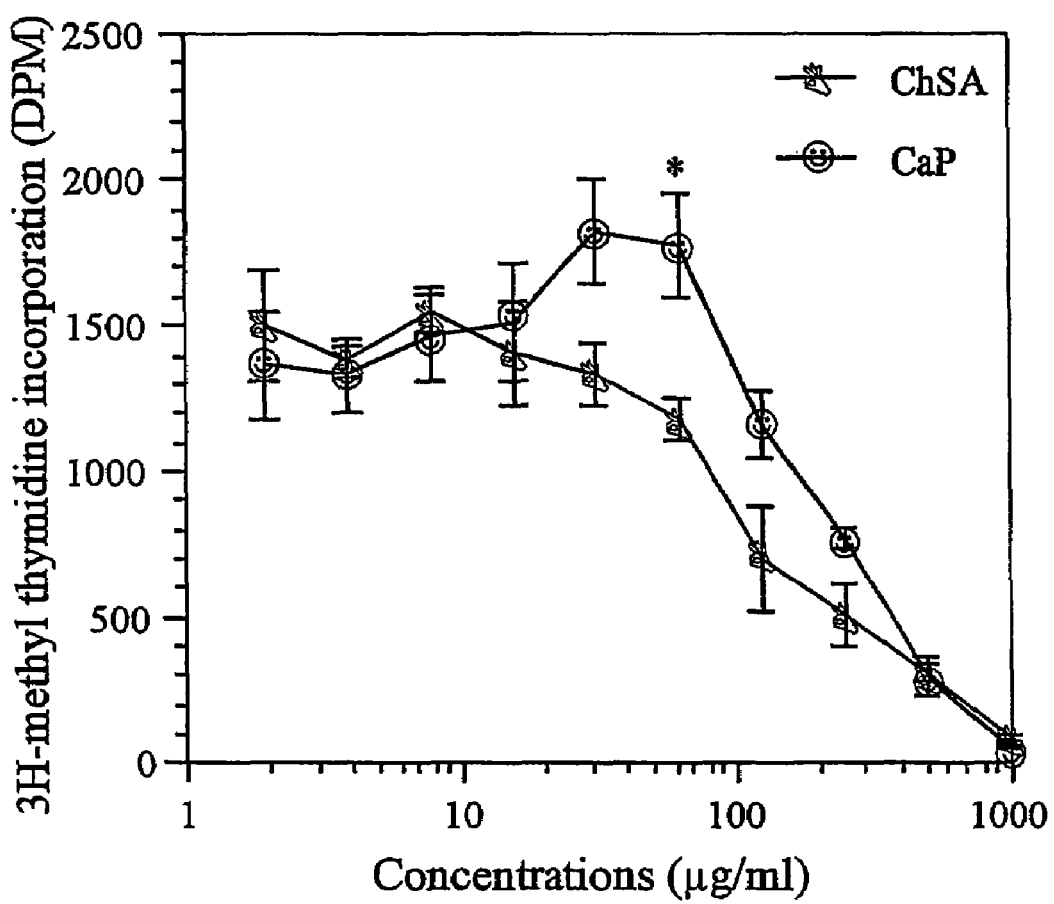

In the short term (2 days) chondrocyte cultures CaP at concentrations of 250 micrograms/ml and above stimulated cell division as indicated by tritiated thymidine incorporation into DNA while ChS had no effect (FIG. 14). In the longer term chondrocyte cultures (7 days) CaP at 62.5 micrograms/ml stimulated DNA synthesis (FIG. 15). These data clearly identify the anabolic effects of the CaP which would support the repair and regeneration of connective tissues.

As already indicated PGs are essential components of the cartilage extracellular matrix and are responsible for its unique biomechanical properties. Since these molecules are degraded and depleted from cartilage in arthritic joints, agents which can prevent this event or stimulate their biosynthesis by chondrocytes and other cells would be beneficial to the recovery of joint function and a reduction in patient symptoms.

Figure 16:
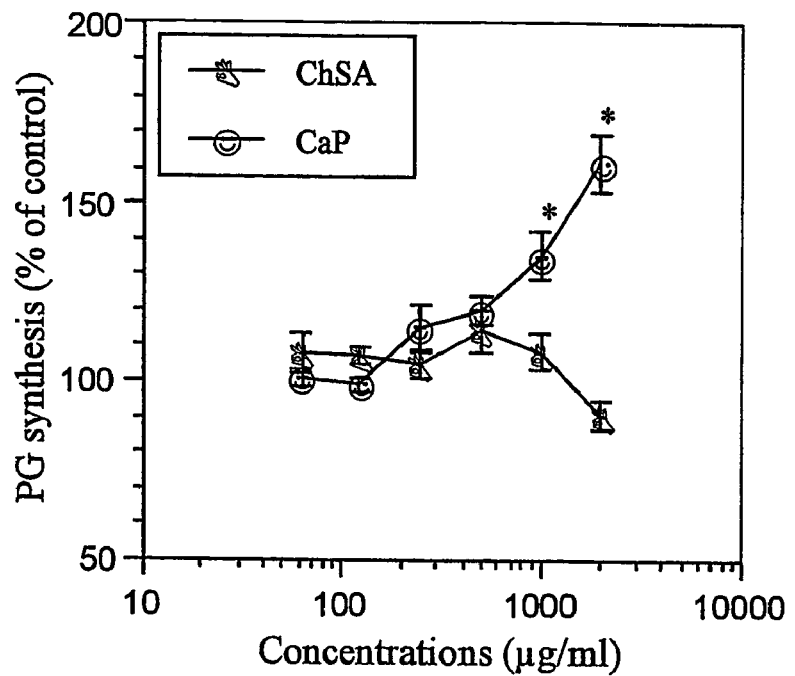
Figure 16:
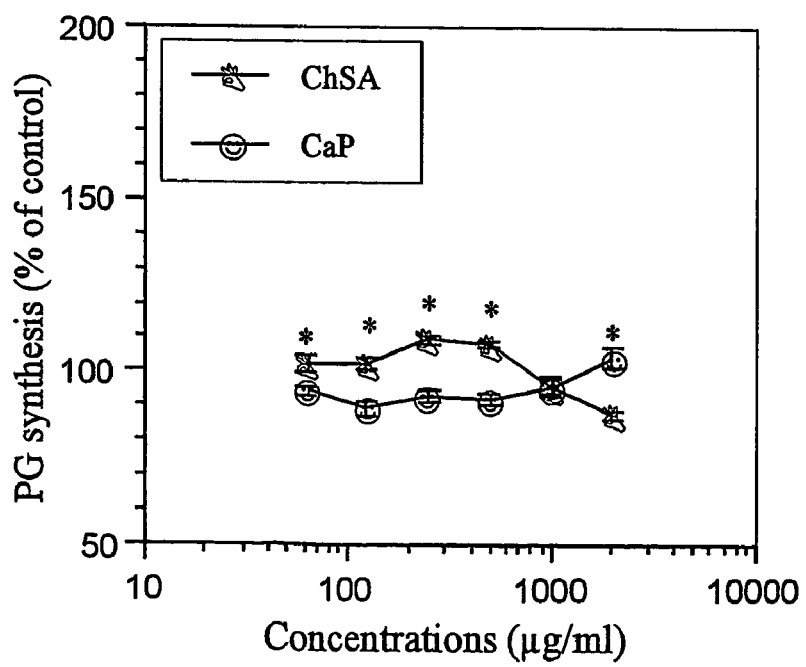
Figure 17:
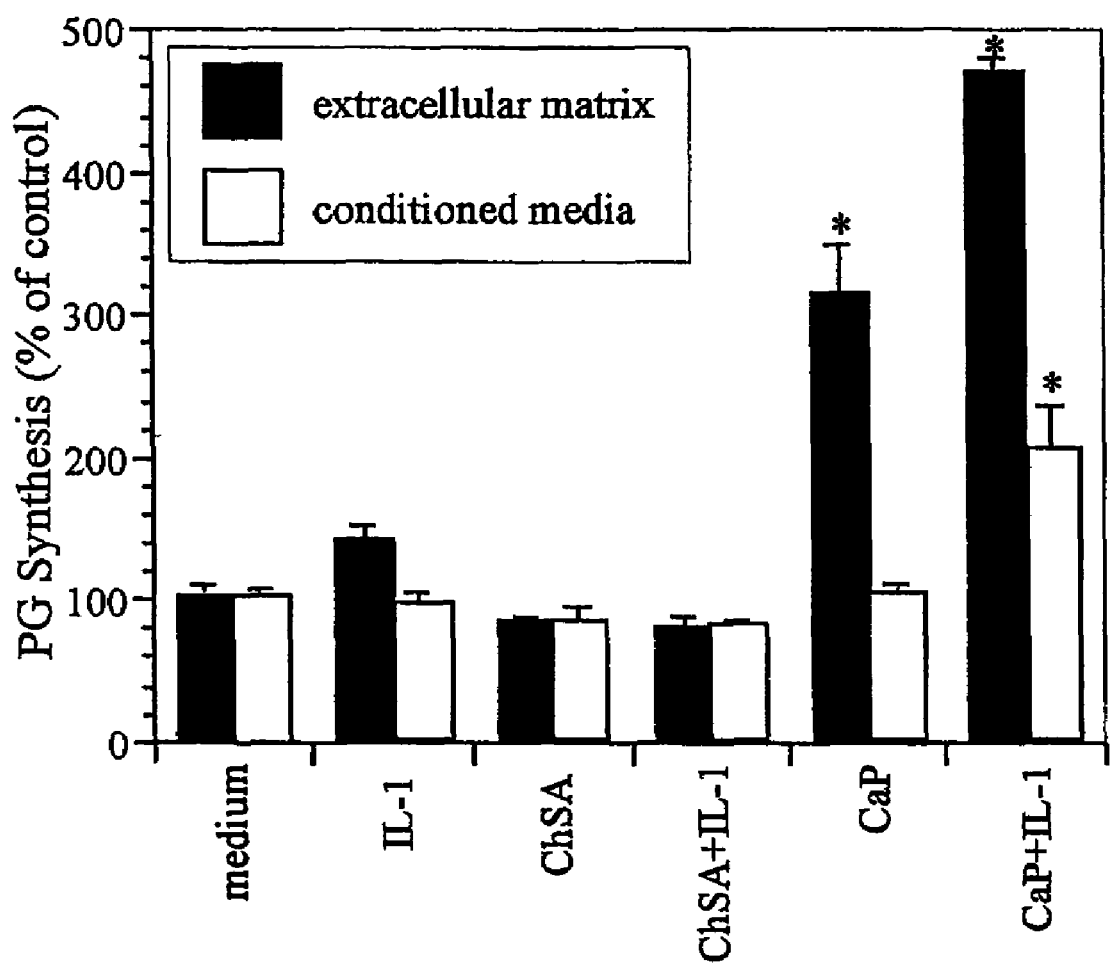

In contrast to ChS, CaP exhibited a concentration dependent stimulation of proteoglycan synthesis by chondrocytes with more than 150% deposition of PGs into the extracellular matrix at CaP concentrations of 1.0 and 2.0 mg/ml (FIG. 16). At concentrations between 62.5-500 micrograms/ml ChS released slightly more PGs into the media than CaP but this was reversed at 2.0 mg/ml. (FIG. 16). Significantly, when the effects of CaP and ChS on PG synthesis by chondrocytes was studied in cultures to which the proinflammatory cytokine interleukin-1 (IL-1) had been added CaP produced a 500% increase in synthesis at concentrations of 1.0 mg/ml while ChS had no effect (FIG. 17). Interestingly this stimulatory effect by CaP on PG synthesis was greater than when cells were cultured in the absence of IL-1 (FIG. 17).

Figure 18:
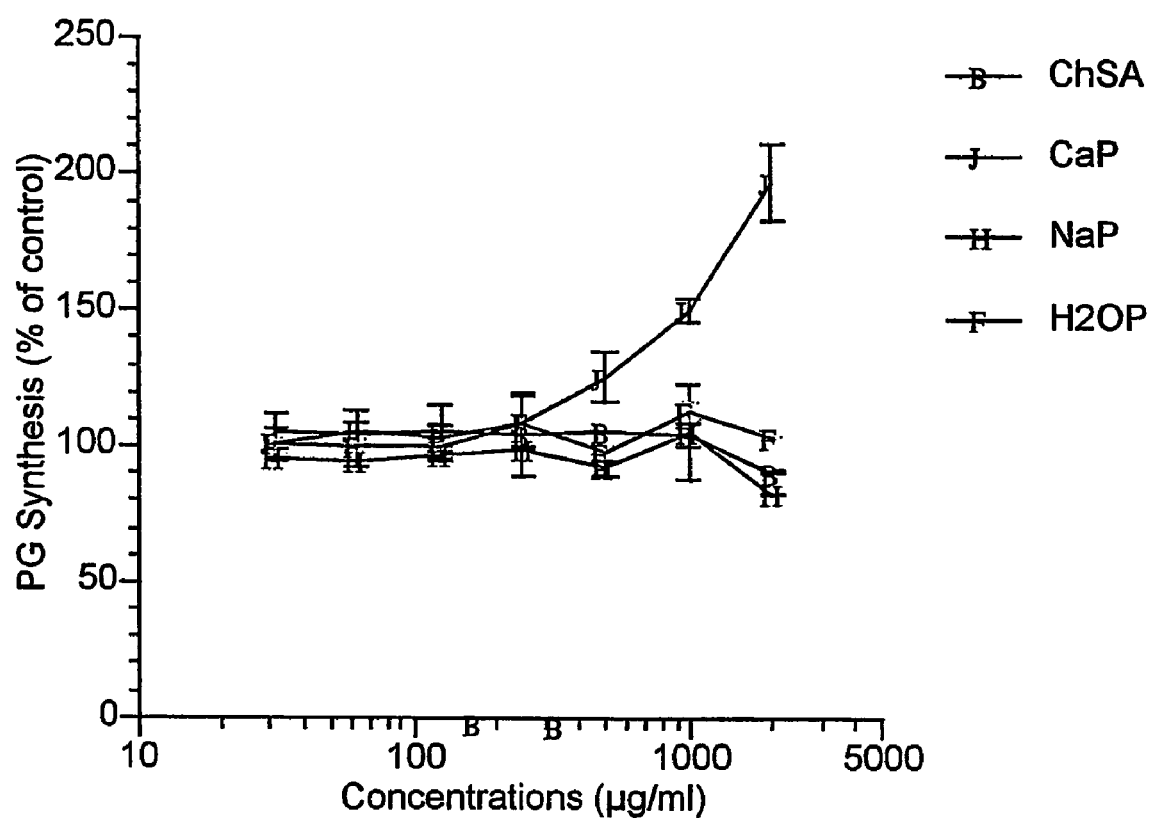
Figure 19:
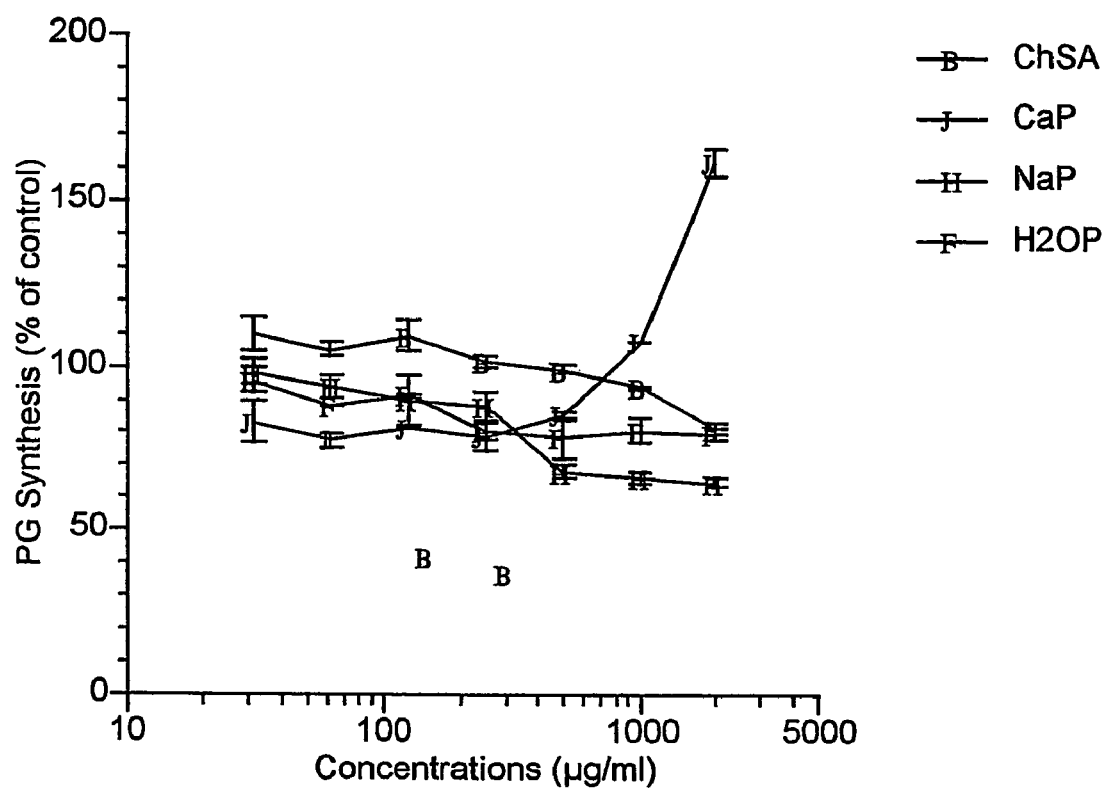
Figure 20:
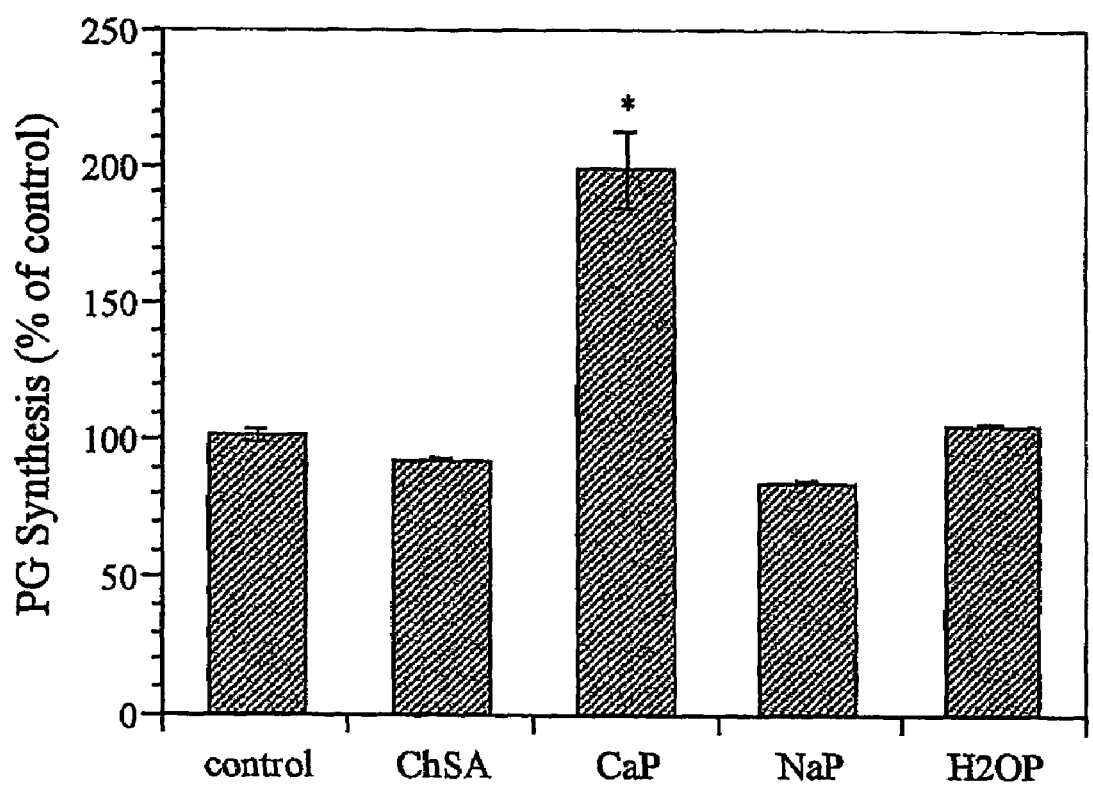
Figure 21:
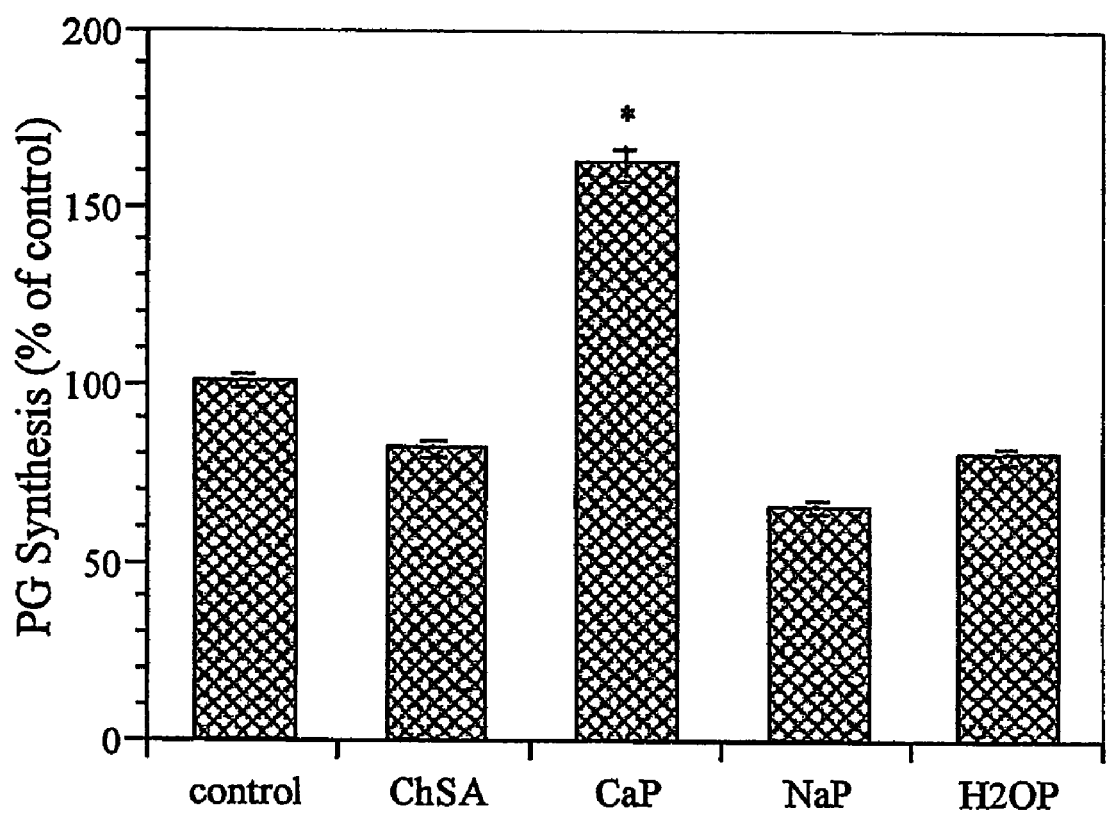
Figure 22:
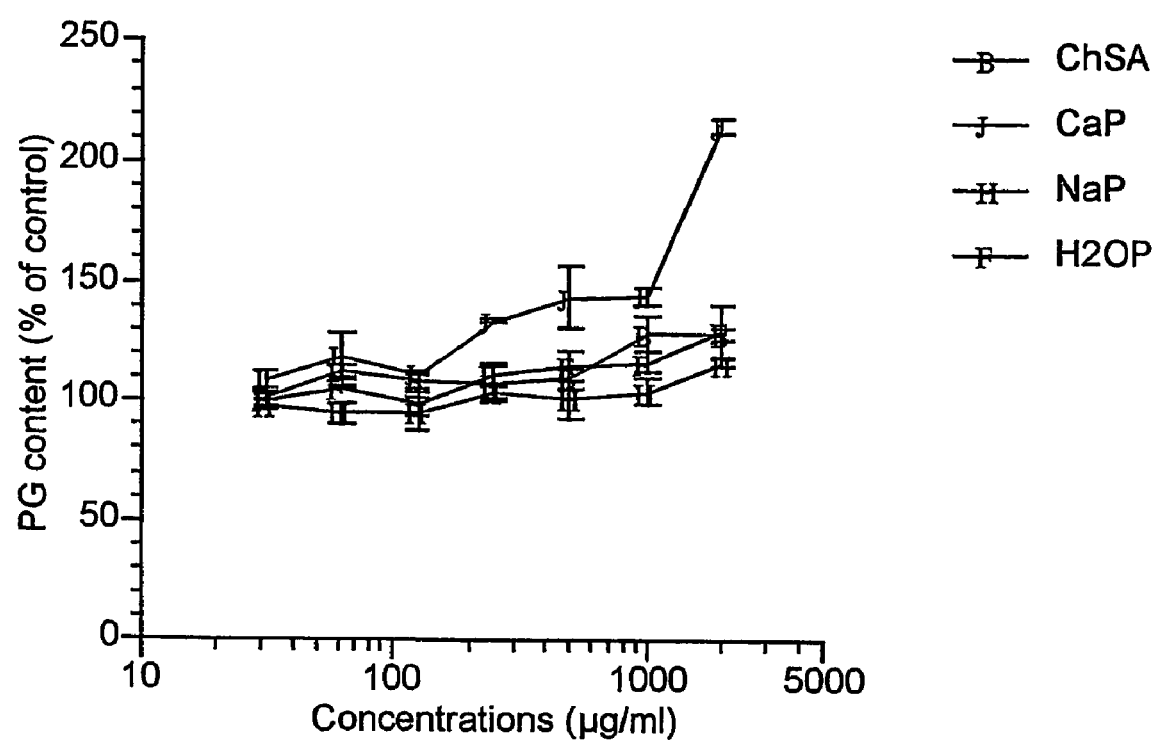
Figure 23:
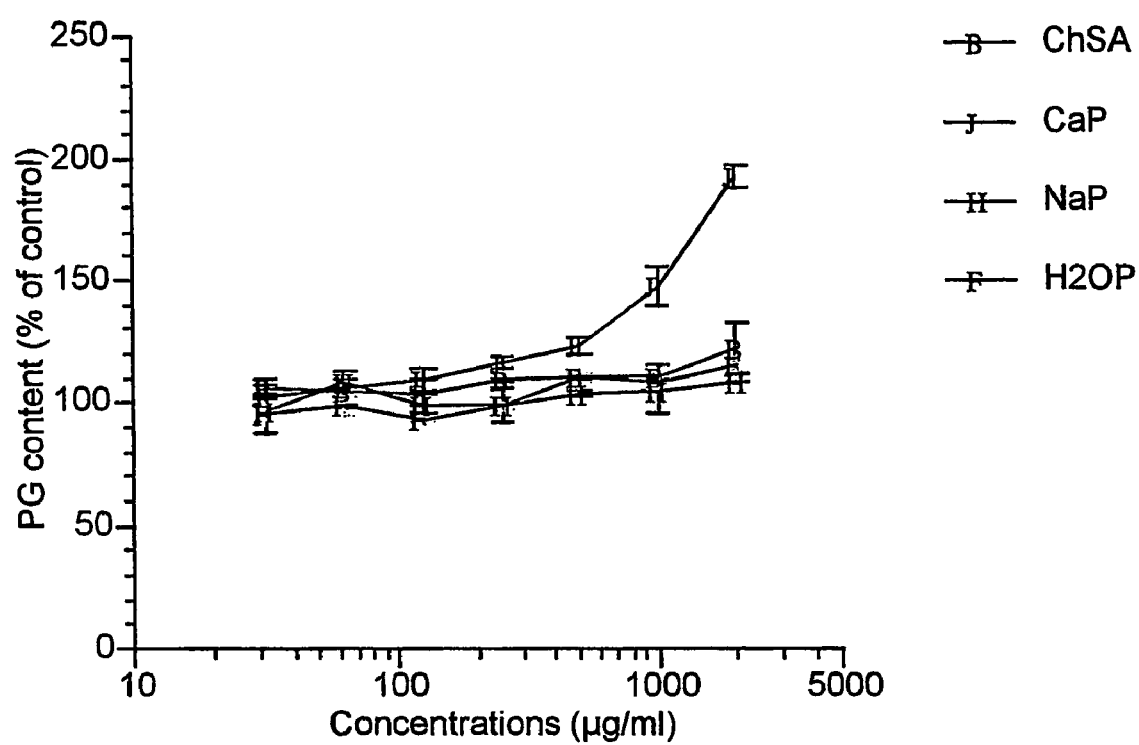
Figure 24:
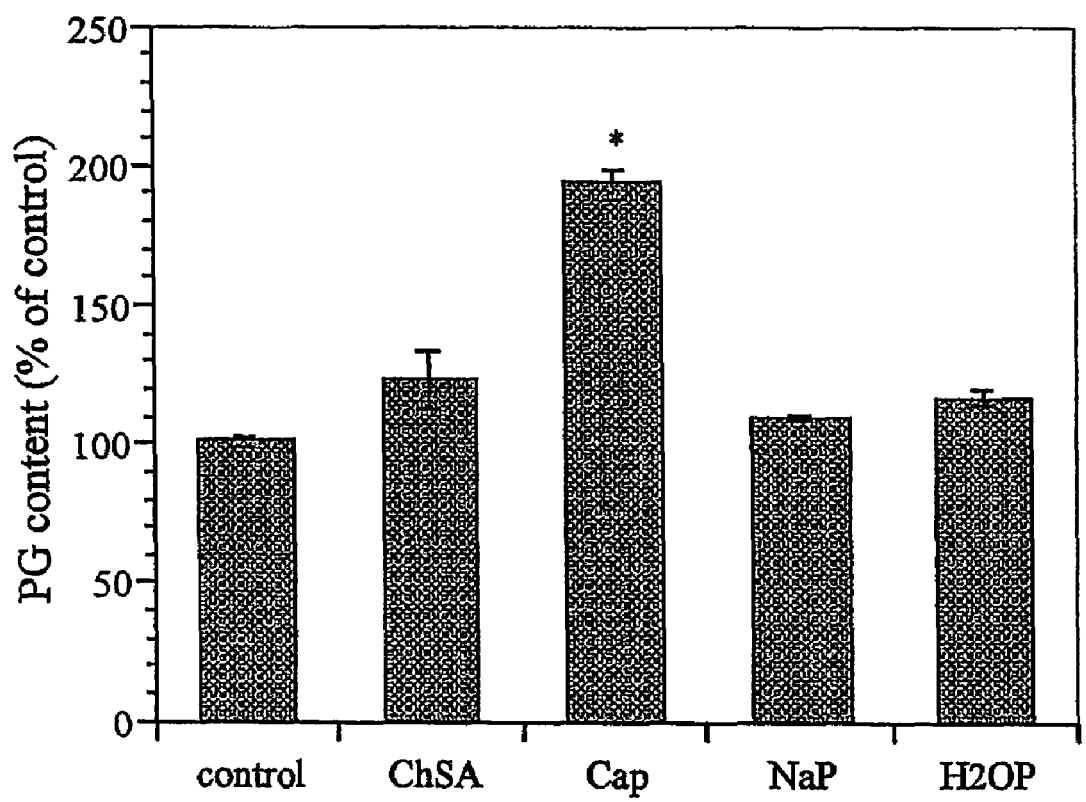
Figure 25:
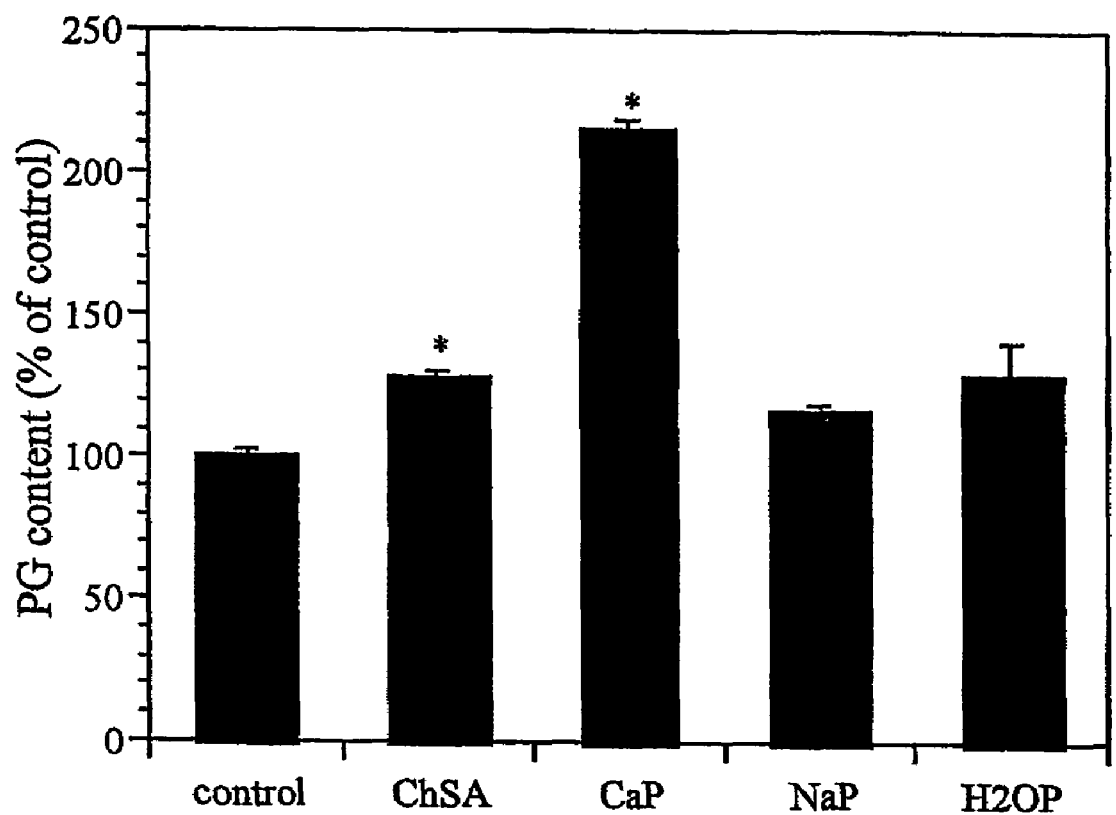
Figure 26:
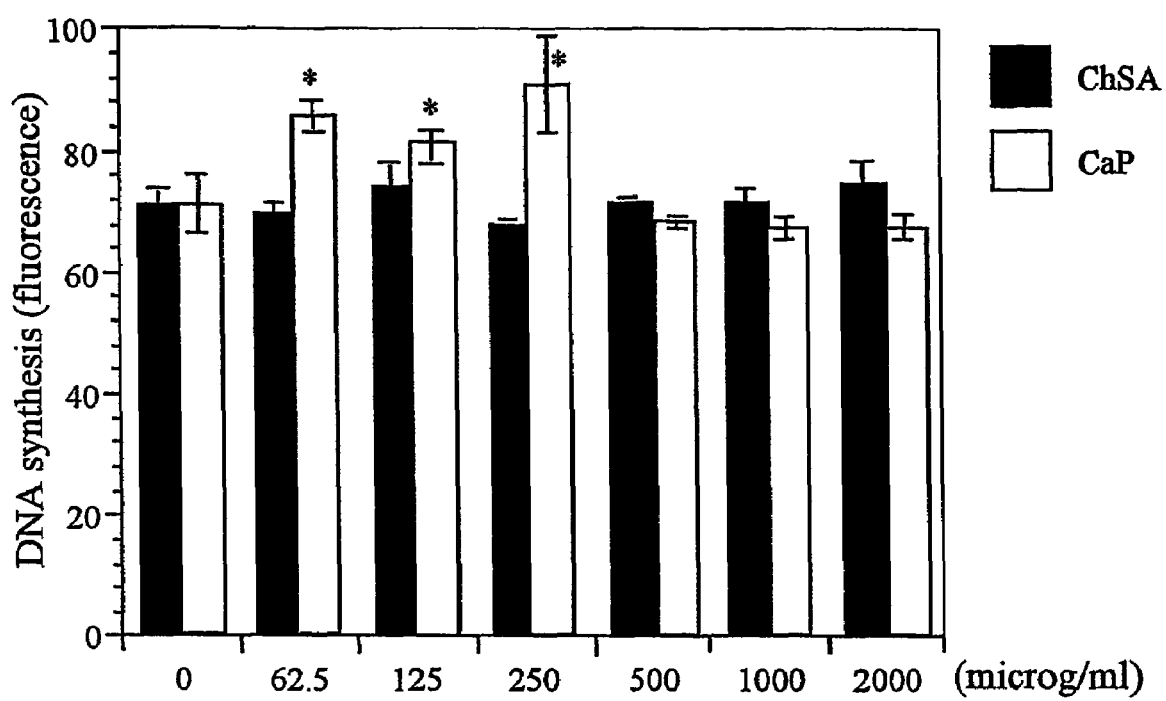
Figure 27:
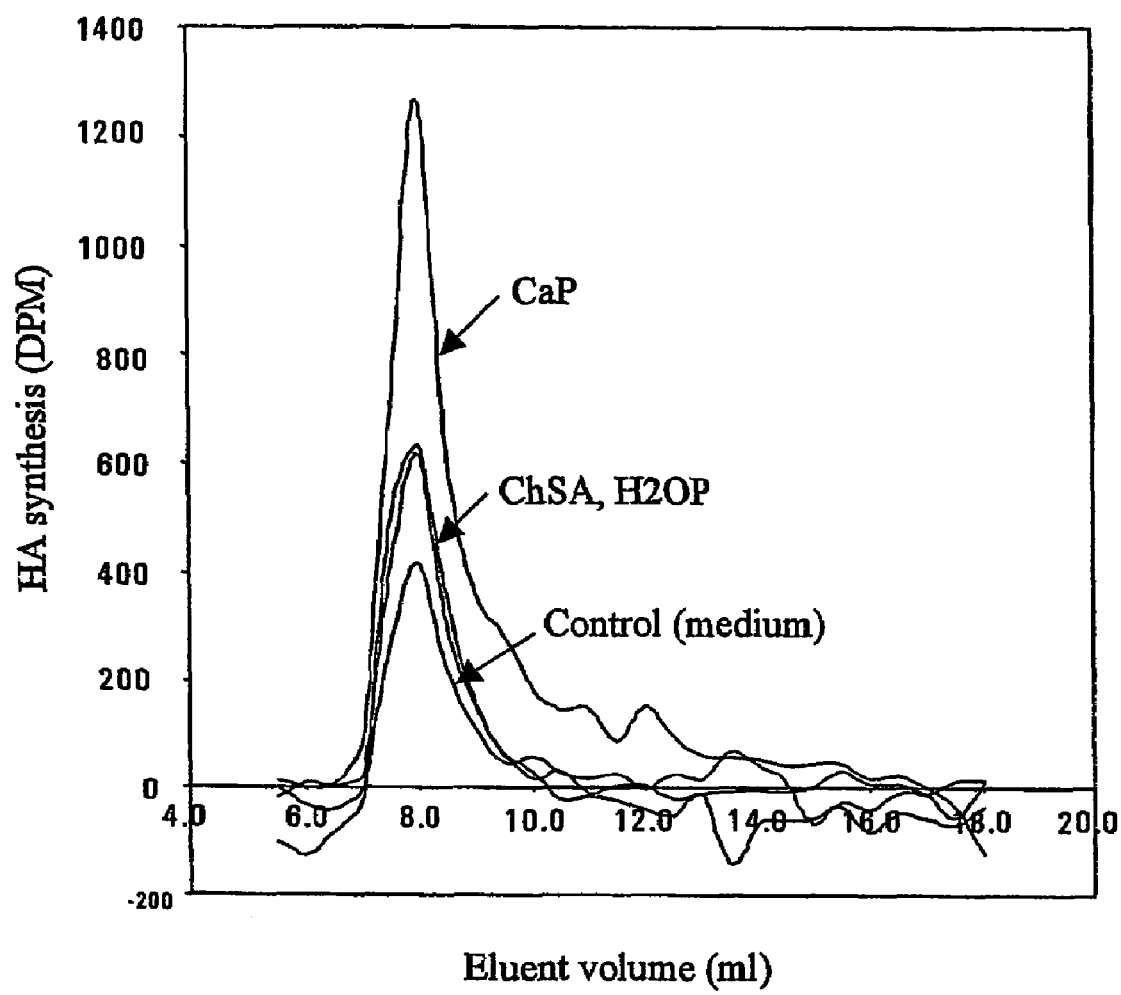

The knee joint menisci are structurally complex fibrocartilages which perform an essential role for the weight bearing functions of diarthrodial joints. They are crescent shaped cartilages in which the outer rim is under high tensile stresses and the inner region is subjected to more compressional loading. The fibrochondrocytes from these two regions are therefore metabolically different and were for this reason studied separately. When fibrochondrocytes from the inner region of ovine menisci were cultured with various concentrations of ChS and the Peptacans, only CaP stimulated PG synthesis (FIGS. 18 & 19). At 2.0 mg/ml a 200% stimulation of PG synthesis was obtained for CaP and a 130% increase for ChS but only for PGs released into the media (FIGS. 20 & 21). CaP was observed to produce a similar PG stimulatory profile on fibrochondrocytes isolated from the outer region of the meniscus (FIGS. 22, 23 & 24) but in these cultures ChS failed to elicit a significant increase in media PG levels (FIG. 25).

The major non-proteinaceous component of joint synovial fluid is hyaluronan (HA). As already indicated HA confers to synovial fluid its unique rheological properties which includes exceptionally efficient lubrication of articular cartilage and peri-articular tissues. In rheumatoid and osteoarthritic joints synovial fluid HA concentration and molecular weight are decreased (Dahl L B, Dahl I M S, Engstrom-Laurent A, Granath K. Concentration and molecular weight of sodium hyaluronate in synovial fluid from patients with rheumatoid arthritis and other arthropathies. Ann Rheum Dis 1985;44:817-22). Since the rheological effects of HA are dependent on its molecular weight and concentration, a decline in either or both of these parameters decreases the ability of synovial fluid to efficiently lubricate and protect articulating surfaces. However, HA is also anti-inflammatory and exhibits a number of other important functions essential in joint physiology (Ghosh P and Guidolin D, Potential mechanism of action of intra-articular hyaluronan therapy in osteoarthritis: Are the effects molecular weight dependent?, Seminars in Arthritis and Rheumatism 2002, 32: 10-37). Diminished HA concentration and a reduction in its molecular weight could therefore have profound effects, not only on the rheological properties of synovial fluid, but synovial and inflammatory cell functions and their macromolecular expression. Synovial fluid HA is almost exclusively synthesized by type B cells of the synovial lining. These fibroblasts (synoviocytes) when isolated from synovial joints and established in culture retain their phenotypic expression and elaborate HA into culture media. Fibroblast cultures derived from rheumatoid or osteoarthritic joints show aberrant biosynthesis of HA reflecting the abnormal metabolic status of the joints from which they were derived (Smith M M, Ghosh P. The synthesis of hyaluronic acid by human synovial fibroblasts is influenced by the nature of the hyaluronate in the extracellular environment. Rheumatol Int 1987;7:113-22). Generally the amount of HA synthesized is less than obtained from normal synoviocytes and its molecular weight is reduced.

Figure 28:
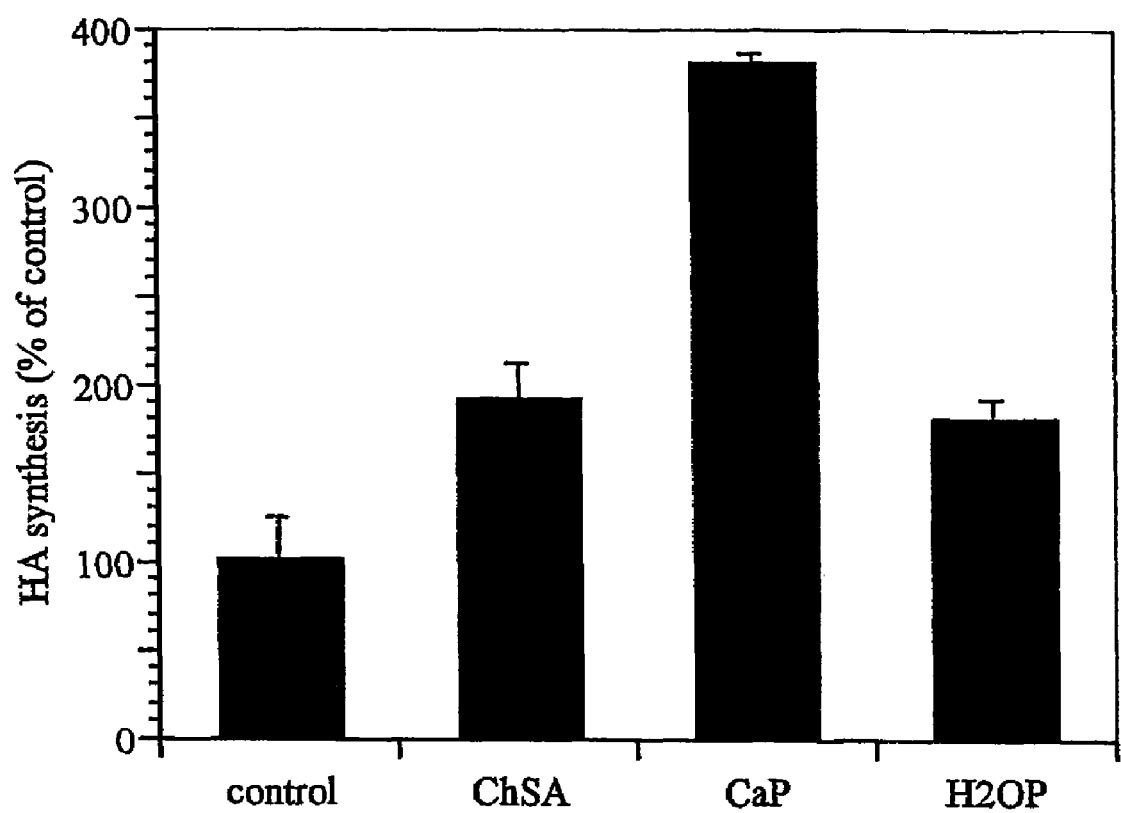

In the present experiments Peptacans and ChS were evaluated for their respective abilities to promote the biosynthesis of DNA and high molecular weight HA by synovial fibroblasts obtained from joints of patients with OA. The results obtained are shown in FIGS. 26-29. As is evident from FIG. 26 only CaP exhibited a significant effect on DNA synthesis at concentrations up to 250 micrograms/mL. However, HA synthesis by these cells was increased 230% at 250 micrograms/mL (FIG. 27) and 380% at 2.0 mg/mL (FIG. 28). The identity molecular weight of the HA synthetised was confirmed by chromatography (FIG. 27) and agarose gel electrophoresis (results not shown). The relative activities of ChS, CaP and H2OP when incubated with the cells at a concentration of 2.0 mg/ml are shown in FIG. 28. The reason for the significant differential effects between CaP and H2OP on HA synthesis by these cells is presently unresolved but was a surprising finding.

Figure 29:
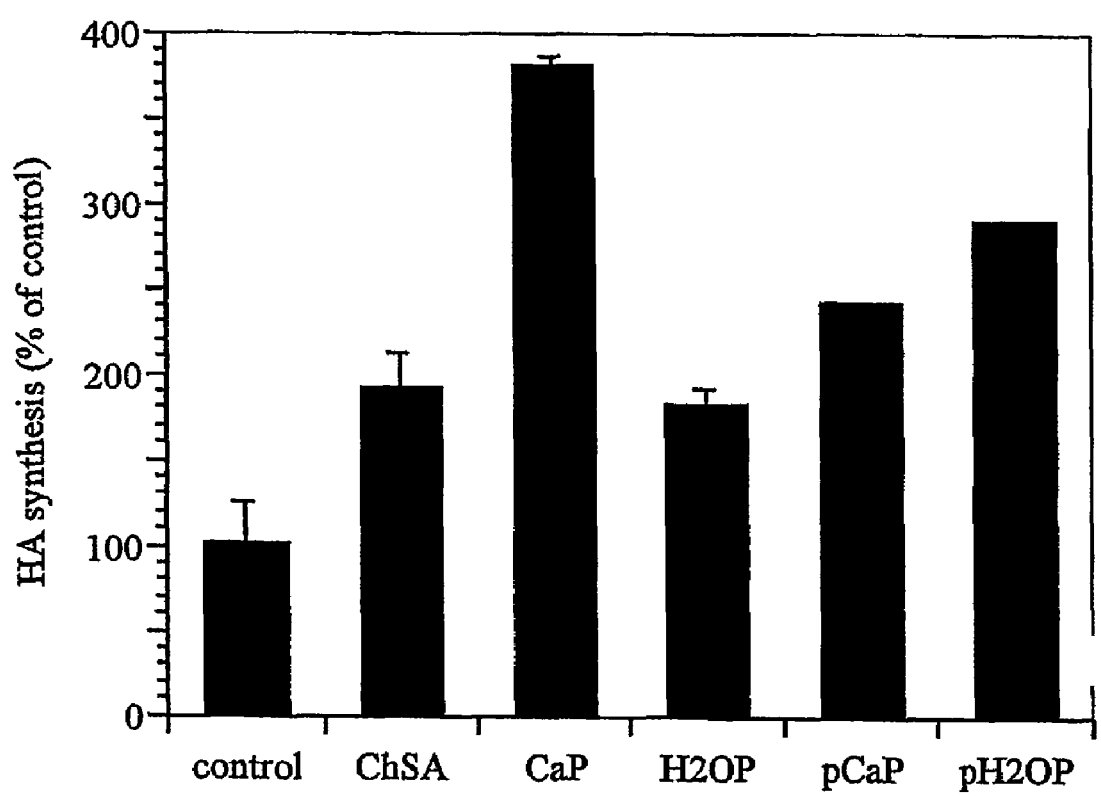

The relative activities of CaP, pCaP and pH2OP studied under the same conditions are included in FIG. 29. This result shows the higher activity of CaP relative to the column purified (pCaP) preparation with regard to the stimulation of HA synthesis by human OA synovial fibroblasts. This result suggests that polypeptides in CaP may be acting synergistically with the calcium GAG-peptide complex.

Figure 30:
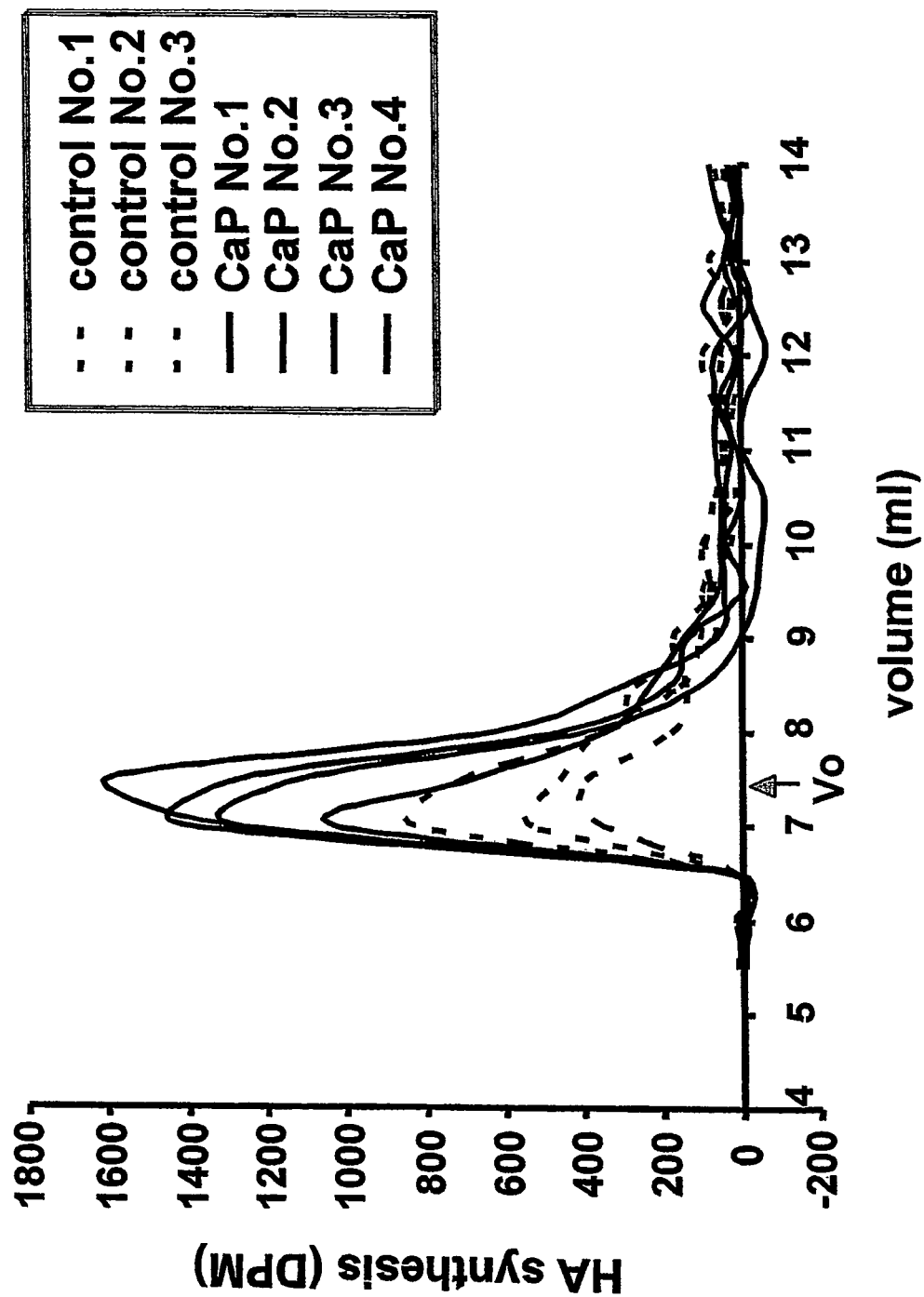
Figure 31:
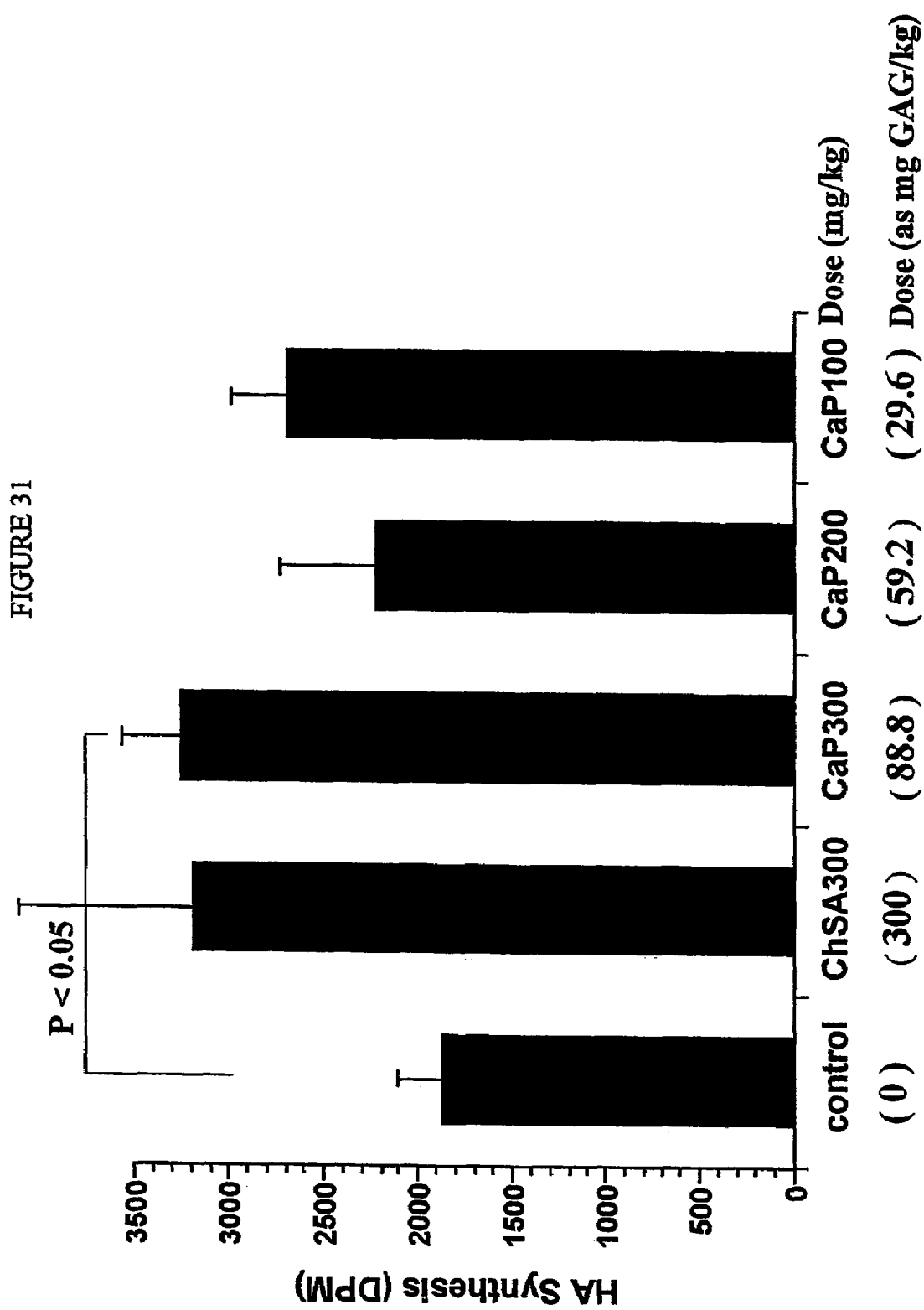

The in vitro stimulation of the biosynthesis of HA by synovial fibroblasts derived from joints of humans with osteoarthritis by CaP was also demonstrated to occur in vivo using an animal model of arthritis. In these latter experiments ChS at 300 mg/kg or CaP at 100, 200, or 300 mg/kg was administered orally to rabbits in which monoarticular proliferative arthritis had been induced by the intra-articular injection of a PC-complex. The preparations were given daily for 7 days before arthritis was inducted and daily for 7 days thereafter. Animals were euthanased and blood and tissues collected for analysis on day 14. Synovial fibroblasts from the joints of these animals together with those from a non-drug treated arthritis control group were established in primary cell culture and the biosynthesis of radiolabelled HA determined as described for the in vitro studies. The results of these experiments are shown in FIGS. 30 and 31. Compared to the non-drug treated control group synovial fibroblasts from all animals in the CaP treated group showed higher synthesis of HA (FIG. 30), however, because of the inter-animal biological variation only the group receiving the dose of 300 mg/kg were statistically significant ($p<0.05$) relative to the non-drug-treated group (FIG. 31). If the comparison of HA stimulation by the treatments was based on their respective sulfated GAG content then CaP was more than 3× more active than ChS. Promotion of HA synthesis by synovial cells in arthritic joints would contribute to improved joint lubrication and a reduction of cartilage degradation as has already been discussed in detail elsewhere in this disclosure.

Figure 32:
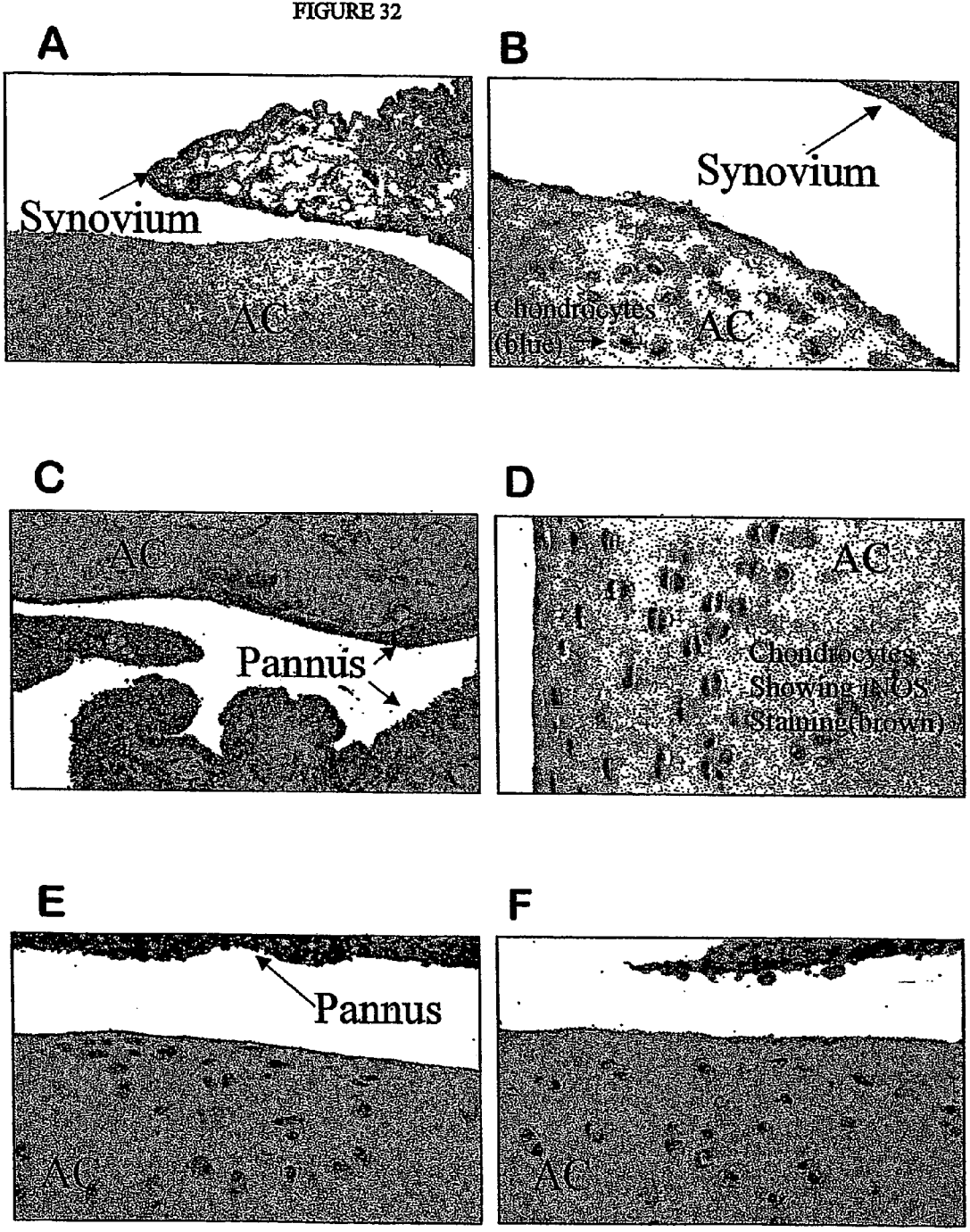
Figure 33:
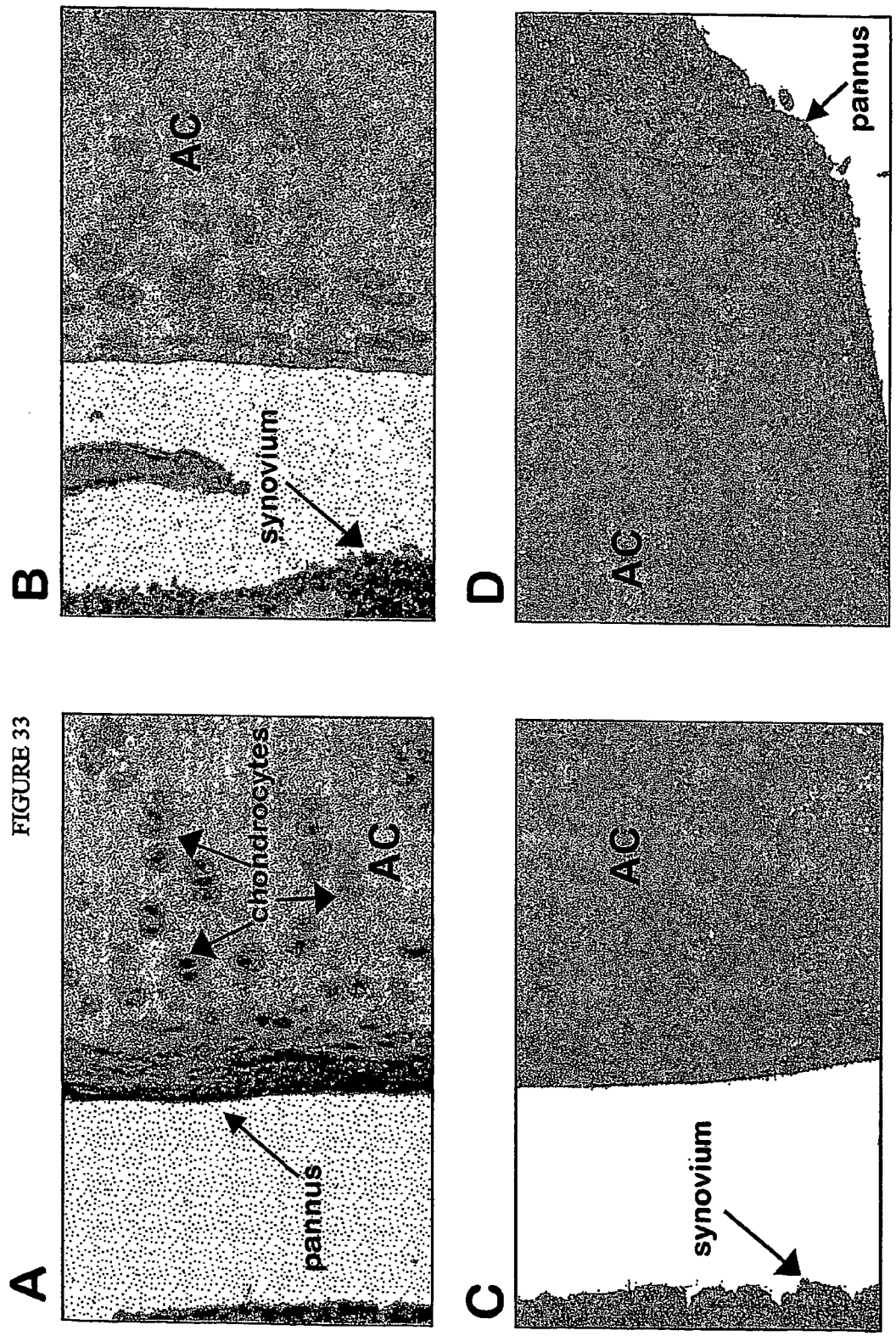

The extensive synovial inflammation provoked in the rabbit joints by the intra-articular injection of the arthritogen (PC complex) was very apparent from the histological sections of the synovial membranes which showed massive cellular infiltration, connective proliferation, hyperplasia and neovascularlization. In the non-drug treated control group these inflammatory events were further characterised by the presence of an invasive pannus originating from the synovial tissues at the joint margins. Beneath and adjacent to this pannus tissue destruction of cartilage and subchondral bone was evident (FIGS. 32 and 33). In the drug treated groups synovitis was not abrogated but the extent of pannus formation was reduced and the structural integrity of cartilage largely preserved. Furthermore, the expression by chondrocytes in the patella cartilage of inducible nitric oxide synthase (iNOS), the intra-cellular enzyme responsible for the production of nitric oxide free radicals, was mitigated particularly in the high dose CaP treated animals (FIG. 32). This observation was consistent with the level of immunohistochemical staining for nitrotyrosine, which is a characteristic product marker of the chemical action of nitric oxide radical on intra-cellular proteins (Kobayashi K, et al., Chondrocyte apoptosis and regional differential expression of nitric oxide in the medial meniscus following partial meniscectomy. J Orthopaedic Res, 2001,19: 802-808). As can be seen in FIG. 33 staining for this product was substantially reduced in chondrocytes from cartilages from joints of the CaP treated animals. This reduction in chondrocyte production of iNOS and thus nitric oxide free radicals by CaP treatment is considered to arise from its ability to modulate the effects of pro-inflammatory cytokines (such as interleukin-1) as suggested by the in-vitro experiments. Interleukin-1 is known to be a major initiators of nitric oxide and other free radical production, synovitis inflammation and tissue destruction within arthritic joints (Taskiran D, Stefanovic-Racic M, Georgescu H, Evans C. Nitric oxide mediates suppression of cartilage proteoglycan synthesis by interleukin-1. Biochem Biophys Res Commun 1994;200: 142-8). However, CaP could also have a direct inhibitory effect on nitric oxide radical activity or its production by synovial cells and chondrocytes which in itself would be a useful means of suppressing inflammation and tissue destruction in arthritic joints. Such a strategy which has already been suggested by others using synthetic iNOS inhibitors (U.S. Pat. No. 6,346,519, February 2002).

Figure 34:
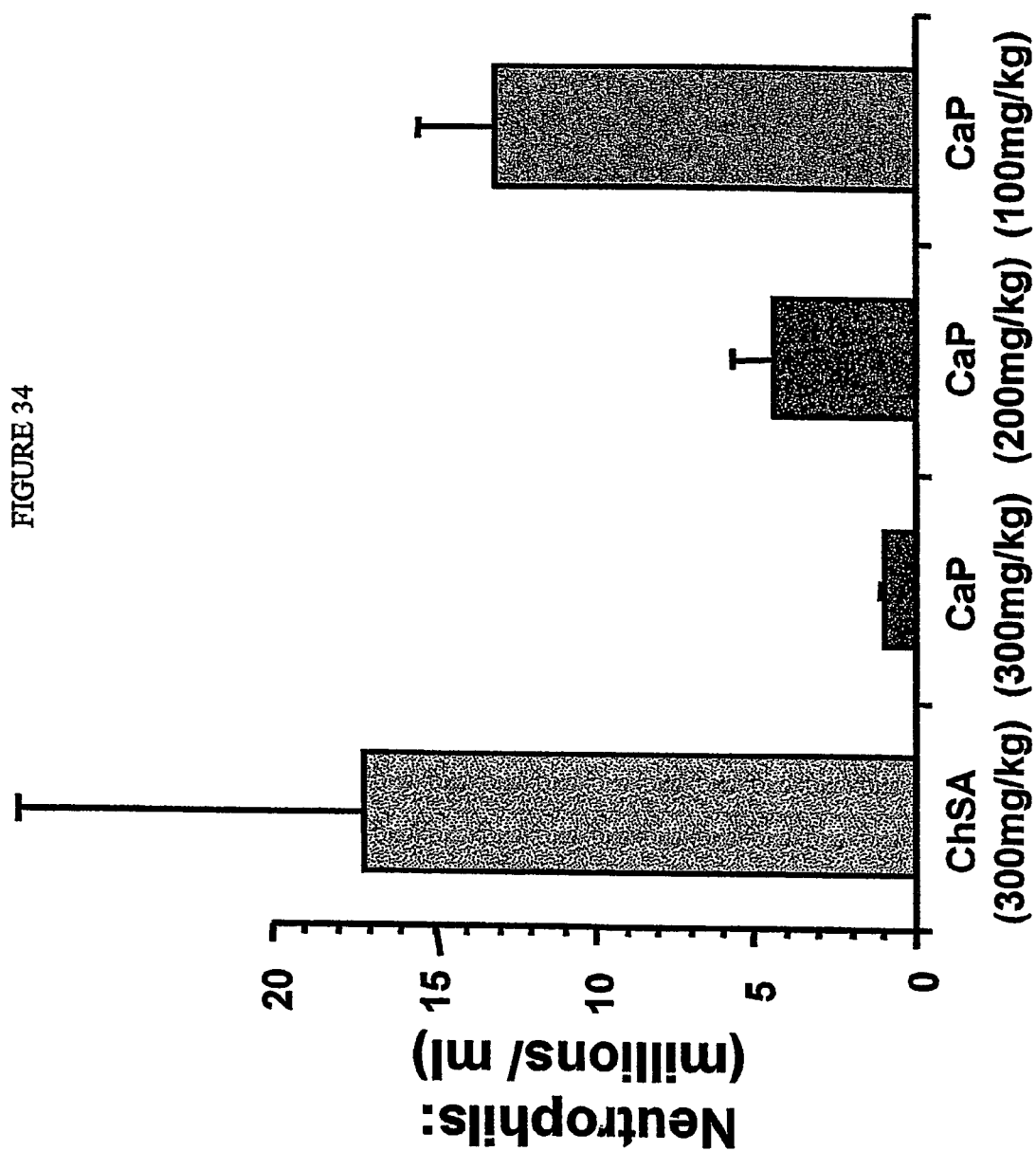
Figure 35:
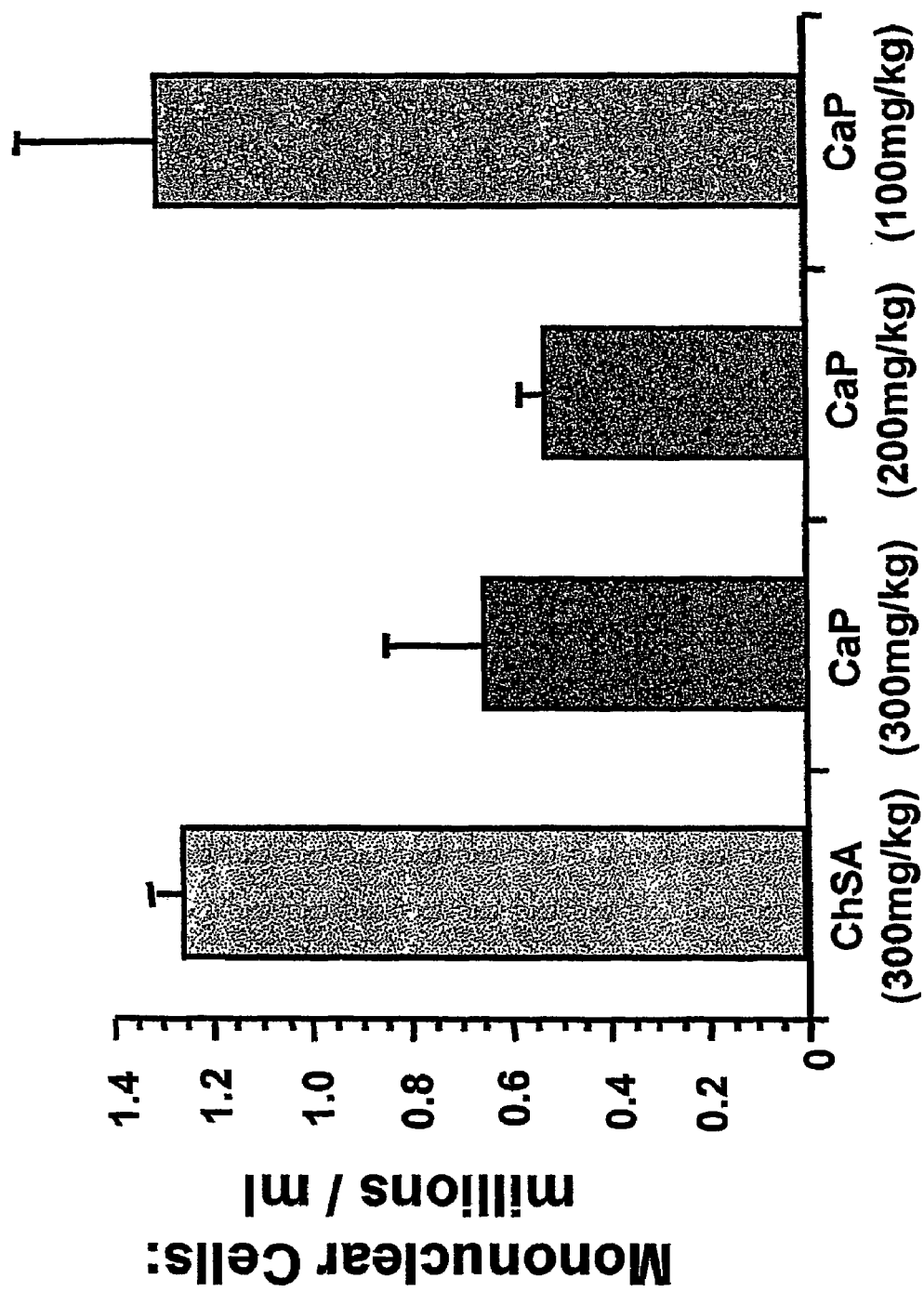

In addition to the beneficial effects mediated by CaP on the joint tissues of the rabbit arthritis model described above, it was also found to suppress the levels of both neutrophils and mononuclear cells circulating in the blood of the arthritic animals (FIGS. 34 and 35). Using the ChS treated animals as drug treated control group, it was evident that this suppressive effect of CaP was dose dependent, the 300 mg/kg dose being the more effective, particularly on circulating neutrophil numbers (FIG. 34). While these blood borne white cells serve as an important vanguard in the immune defense against invading pathogens, once activated, as occurs in inflammatory states such as rheumatoid arthritis and osteoarthritis, emphysema, inflammatory bowel disease, vasculitis and suchlike, they provide an ongoing source of destructive proteinases, oxygen derived free radicals and pro-inflammatory cytokines all of which contribute to the initiation and perpetuation of the disease process. Immunosuppression in these inflammatory conditions, has and continues to be, an important therapeutic objective for their treatment (St. Georgiev V, Immunomodulating drugs: major advances in research and development in Immunomodulating drugs, Editors: St. Georgiev V and Yamaguchi H, Ann NY Acad Science, 1993, 685, 1-10). Moreover, immunosuppressive therapy has been extensively used for the management of chronic rheumatoid arthritis for over 30 years (Weinblatt M E, Immunosuppressive therapy in rheumatoid arthritis, in: Therapeutic control of inflammatory disease, new approaches to antirheumatic drugs, Editors: Otterness I, Lewis A, Capetola R, Advances in inflammation research, Vol 11, Raven Press, New York, 1986, pp265-276). Although the suppressive effects on white cells observed for high oral dose CaP in the rabbit model of mono-articular proliferative arthritis used here appear to be a novel finding for a nutraceutical preparation, it is known that oral administration of cartilage derived antigens, such as type II collagen peptides can induce cell energy and/or active cellular suppression of immune responses by promoting clonal selection and the secretion of anti-inflammatory cytokines, such as interleukins-4 and 10 and transforming growth factor-beta (TGF-beta). Furthermore, oral administration of these cartilage antigens have be used to treat inflammatory joint diseases such as rheumatoid arthritis (Kagnoff M F, Oral tolerance: mechanisms and possible role in inflammatory joint diseases, Baillieres's Clinical Rheumatology, 1996, 10: 41-54; Weiner H L and Komagata Y, Oral Tolerance and the treatment of rheumatoid arthritis. Sem Immunopathol, 1998, 20: 289-308)

INDUSTRIAL APPLICABILITY

GAG-peptide complexes and polypeptides substantially free of DNA may be used, either directly or after further processing, for the treatment, protection and restoration of connective tissues in inflammatory and degenerative tissue disorders such as rheumatoid arthritis and osteoarthritis in any of their multiple forms, atherosclerosis and myocardial ischemia, degenerative and diabetic arteriopathies, thrombosis and embolisms, hyperlipideamis and as anti-angiogenic agents for the treatment of cancers.

Because the compounds are substantially free of DNA, they are also substantially free of other molecules such as viruses that may be associated with DNA. An avoidance of such associated molecules could avoid health risks. Bovine and other animal nucleic acids are strongly bound to or form complexes with retroviruses and heat/protease resistant prion proteins which have beep implicated in the spread of transmissible spongiform encephalopathies such as Creutzfeld-Jakob disease, kuru, Gerstmann-Straussler-Scheiner syndrome in humans, scrapie in sheep and goats, and bovine spongiform encapalopathies in cattle.

Calcium salts of GAG-peptide complexes have been found to have particular pharmacological efficacy which is further enhanced in combination with matrix polypeptides. Ingestion of calcium salts would provide an added benefit in being a source of dietary calcium.

The method of the present invention is essentially non-disruptive to the connective tissue used. Thus the residual tissue particles remaining after the autolysis is completed and the medium containing the GAG-peptide complexes and polypeptides has been removed, can still be used as a source of collagen derivatives. In this regard it should be noted that traditional methods for preparing ChS from connective tissues such as cartilage use exhaustive proteolytic or chemical digestion to destroy the proteinaceous components of the matrix to allow the ChS to be released into aqueous solutions and isolated. The residual cartilage particles obtained by the present method can be hydrolysed proteolytically or chemically to obtain collagen peptides of variable molecular size to be used for the treatment, protection and restoration of connective tissues in inflammatory and degenerative disorders such as rheumatoid arthritis and osteoarthritis in any of their multiple forms or for the enhancement of wound healing or for the preparation of artificial biomatrices for cell culture, cell transplantation, or delivery of bioactive compounds including drugs and growth factors into a host issue.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive. The invention will now be further described by the following paragraphs:

A. A method for the preparation of a composition comprising a connective tissue-derived GAG-peptide complex and polypeptide said method comprising the steps of:
  subjecting particles of connective tissue to enzyme mediated autolysis by contacting with an autolysis medium containing a divalent salt at a pH of from about 2.5 to about 8.5 and at an effective temperature such that at least one GAG-peptide complex and at least one polypeptide are released substantially free of DNA, by the proteolytic actions of an endogenous enzyme(s) from within the tissue particles, into the autolysis medium, leaving residual tissue particles; and
  recovering the at least one GAG-peptide complex and at least one polypeptide from the autolysis medium.

B. A method according to paragraph A wherein the divalent salt is selected from the group consisting of calcium, magnesium, copper, zinc and mixtures thereof.

C. A method according to paragraph A, wherein the divalent salt is calcium.

D. A method according to paragraph A wherein the pH is in the range of from 3.5 to 8.0, more preferably 4 to 7, most preferably 4.5 to 7.

E. The method according to paragraph A wherein the temperature is in the range of from 20 to 45° C., preferably 25 to 45° C., more preferably 32 to 45° C., most preferably 37° C.

F. The method according to paragraph A wherein the connective tissue is selected from the group consisting of skin, bone, tendon, ligament and cartilage.

G. The method according to paragraph A wherein the connective tissue is selected from the group consisting of bovine, ovine, porcine, cervine and equine connective tissue.

H. The method according to paragraph G wherein the connective tissue is selected from the group consisting of auricular, articular tracheal and nasal cartilage.

I. The method according to paragraph A further comprising, separating the GAG-peptide complex from the polypeptide and recovering the GAG-peptide complex.

J. A composition comprising at least one GAG-peptide complex substantially free of DNA or a salt thereof and at least one polypeptide substantially free of DNA, wherein the GAG-peptide complex and polypeptide are obtainable by the method according to any one of paragraph A to H.

K. A composition comprising at least one GAG-polypeptide complex substantially free of DNA or a salt thereof, wherein the GAG-peptide complex is obtainable by the method according to paragraph I.

L. A composition comprising chondroitin sulfate substantially free of DNA or salt thereof derived from a GAG-peptide complex substantially free of DNA, wherein said GAG-peptide complex is obtainable by the method according to paragraph I.

M. The composition according to paragraphs K or L wherein the salt is selected from the group consisting of calcium, magnesium, copper, zinc and mixtures thereof.

N. Use of at least one GAG-peptide complex substantially free of DNA or salt thereof and at least one polypeptide substantially free of DNA in the manufacture of a medicament for treatment of inflammatory and degenerative tissue disorders such as rheumatoid arthritis and osteoarthritis in any of their multiple forms, atherosclerosis and myocardial ischemia, degenerative and diabetic arteriopathies, thrombosis and embolisms, hyperlipideamis and for the treatment of cancers,
  wherein the GAG-peptide complex and polypeptide are obtainable by subjecting particles of connective tissue to enzyme mediated autolysis by contacting with an autolysis medium containing a monovalent or divalent salt at an effective pH and temperature such that at least one GAG-peptide complex and at least one polypeptide are released substantially free of DNA, by the proteolytic actions of an endogenous enzyme(s) from within the tissue particles, into the autolysis medium, leaving residual tissue particles; and
  recovering the GAG-peptide complex(es) and polypeptide(s) from the autolysis medium, substantially free of DNA.

O. Use of at least one GAG-peptide complex substantially free of DNA or salt thereof in the manufacture of a medicament for treatment of inflammatory and degenerative tissue disorders such as rheumatoid arthritis and osteoarthritis in any of their multiple forms, atherosclerosis and myocardial ischemia, degenerative and diabetic arteriopathies, thrombosis and embolisms, hyperlipideamis and for the treatment of cancers,
  wherein the GAG-peptide complex is obtainable by subjecting particles of connective tissue to enzyme mediated autolysis by contacting with an autolysis medium containing a monovalent or divalent salt at an effective pH and temperature such that at least one GAG-peptide complex and at least one polypeptide are released substantially free of DNA, by the proteolytic actions of an endogenous enzyme(s) from within the tissue particles, into the autolysis medium, leaving residual tissue particles; and
  recovering the GAG-peptide complex(es) and polypeptide(s) from the autolysis medium, separating the GAG-peptide from the polypeptide and recovering the GAG-peptide.

P. Use of at least one chondroitin sulfate substantially free of DNA or salt thereof in the manufacture of a medicament for treatment of inflammatory and degenerative tissue disorders such as rheumatoid arthritis and osteoarthritis in any of their multiple forms, atherosclerosis and myocardial ischemia, degenerative and diabetic arteriopathies, thrombosis and embolisms, hyperlipideamis and for the treatment of cancers, wherein the chondroitan sulfate is derived from a GAG-peptide complex substantially free of DNA which is obtainable by the method according to paragraph 9.

Q. Use according to any one of paragraphs M-P, wherein the salt is selected from the group consisting of calcium, magnesium, copper, zinc and mixtures thereof.

R. Use according to paragraph Q, wherein the salt is a calcium salt.

S. Use according to paragraph R, wherein the GAG-peptide complex and the polypeptide are obtained by the method according to any one of paragraphs A to I.

T. A method for the treatment of inflammatory and degenerative tissue disorders such as rheumatoid arthritis and osteoarthritis in any of their multiple forms, atherosclerosis and myocardial ischemia, degenerative and diabetic arteriopathies, thrombosis and embolisms, hyperlipideamis and for the treatment of cancers, the method comprising administering to a subject in need of such treatment an effective amount of at least one connective tissue derived GQG-peptide complex or salt thereof and at least one polypeptide,
 wherein the GAG-peptide complex and polypeptide are obtainable by subjecting particles of connective tissue to enzyme mediated autolysis by contacting with an autolysis medium containing a monovalent or divalent salt at an effective pH and temperature such that at least one GAG-peptide complex and at least one polypeptide are released substantially free of DNA, by the proteolytic actions of an endogenous enzyme(s) from within the tissue particles, into the autolysis medium, leaving residual tissue particles; and
 recovering the GAG-peptide complex and polypeptide from the autolysis medium.

U. A method for the treatment of inflammatory and degenerative tissue disorders such as rheumatoid arthritis and osteoarthritis in any of their multiple forms, atherosclerosis and myocardial ischemia, degenerative and diabetic arteriopathies, thrombosis and embolisms, hyperlipideamis and for the treatment of cancers, the method comprising administering to a subject in need of such treatment an effective amount of at least one connective tissue derived GAG-peptide complex or salt thereof,
 wherein the GAG-peptide complex is obtainable by subjecting particles of connective tissue to enzyme mediated autolysis by contacting with an autolysis medium containing a monovalent or divalent salt at an effective pH and temperature such that at least one GAG-peptide complex and at least one polypeptide are released substantially free of DNA, by the proteolytic actions of an endogenous enzyme(s) from within the tissue particles, into the autolysis medium, leaving residual tissue particles;
 recovering the GAG-peptide complex and polypeptide from the autolysis medium, separating the GAG-peptide complex and the polypeptide and recovering the GAG-peptide complex.

V. A method for the treatment of inflammatory and degenerative tissue disorders such as rheumatoid arthritis and osteoarthritis in any of their multiple forms, atherosclerosis and myocardial ischemia, degenerative and diabetic arteriopathies, thrombosis and embolisms, hyperlipideamis and for the treatment of cancers comprising administering to a subject in need of such treatment an effective amount of at least one chondroitin sulfate salt substantially free of DNA obtainable by the method according to any one of paragraphs A to I.

The invention claimed is:

1. A composition suitable for-oral administration, comprising a mixture of one or more connective tissue derived glycosaminoglycan (GAG)-peptide monovalent or divalent salt complexes substantially free of DNA and at least one connective tissue derived polypeptide substantially free of DNA such that the DNA is undetectable by the Hoechst 33258 fluorescence dye binding assay, wherein at least one GAG-peptide complex comprises two GAG-chains attached to the peptide.

2. The composition according to claim 1 wherein the composition has a neutral pH.

3. The composition according to claim 1 wherein the GAG-peptide salt complex is a divalent salt complex.

4. The composition according to claim 1 wherein the GAG-peptide salt complex is selected from the group consisting of calcium, magnesium, copper, zinc or mixtures thereof.

5. The composition according to claim 1 wherein the GAG-peptide salt complex has an average molecular weight of about 31.1 kDa.

6. The composition according to claim 1 wherein the GAG-peptide salt complex has an average molecular weight of about 33.7 or 46.1 kDa.

7. The composition according to claim 1 wherein the GAG-peptide salt complex has an average molecular weight of about 33.7 kDa.

8. The composition according to claim 1 wherein the GAG-peptide salt complex is obtainable by a method comprising the steps of:
 subjecting particles of connective tissue to enzymes mediated autolysis by contact with an autolysis medium containing a salt at a pH of from about 2.5 to about 8.5 and at an effective temperature such that at least one GAG-peptide salt complex is released substantially free of DNA, by the proteolytic actions of an endogenous enzyme from within the tissue particles, into the autolysis medium, leaving residual tissue particles; and
 recovering the at least one GAG-peptide salt complex from the autolysis medium.

9. The composition according to claim 8, wherein the GAG-peptide is recovered in an aqueous phase.

10. The composition according to claim 9, wherein the aqueous is neutralised.

11. The composition according to claim 1, wherein the GAG-peptide salt complex is cartilage derived.

* * * * *